United States Patent
Hu

(10) Patent No.: US 8,426,448 B2
(45) Date of Patent: *Apr. 23, 2013

(54) 1,5-DIPHENYL-PYRROLIDIN-2-ONE COMPOUNDS AS CB-1 LIGANDS

(75) Inventor: Jingdan Hu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 113 days.

This patent is subject to a terminal disclaimer.

(21) Appl. No.: 12/935,593

(22) PCT Filed: Apr. 2, 2009

(86) PCT No.: PCT/US2009/039254
§ 371 (c)(1),
(2), (4) Date: Sep. 30, 2010

(87) PCT Pub. No.: WO2009/131814
PCT Pub. Date: Oct. 29, 2009

(65) Prior Publication Data
US 2011/0028520 A1 Feb. 3, 2011

Related U.S. Application Data

(60) Provisional application No. 61/046,936, filed on Apr. 22, 2008.

(51) Int. Cl.
*C07D 401/12* (2006.01)
*A61K 31/4439* (2006.01)

(52) U.S. Cl.
USPC ........................................ 514/343; 546/278.1

(58) Field of Classification Search ........................ None
See application file for complete search history.

(56) References Cited

U.S. PATENT DOCUMENTS 7,998,985 B2 * 8/2011 Schaus ........................... 514/343

FOREIGN PATENT DOCUMENTS

| WO | 2005/077911 A | 8/2005 |
|---|---|---|
| WO | 2005080345 A | 9/2005 |
| WO | 2007/020502 A | 2/2007 |
| WO | 2008/070305 A | 6/2008 |
| WO | 2008/070306 A | 6/2008 |

OTHER PUBLICATIONS

Jang et al., Pharmacokinetics and Its Role in Small Molecule Drug Discovery Research, Medicinal Research Reviews, vol. 21, No. 5, pp. 382-396, 2001.
Delapp et al, Determination of [35S]Guanosine-5'-O-(3-thio)Triphosphate Binding mediated by Cholinergic Muscarinic Receptors in Membranes from Chinese Hamster Ovary Cells and Rat Striatum Using an Anti-G Protein Scintillation Proximity Assay1, The Journal of Pharmacology and Experimental Therapeutics, vol. 289, No. 2, pp. 946-955, 1999.
Cheng et al., Relationship Between the Inhibition Constant (KI) and the Concentration of Inhibitor Which Causes 50 Percent Inhibition (I50) of an Enzymatic Reaction, Biochemical Pharmacology, vol. 22, pp. 3099-3108 1973.
Andreichikov et al., Zhurnal Organicheskoi Khimii, vol. 22, No. 10, pp. 2208-2203 1986.
Pacher et al., The Endocannabinoid System as an Emerging Target of Pharmacotherapy, vol. 58, No. 3, pp. 389-462, 2006.

* cited by examiner

Primary Examiner — Zinna Northington Davis
(74) Attorney, Agent, or Firm — R. Craig Tucker

(57) ABSTRACT

CB-1 receptor inverse agonist compounds of Formula

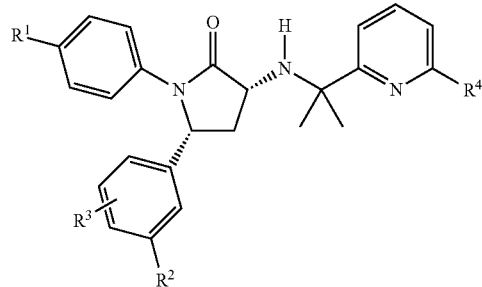

and pharmaceutical compositions for the treatment of obesity or cognitive impairment associated with schizophrenia.

13 Claims, No Drawings

1,5-DIPHENYL-PYRROLIDIN-2-ONE COMPOUNDS AS CB-1 LIGANDS

This application is a United States national phase entry, pursuant to 35 U.S.C. 371, of /PCT/US2009/039254, filed Apr. 2, 2009, which claims the benefit of U.S. provisional patent application No. 61/046,936, filed Apr. 22, 2008.

The cannabinoid CB-1 receptor (CB-1) is primarily found in the central and peripheral nervous systems and to a lesser extent in several peripheral organs. The cannabinoid CB-2 receptor (CB-2) is found primarily in the immune system. The pharmacology and therapeutic potential for cannabinoid receptor ligands has been reviewed (Pacher, et al. Pharmacol. Rev. (2006) 58, 389)). CB-1 receptor antagonists/inverse agonists have been shown effective for reducing feeding and body weight in animal models of obesity. CB-1 antagonists/inverse agonists have been shown to further potentiate the activity of antipsychotic agents in various assays and may be effective in treating both negative and cognitive symptoms of schizophrenia. In addition, the weight loss effects of CB-1 antagonists/inverse agonists have been demonstrated in animal models of antipsychotic treatment-induced weight gain and therefore may also be effective in controlling the treatment-emergent weight gain and metabolic syndrome seen with current antipsychotic therapies. Moreover, CB-1 receptor antagonists/inverse agonists have been shown to reduce alcohol consumption in animal models of alcohol drinking and therefore may be useful in the treatment of alcoholism and/or substance abuse.

Compounds acting at the CB-2 receptor may have effects on immune function. Therefore, in developing therapeutic agents active at the CB-1 receptor, it is desirable to have high selectivity for the CB-1 receptor versus the CB-2 receptor to avoid undesirable effects.

A number of centrally acting CB-1 receptor antagonists/inverse agonists have been studied for the treatment of obesity and/or other disorders. As for example, WO2007/020502 discloses certain substituted pyrrolidin-2-one compounds as CB-1 antagonists.

Oral administration is typically the preferred route of administration for agents for the treatment of obesity and/or schizophrenia. For compounds to display good oral bioavailability, they typically must have good aqueous solubility and sufficient metabolic stability to minimize first pass degradation in the liver. Endogenous cannabinoid ligands and the complementary site to which they bind in the CB-1 receptor are highly lipophilic. Consequently, known CB-1 receptor ligands have also tended to be lipophilic, which leads to poor solubility. Also many CB-1 receptor ligands have been relatively metabolically labile. These solubility and/or metabolism properties of many CB-1 compounds have resulted in limited oral absorption and bioavailability.

Oxidative metabolism of some compounds may lead to the formation of reactive, electrophilic metabolic intermediates. Such intermediates are prone to reaction with other nucleophiles in the body such as proteins, glutathione, DNA, RNA, etc., which can lead to undesirable toxic effects.

The pharmacokinetic properties of a therapeutic agent can be influenced by the co-administration of other agents. These so-called drug-drug interactions may lead to either an increase or decrease in the plasma exposure of the therapeutic agent, leading to problems with tolerability and/or efficacy of the agent. Compounds which are metabolically cleared through saturatable mechanisms, (e.g. CYP3A4, CYP2D6, CYP2C9, and CYP1A2) are particularly prone to suffer from such drug-drug interactions. Conversely, compounds that inhibit these saturatable mechanisms are prone to cause such drug-drug interactions. Some known CB-1 antagonists/inverse agonists exhibit such liabilities.

There remains a need for CB-1 receptor antagonists or inverse agonists that have high selectivity over CB-2 receptor, have high in vivo potency (low nM $K_b$), have acceptable bioavailability, that do not form reactive metabolic intermediates, and that have decreased potential for drug-drug interactions. The compounds of the present invention provide some or all of these advantages.

The present invention provides compounds of Formula (I)

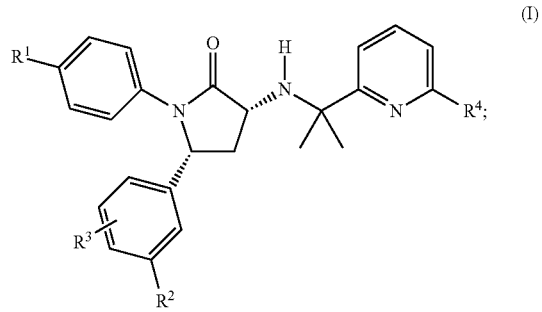

(I)

Wherein:

$R^1$ is selected from the group consisting of hydrogen, chloro, cyano, trifluoromethyl, difluoromethoxy, and trifluoromethoxy;

$R^2$ is selected from the group consisting of hydrogen, halo, cyano, $(C_1-C_3)$ alkyl substituted with from 1 to 5 fluoro groups, and $(C_1-C_3)$ alkoxy substituted with from 1 to 5 fluoro groups;

$R^3$ is selected from the group consisting of hydrogen, fluoro, and chloro;

$R^4$ is selected from the group consisting of trifluoromethyl, cyano and cyclopropyl;

provided that, when $R^1$ is hydrogen, chloro, cyano, or trifluoromethyl, then $R^2$ is $(C_1-C_3)$ alkoxy substituted with from 1 to 5 fluoro groups;

and pharmaceutically acceptable salts thereof.

One of ordinary skill in the art will recognize that the compounds of the present invention may exist in forms having different points of attachment of particular hydrogen atoms and are thus tautomeric. The individual tautomers as well as mixtures thereof are contemplated within the scope of the compounds of Formula (I) as if specifically drawn. Each of the forms of the tautomer may exist, interconvert, and undergo the tautomerization under the conditions specified.

Another aspect of the present invention provides a pharmaceutical composition comprising a compound according to Formula (I), or a pharmaceutically acceptable salt thereof, and a pharmaceutically acceptable carrier, diluent, or excipient.

One embodiment of this aspect of the invention provides a pharmaceutical composition comprising a compound according to Formula (I), or a pharmaceutically acceptable salt thereof, and a pharmaceutically acceptable carrier, diluent, or excipient, wherein the optical purity of the single stereoisomer of the compound of Formula (I) or salt thereof is greater than 90%, preferably greater than 95%, as for example, greater than 99%.

Another aspect of the present invention provides a compound according to Formula (I), or a pharmaceutically acceptable salt thereof, for use in therapy.

One embodiment of this aspect of the present invention provides a compound according to Formula (I), or a pharmaceutically acceptable salt thereof, for use in the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or as an aid for smoking cessation.

Another embodiment of this aspect of the invention provides a compound according to Formula (I), or a pharmaceutically acceptable salt thereof, for use in simultaneous, separate, or sequential combination treatment with an antipsychotic agent in a treatment for weight gain, obesity, schizophrenia, cognitive impairment associated with schizophrenia, negative symptoms associated with schizophrenia, and/or weight gain associated with treatment with an antipsychotic.

In another aspect of the present invention, there is provided the use of a compound according to Formula (I), or a pharmaceutically acceptable salt thereof, in the manufacture of a medicament for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation.

One embodiment of this aspect of the invention provides the use of a compound according to Formula (I), or a pharmaceutically acceptable salt thereof, in the manufacture of a medicament for use in combination therapy for weight gain, obesity, schizophrenia, cognitive impairment associated with schizophrenia, negative symptoms associated with schizophrenia, and/or weight gain associated with treatment with an antipsychotic, wherein said medicament is to be administered in simultaneous, separate or sequential combination with an antipsychotic.

In another aspect of this aspect of the invention there is provided a method for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation in a mammal, particularly a human, comprising administering to a mammal in need of such treatment, an effective amount of a compound according to Formula (I) or a pharmaceutically acceptable salt thereof.

Another embodiment of this aspect of the invention provides a method for the treatment of weight gain, obesity, schizophrenia, cognitive impairment associated with schizophrenia, negative symptoms associated with schizophrenia, and/or weight gain associated with treatment with an antipsychotic in a human, comprising administering to a human in need of such treatment, an effective amount of a compound according to Formula (I), or a pharmaceutically acceptable salt thereof, in simultaneous, separate, or sequential combination with an antipsychotic.

Additionally, the present invention provides a pharmaceutical formulation adapted for the treatment of an eating disorder associated with excessive food intake, weight gain, obesity, schizophrenia, cognitive impairment associated with schizophrenia, negative symptoms associated with schizophrenia, substance abuse, alcohol dependence, and/or weight gain associated with treatment with an antipsychotic, or for an aid for smoking cessation, comprising a compound of Formula (I), or a pharmaceutically acceptable salt thereof, in association with a pharmaceutically acceptable carrier, diluent or excipient.

In the use of the compounds of the present invention in the simultaneous, separate, or sequential combination treatment with an antipsychotic, an atypical antipsychotic is preferred, as for example olanzapine, clozapine, and/or risperidone.

Compounds of Formula (I) are selective inverse agonists or antagonists for the CB-1 receptor. The compounds are particularly selective for the CB-1 receptor over the CB-2 receptor. As inverse agonists (or antagonists) of the CB-1 receptor, the compounds are useful for treatment and/or prevention of conditions associated with the CB-1 receptor. Such conditions include, for example, eating disorders associated with excessive food intake, obesity, schizophrenia, particularly the negative symptoms associated with schizophrenia, as for example cognitive impairment associated with schizophrenia, substance abuse, alcohol dependence, smoking cessation and weight gain associated with treatment with an antipsychotic. See DSM-IV-TR., *Diagnostic and Statistical Manual of Mental Disorders. Revised,* $4^{th}$ Ed., Text Revision (2000). The skilled artisan will recognize that there are alternative nomenclatures, nosologies, and classification systems for pathologic psychological conditions and that these systems evolve with medical scientific progress.

The compounds of Formula (I) can also be used to ameliorate weight gain, whether or not the associated weight gain subject can be classified as clinically obese.

Another aspect of the present invention provides a cosmetic method of inducing weight loss comprising administering to a human a compound of Formula (I).

An effective amount of the compounds of Formula (I) may be administered to a patient in need of such treatment or prophylaxis in order to practice the present methods of therapy. The need for a prophylactic administration according to the methods of the present invention is determined via the use of well-known risk factors. The effective amount of an individual compound is determined, in the final analysis, by the physician in charge of the treatment, but depends on factors such as the disorder to be treated, the severity of the disorder and other diseases or conditions present, the chosen route of administration, other drugs and treatments which the patient may concomitantly require, and other factors in the physician's judgment. The magnitude of therapeutic or prophylactic dose of a compound of Formula (I) will, of course, vary with the patient size and age, the nature and severity of the condition to be treated, the particular compound used, and the desired route of administration.

The dose may be administered in a single daily dose or the total daily dosage may be administered in divided multiple doses, as for example two, three, or four times daily. Furthermore, based on the properties of the individual compound selected for administration and/or the characteristics of the dosage form (i.e., modified release), the dose may be administered less frequently, e.g., weekly, twice weekly, monthly, etc. The unit dosage may be correspondingly larger for the less frequent administration. When administered via, transdermal routes, or through a continual intravenous solution, the dosage administration will, of course, be continuous rather than intermittent throughout the dosage regimen.

As used above and throughout the description of the invention, the following terms, unless otherwise indicated, will have the following meaning:

As used herein the term "$(C_1-C_3)$alkyl" refers to methyl, ethyl, propyl, and isopropyl.

"Halo" refers to a fluoro, chloro, or bromo.

"($C_1$-$C_3$)alkoxy" refers to methoxy, ethoxy, propoxy, and isopropoxy.

"Inverse agonist(s)" shall refer to those compounds which possess negative intrinsic activity by reversing the constitutive activity of the receptor. Inverse agonists act to inhibit or reverse the activity of agonists.

"Obesity" refers to the condition of having a high amount of body fat. A person is considered obese if he or she has a body mass index (BMI) of 30 kg/m² or greater. A person with BMI=27-30 is generally considered overweight. Conventionally, those persons with normal weight have a BMI of 19.9 to 26.9. The obesity may be due to any cause, whether genetic or environmental. Examples of disorders that may result in obesity or be the cause of obesity include overeating, decreased physical activity and pathological conditions showing reduced metabolic activity. The invention is not affected by the exact definition of obesity by the BMI standard and all such definitions are to be considered as equivalents.

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula (I)). It is understood by those of ordinary skill in this art that the terms "pharmaceutical formulation" and "pharmaceutical composition" are generally interchangeable, and they are so used for the purposes of this application. It will also be understood that a pharmaceutical composition according to the present invention will have one or more compounds of Formula (I) and may also contain one or more other active ingredients as desired for a given pharmaceutical composition.

"Prevention" (of obesity or weight gain) refers to preventing obesity from occurring if the treatment is administered prior to the onset of the obese condition.

Moreover, if treatment is commenced in an already obese subject, such treatment is expected to prevent, or to prevent the progression of further weight gain. One example of such prevention is to prevent further weight gain in a human undergoing treatment with an antipsychotic.

Abbreviations used herein are defined as follows:
"AF" means antifoam.
"BSA" means bovine serum albumin.
"CMC" means carboxymethylcellulose.
"DMEA" means N,N-dimethylethanolamine.
"DMF" means N,N-dimethylformamide.
"EtOAc" means ethyl acetate.
"EtOH" means ethyl alcohol.
"$Et_2O$" means diethyl ether.
"GDP" means guanosine diphosphate.
"GTP" means Guanosine-5'-triphosphate.
"GTP-$\gamma^{35}$S" means Guanosine-5' (γ-thio)-triphosphate.
"HEPES" means (4-(2-hydroxyethyl)-1-piperazineethanesulfonic acid).
"HOAc" means acetic acid.
"HPBCD" means hydroxypropyl beta cyclodextrin
"IPA" means isopropanol.
"IPAm" means isopropyl amine.
"i.v" or "iv" means intravenous.
"LCC" means liquid column chromatography.
"MEOP" means microemulsion oil phase.
"MTBE" means tert-butyl methyl ether.
"NaCMC" means sodium carboxymethylcellulose.
"p.o." or "po" means orally.
"SFC" means supercritical fluid chromatography.
"SLS" means sodium lauryl sulfate "THF" means tetrahydrofuran.
"$T_r$" means retention time.

While all of the compounds of the present invention are useful as CB-1 inverse agonists (or antagonists), certain classes are preferred, as for example, compounds having any of the following enumerated selections of substituents:

1) $R^1$ is —$OCF_3$, —$OCHF_2$, —$CF_3$ or —CN.
2) $R^1$ is —$OCF_3$, —$OCHF_2$ or —$CF_3$.
3) $R^1$ is —$OCF_3$ or —$OCHF_2$.
4) $R^1$ is —$OCF_3$ or —$CF_3$.
5) $R^2$ is hydrogen, fluoro, chloro, cyano, trifluoromethyl, 1,1-difluoroethyl, trifluoromethoxy, difluoromethoxy, or 1,1,2,2-tetrafluoroethoxy.
6) $R^2$ is trifluoromethyl, 1,1-difluoroethyl, difluoromethoxy, trifluoromethoxy, or 1,1,2,2-tetrafluoroethoxy.
7) $R^2$ is trifluoromethyl, 1,1-difluoroethyl, difluoromethoxy, trifluoromethoxy, or 1,1,2,2-tetrafluoroethoxy, and $R^3$ is hydrogen.
8) $R^2$ is —$OCF_3$ or —$CF_3$.
9) $R^2$ is —$OCF_3$ or —$CF_3$ and $R^3$ is hydrogen.
10) $R^2$ is –$OCF_3$, —$OCHF_2$, or 1,1,2,2-tetrafluoroethoxy.
11) $R^2$ is —$OCF_3$, —$OCHF_2$, or 1,1,2,2-tetrafluoroethoxy, and $R^3$ is hydrogen.
12) $R^3$ is hydrogen.
13) $R^4$ is —$CF_3$.
14) $R^1$ is —$OCF_3$, —$OCHF_2$, and $R^2$ is hydrogen, fluoro, chloro, cyano, trifluoromethyl, 1,1-difluoroethyl, trifluoromethoxy, difluoromethoxy, or 1,1,2,2-tetrafluoroethoxy.
15) $R^1$ is —$OCF_3$, —$OCHF_2$, and $R^2$ is trifluoromethyl, 1,1-difluoroethyl, trifluoromethoxy, difluoromethoxy, or 1,1,2,2-tetrafluoroethoxy, and $R^3$ is hydrogen.
16) $R^1$ is —$OCF_3$, —$CF_3$ or —CN; $R^2$ is hydrogen, —$OCF_3$ or —$CF_3$; $R^3$ is hydrogen; and $R^4$ is —$CF_3$.
17) $R^1$ is —$OCF_3$ or —$CF_3$; $R^2$ is hydrogen, —$OCF_3$ or —$CF_3$; $R^3$ is hydrogen; and $R^4$ is —$CF_3$.
18) $R^1$ is —$OCF_3$, —$CF_3$ or —CN; $R^2$ is —$OCF_3$ or —$CF_3$; $R^3$ is hydrogen; and $R^4$ is —$CF_3$.
19) $R^1$ is —$OCF_3$ or —$CF_3$; $R^2$ is —$OCF_3$ or —$CF_3$; $R^3$ is hydrogen; and $R^4$ is —$CF_3$.

Specific preferred compounds of the present invention are those described in the Examples herein, including the free bases and the pharmaceutically acceptable salts thereof. Of the exemplified compounds, particularly preferred compounds are 4-[(3R,5R)-3-[1-Methyl-1-(6-trifluoromethyl-pyridin-2-yl)-ethylamino]-2-oxo-5-(3-trifluoromethoxy-phenyl)-pyrrolidin-1-yl]-benzonitrile (the compound of example 27) and (3R,5R)-3-[1-Methyl-1-(6-trifluoromethyl-pyridin-2-yl)-ethylamino]-5-(3-trifluoromethyl-phenyl)-1-(4-trifluoromethoxy-phenyl)-pyrrolidin-2-one (the compound of example 28) and/or pharmaceutically acceptable salts thereof.

General Schemes

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I and (Ia) is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

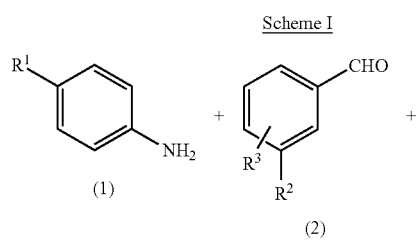

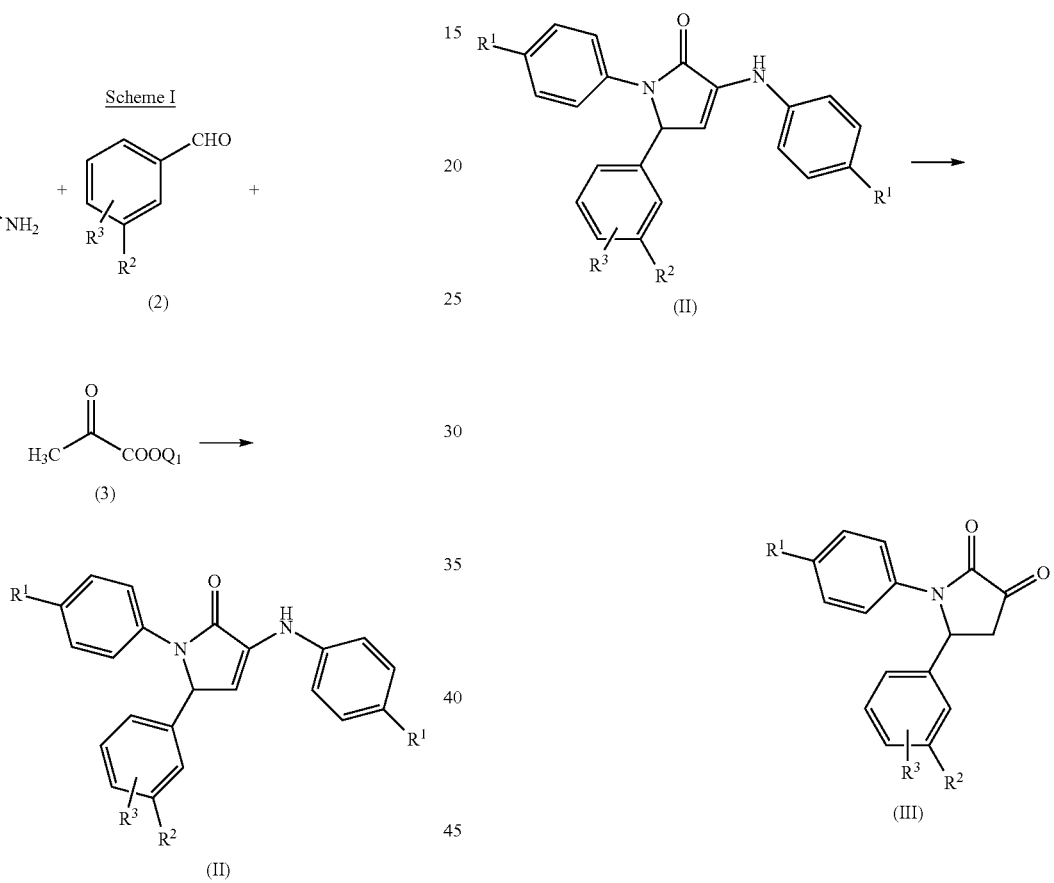

ene, pentane, isopropanol and mixtures thereof. If a precipitate is formed, the compound of Formula (II) may be isolated by filtration and vacuum drying or by filtration and chromatography. Alternatively, the compound may be isolated by concentration of the reaction and chromatography of the residue or by aqueous workup and concentration and chromatography of the organic extracts.

In Scheme I, a compound of Formula (II) may be prepared by the method described by Andreichikov and coworkers (Andreichikov, et al. Zhurnal Organicheskoi Khimii 22(10), 2208-13 (1986)), in which a mixture of an amine of Formula (I) and an aldehyde of Formula (2) is treated with an ester of pyruvic acid (3), where $Q_1$ is a $C_{1-3}$ alkyl group, in a suitable solvent such as glacial HOAc. Suitable esters of pyruvic acid include ethyl pyruvate. The reaction may proceed at temperatures between room temperature and the boiling point of the solvent. In some cases, the product (II) may precipitate during the course of the reaction or upon addition of a solvent in which the product is not highly soluble. These solvents include diethyl ether, heptane, MTBE, acetone, water, tolu- In Scheme II, a compound of formula (III) may be prepared by treatment of a compound of formula (II) with water, optionally in the presence of an acid. This reaction may also optionally be performed in the presence of an additional solvent such as HOAc, methylene chloride, tetrahydrofuran, or toluene or a mixture of solvents. Suitable acids include trifluoroacetic acid and hydrochloric acid. For example, the compound of Formula (III) can be prepared by hydrolysis with trifluoroacetic acid in a biphasic mixture with the solvents toluene and water. It is often advantageous to perform this reaction in the presence of at least one equivalent of 2,5-dimethoxytetrahydrofuran. Once the compound of formula (III) has formed, it can be isolated by adding a solvent such as toluene or isopropyl acetate or a mixture of both, and washing with water and saturated aqueous sodium bicarbonate solution. The organic layer may be dried over a desiccant such as sodium sulfate and concentrated to provide the product as a crude mixture. The extract may be used directly in the next reaction without further purification. In some cases, pouring the reaction onto ice/water allows precipitation and isolation of the compound of formula (III) through filtration.

Scheme III

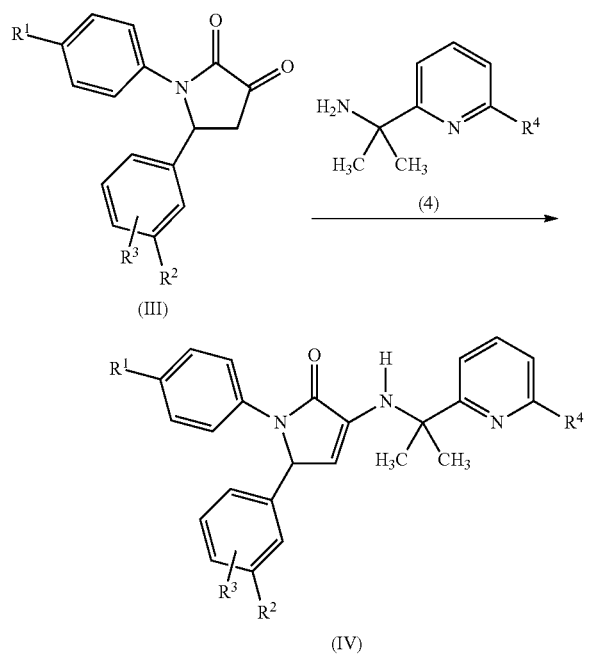

In Scheme III, a compound of Formula (IV) may be prepared by treatment of a solution of a compound of Formula (III) with a compound of Formula (4) in a suitable solvent such as dichloromethane, toluene or THF and may be performed at temperatures ranging from room temperature to around 60° C. This reaction may also be performed in the presence of a catalyst such as HOAc. The compound of Formula (IV) can be isolated, if desired, by methods known in the art such as by precipitation with a solvent such as 20% MTBE/hexanes or by silica gel chromatography.

Scheme IV

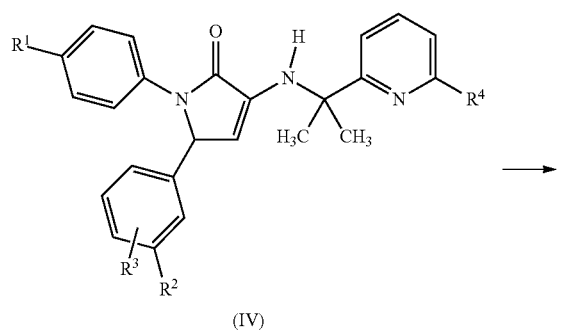

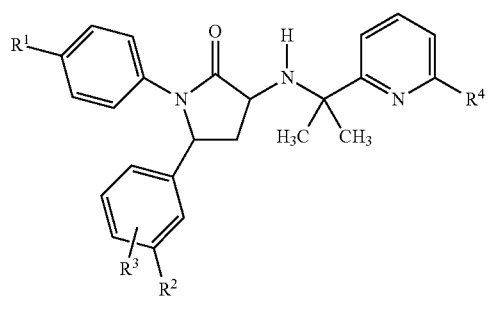

(Ia)

In Scheme IV, a compound of formula (Ia) may be formed by treatment of a compound of formula (IV) under suitable reducing conditions. Suitable reducing conditions include treatment with NaCNBH$_3$ in the presence of HOAc or treatment with Na(OAc)$_3$BH in the presence of trifluoroacetic acid in a suitable solvent such a toluene. The compound of Formula (Ia) can be isolated by means such as aqueous workup or precipitation of the product. Further purification may be performed by use of such techniques as silica gel chromatography. Purification may also be performed by treatment of mixtures containing a compound of Formula (Ia) with an acid to provide the salt of compound of Formula (Ia) which may then be purified by crystallization to provide the purified salt of the compound of Formula (Ia). Preferred salts include those formed by addition with hydrochloric acid, p-toluenesulfonic acid and adipic acid.

In the synthesis of a compound of Formula (Ia) either of the intermediates of Formula (III) or Formula (IV) may be used directly in subsequent reactions without purification of the crude intermediates.

Single enantiomers of compounds of Formula (Ia) are generally preferred over the corresponding racemates. These enantiomers may be prepared by resolution of a compound of Formula (Ia) using techniques such as preparative chromatography employing a chiral stationary phase. The enantiomers may also be prepared by resolution which comprises formation of a salt of the racemic mixture with an optically active acid and purification of the desired diastereomeric salt. The desired diastereomeric salt may be purified by crystallization. Alternatively, any of the intermediates of formula (II), (III), or (IV) may be resolved to provide substantially a single enantiomer which may then be converted using the methods described above to provide a compound of Formula (Ia) in its enantiomerically purified form as a compound of Formula (I). The intermediates of formula (II), (III), or (IV) may be prepared by resolution of compounds of the corresponding racemic compound using techniques such as preparative chromatography employing a chiral stationary phase.

Scheme V

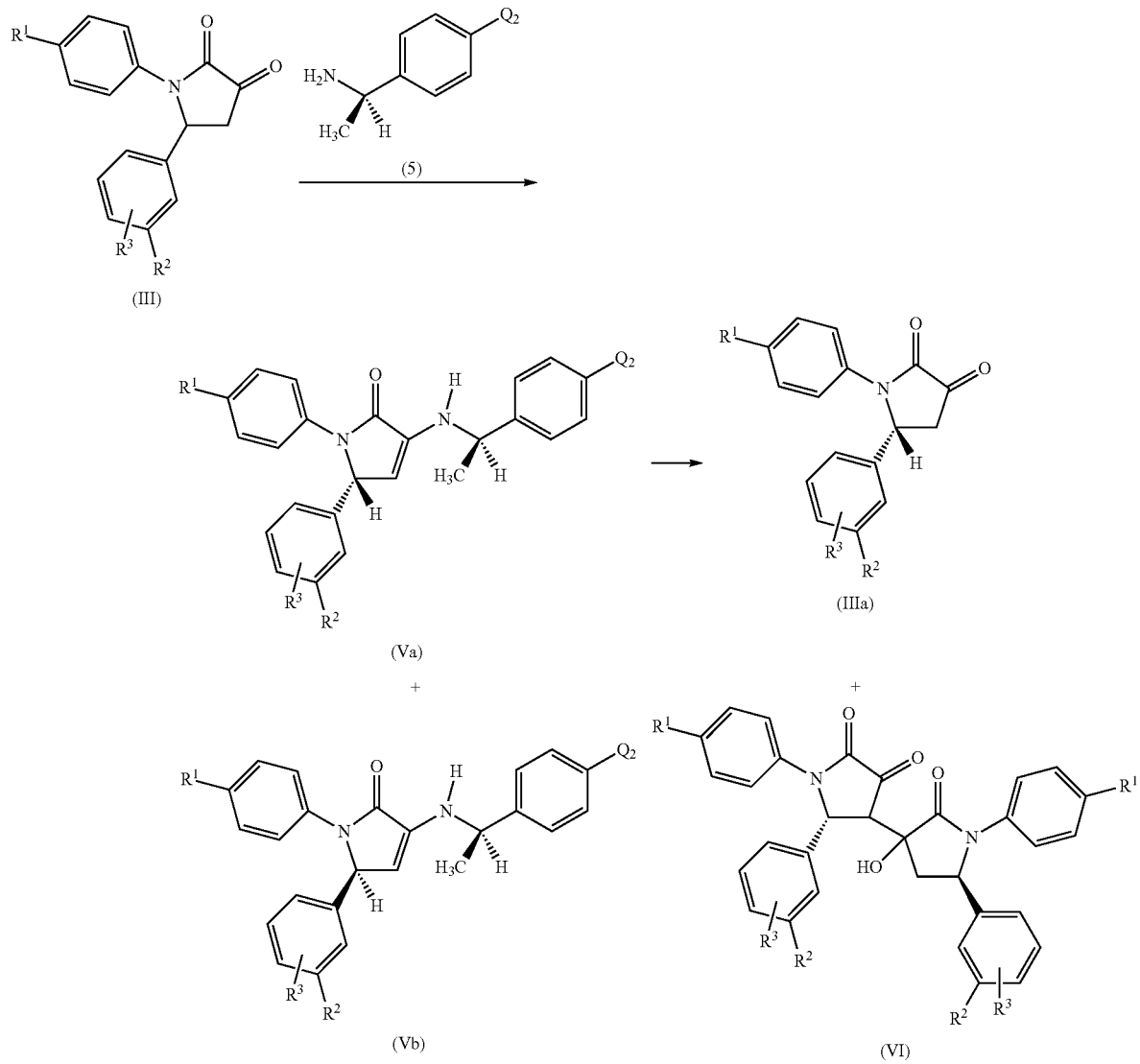

An alternative and often preferred method for the preparation of purified enantiomers of compounds of formula (III) is outlined in Scheme V. A racemic compound of formula (III) is reacted with a compound of formula (5), in which Q2 is hydrogen or halo to form a diastereomeric mixture of compounds of formula (Va) and (Vb). Preferred compounds of formula (5) include R-alpha-methylbenzylamine or S-alpha-methylbenzylamine. This condensation may be performed such as described previously in Scheme III by combining a compound of Formula (III) and compound (5) in an inert solvent such as toluene and optionally heating from room temperature to around 60° C. until the completion of the reaction. This reaction may also be performed in the presence of a catalyst such as HOAc. The diastereomers of formula (Va) and (Vb) are then separated using techniques such as silica gel chromatography or crystallization from inert solvents such as isopropanol or mixtures of solvents such as MTBE/hexanes. The desired diastereomer (designated (Va)) in Scheme V is then hydrolyzed to form the purified enantiomer of formula (IIIa). Suitable hydrolysis conditions include treating a solution of the desired diastereomer in HOAc with aqueous hydrochloric acid. In some instances, the crude (IIIa) may contain substantial amounts of the dimer of formula (VI).

In Scheme V, the racemic compound of formula (III) may be crude product resulting from the process outlined in Scheme II. In addition, the purified enantiomer (optionally containing compound of formula (VI)) of formula (IIIa) may be used directly from the hydrolysis reaction, without further purification, in the process outlined in Scheme III.

In Scheme V, the (R)-enantiomer of compound (5) was chosen to exemplify the process. One skilled in the art will recognize that the (S)-enantiomer of compound (5) may also be used in this process. The choice of whether to use the (R)- or (S)-enantiomer may be made depending on which will yield the desired diastereomer that is more readily isolated.

Scheme VI

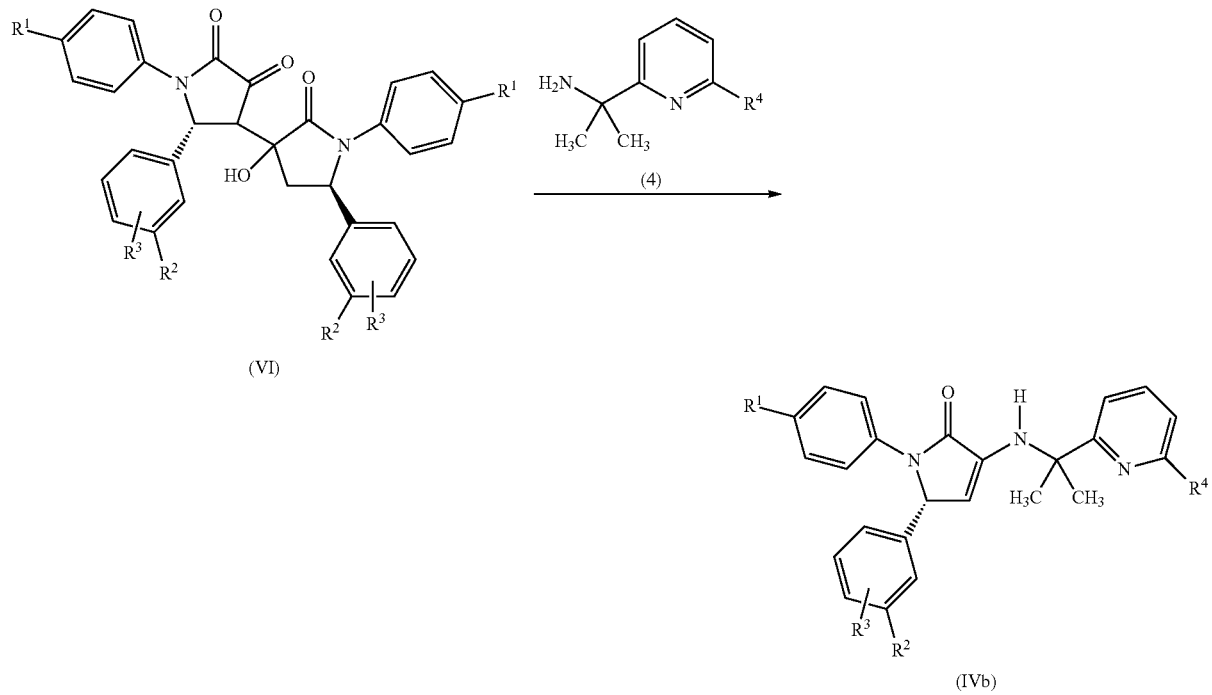

In Scheme VI, the compound of formula (IVb) may also be formed by treatment of compound of formula (VI) with compound (4) under the same conditions as described for the reaction of compound (III) with (4).

Scheme VII

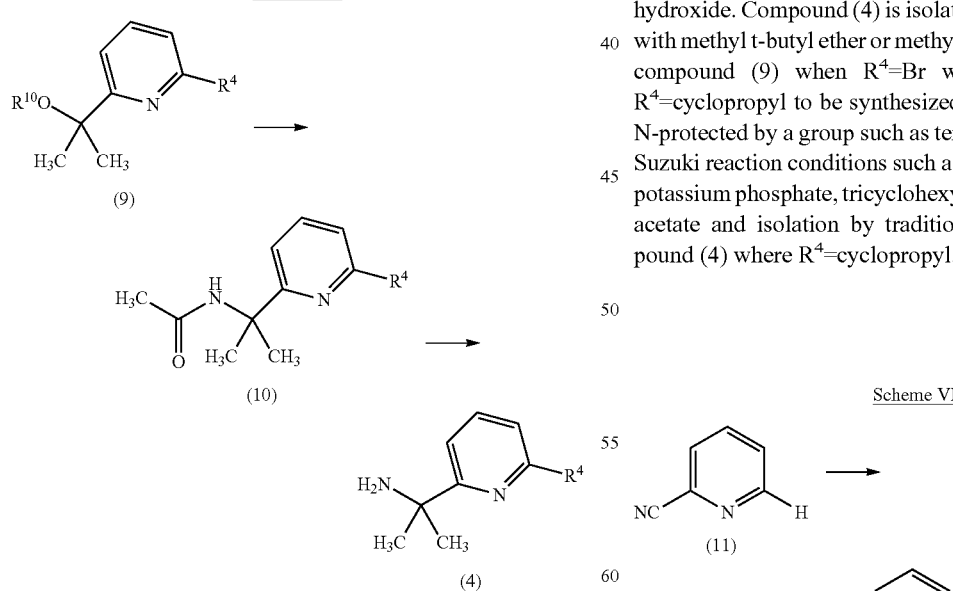

In Scheme VII, the compound (4) is prepared by treatment of a compound (9), in which $R^{10}$ is hydrogen, —$CH_3$, or —$C(O)CH_3$ with acetonitrile in the presence of acid to provide a compound of Formula (10). Suitable acids include sulfuric acid or a suitable Lewis acid such as boron trifluoride etherate. After combining the above, the reaction is heated, cooled to about 0° C. and quenched with aqueous sodium hydroxide. Compound (10) is isolated by precipitation with t-butyl methyl ether or ethanol and water. Compound (10) is heated in a solution of aqueous hydrochloric acid to approximately 90° C. The reaction is quenched with ice and sodium hydroxide. Compound (4) is isolated after several extractions with methyl t-butyl ether or methylene chloride. Starting with compound (9) when $R^4$=Br will allow compound (4) $R^4$=cyclopropyl to be synthesized. Compound (4) $R^4$=Br is N-protected by a group such as tert-butyl carbonyl and using Suzuki reaction conditions such as cyclopropyl boronic acid, potassium phosphate, tricyclohexyl phosphine and palladium acetate and isolation by traditional means provides compound (4) where $R^4$=cyclopropyl.

Scheme VIII

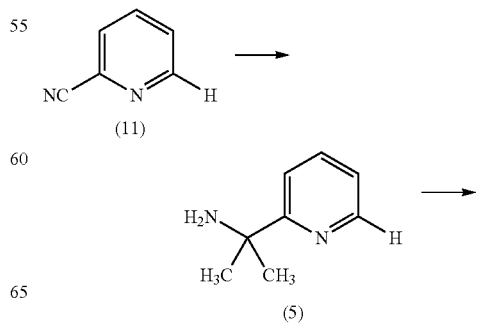

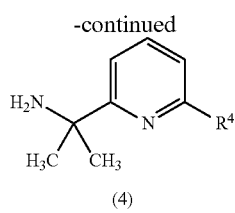

(4)

R⁴ = CN

In Scheme VIII, compound (4) is prepared from a compound of formula (11) by heating cerium (III) chloride heptahydrate to about 140° C. under vacuum to form anhydrous cerium (III) chloride and suspending in an appropriate solvent such as THF at room temperature. The reaction is cooled to −78° C. and methyllithium is added dropwise. Compound (11) in THF is added dropwise to the solution. The compound (5) is isolated by methods known in the art such as decanting the filtrate and evaporating. Compound (5) may be used without further purification such as in the synthesis of compound (4) where R⁴=CN. Compound (5) is N-protected by a group such as tert-butyl carbonyl. The N-oxide of the 2-pyridyl ring is formed by reacting with meta-chloroperoxybenzoic acid in a solvent such as methylene chloride. The resulting compound is reacted with trimethylsilyl cyanide in the presence of benzoyl chloride and isolated by traditional means to provide compound (4) where R⁴=CN.

PREPARATIONS AND EXAMPLES

Conditions for High Performance Liquid Chromatography (HPLC) Methods referred to throughout the Preparations and Examples:
Method 1
LC Column: Phenomenex® Gemini® $C_{18}$ 2.0×50 mm 3.0 μM
Gradient: 5-100% acetonitrile w/0.1% formic acid in 7.0 min. then held at 100% for 1.0 min.
Column Temp: 50° C.+/−10° C.
AS Temp: ambient
Flow Rate: 1.0 mL/min.
Signal detected at 214 and 300 nM wavelength.
Method 2
LC Column: Phenomenex® Gemini® $C_{18}$ 2.0×50 mm 3.0 μm
Gradient: 5-100% acetonitrile w/0.1% formic acid in 3.5 min. then held at 100% for 0.5 min.
Column Temp: 50° C.+/−10° C.
AS Temp: ambient
Flow Rate: 1.0 mL/min
Signal detected at 214 and 300 nM wavelength.

Preparation 1: (±)-5-(3-Trifluoromethoxy-phenyl)-1-(4-trifluoromethoxy-phenyl)-3-(4-trifluoromethoxy-phenylamino)-1,5-dihydro-pyrrol-2-one

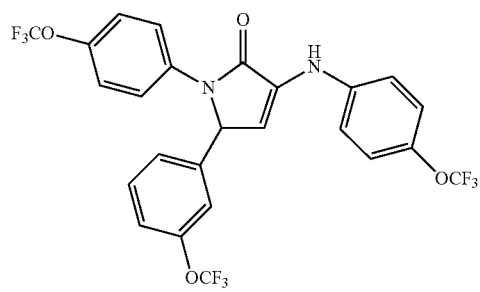 [SMILES: O=C1C(Nc2ccc(OC(F)(F)F)cc2)=CC(c2cccc(OC(F)(F)F)c2)N1c1ccc(OC(F)(F)F)cc1]

Stir 3-(trifluoromethoxy)benzaldehyde (25.2 g, 132.4 mmol), 4-(trifluoromethoxy)aniline (39.4 mL, 291 mmol) and ethyl pyruvate (14.6 mL, 132.4 mmol) in glacial HOAc (97 mL) at ambient temperature for 18 hours. Concentrate under reduced pressure and dissolve the residue in Et₂O. Let stand 18 hours at ambient temperature. Filter the precipitate and dry under vacuum to afford the titled compound (24.8 g) as a yellow crystalline solid. Purify the filtrate by silica gel chromatography (5-45% dichloromethane-hexane) to afford additional product (33.4 g, 76%). LC-MS ESI m/z: 577 (M−1)⁻, $T_r$=5.73 min., method 1.

Prepare the following compounds essentially by the method of Preparation 1.

TABLE 1

| Prep. No | Compound and Name | Yield, Physical data, and Comments |
|---|---|---|
| 2 | ![structure] (±)-5-[3-(1,1,2,2-Tetrafluoro-ethoxy)-phenyl]-1-(4-trifluoromethoxy-phenyl)-3-(4-trifluoromethoxy-phenylamino)-1,5-dihydro-pyrrol-2-one | Yield 70% LC-MS ESI m/z: 609 (M − 1)⁻, $T_r$ = 5.61 min., method 1. Use 3 equiv. of 4-(trifluoromethoxy)-aniline |

TABLE 1-continued

| Prep. No | Compound and Name | Yield, Physical data, and Comments |
|---|---|---|
| 3 | 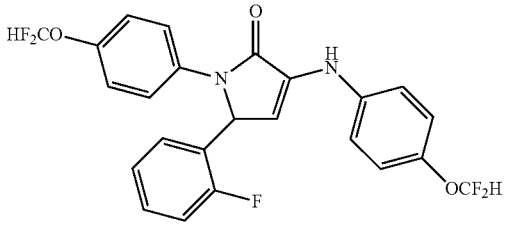<br>(±)-5-(2-Fluoro-phenyl)-1-(4-difluoromethoxy-phenyl)-3-(4-difluoromethoxy-phenylamino)-1,5-dihydro-pyrrol-2-one | Yield 37%<br>LC-MS ESI m/z: 476.8 $(M + 1)^+$, $T_r = 4.83$ min., method 1.<br>Filter product from reaction mixture and wash with 4:1 heptane:MTBE.<br>Use 3 equiv. of 4-(difluoromethoxy)-aniline |
| 4 | 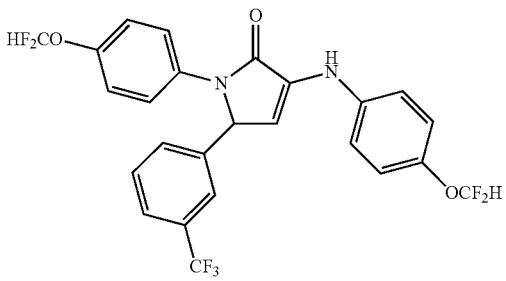<br>(±)-5-(3-Trifluoromethyl-phenyl)-1-(4-difluoromethoxy-phenyl)-3-(4-difluoromethoxy-phenylamino)-1,5-dihydro-pyrrol-2-one | Yield 43%<br>LC-MS ESI m/z: 526.6 $(M + 1)^+$, $T_r = 4.97$ min., method 1.<br>Filter product from reaction mixture and wash with 3:1 heptane:MTBE. |
| 5 | 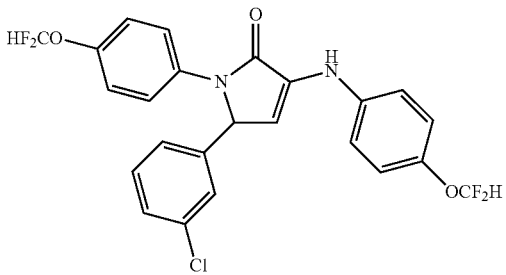<br>(±)-5-(3-Chloro-phenyl)-1-(4-difluoromethoxy-phenyl)-3-(4-difluoromethoxy-phenylamino)-1,5-dihydro-pyrrol-2-one | Yield 50%<br>LC-MS ESI m/z: ($^{35}$Cl/$^{37}$Cl) 492.8/494.6 $(M + 1)^+$, $T_r = 4.95$ min., method 1.<br>Filter product from reaction mixture and wash with 3:1 heptane:MTBE. |
| 6 | 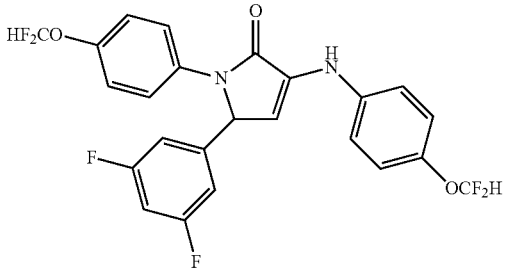<br>(±)-5-(3,5-Difluoro-phenyl)-1-(4-difluoromethoxy-phenyl)-3-(4-difluoromethoxy-phenylamino)-1,5-dihydro-pyrrol-2-one | Yield 56%<br>LC-MS ESI m/z: 494.8 $(M + 1)^+$, $T_r = 4.85$ min., method 1.<br>Filter product from reaction mixture and wash with 3:1 heptane:MTBE. |

TABLE 1-continued

| Prep. No | Compound and Name | Yield, Physical data, and Comments |
|---|---|---|
| 7 | 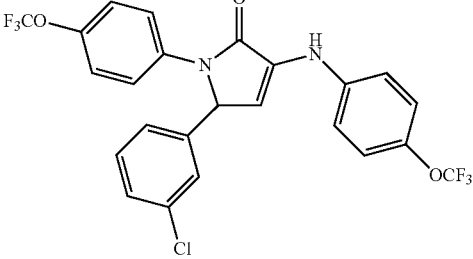<br>(±)-5-(3-Chloro-phenyl)-1-(4-trifluoromethoxy-phenyl)-3-(4-trifluoromethoxy-phenyl)-1,5-dihydro-pyrrol-2-one | Yield 69%<br>LC-MS ESI m/z: 494.8 $(M - 1)^-$, $T_r = 5.80$ min., method 1.<br>Use 3 equiv. of 4-(trifluoromethoxy)-aniline |
| 8 | 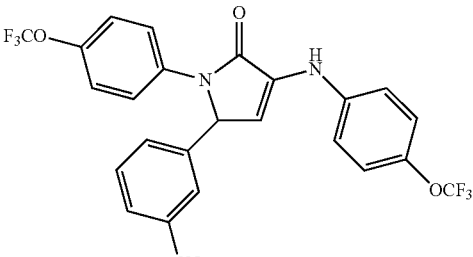<br>(±)-3-[5-Oxo-1-(4-trifluoromethoxy-phenyl)-4-(4-trifluoromethoxy-phenylamino)-2,5-dihydro-1H-pyrrol-2-yl]-benzonitrile | Yield 89%<br>LC-MS ESI m/z: 520 $(M + H)^+$, $T_r = 3.11$ min., method 2.<br>Filter product from the reaction, wash with HOAc, then 1:1 ethyl ether:hexanes. |
| 9 | 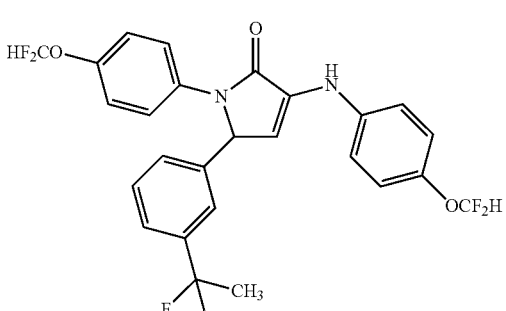<br>(±)-5-[3-(1,1-Difluoro-ethyl)-phenyl]-1-(4-difluoromethoxy-phenyl)-3-(4-difluoromethoxy-phenylamino)-1,5-dihydro-pyrrol-2-one | Yield 54%<br>LC-MS ESI m/z: 523 $(M + H)^+$, $T_r = 2.97$ min., method 2.<br>Evaporate the reaction mixture and chromatograph over silica eluting with 15% EtOAc:hexanes. |
| 10 | 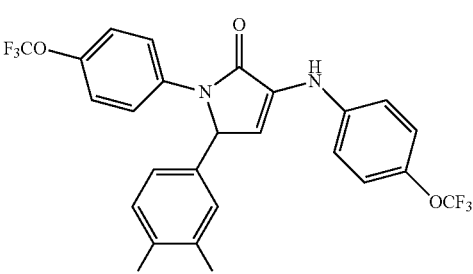<br>(±)-5-(3,4-Difluoro-phenyl)-1-(4-trifluoromethoxy-phenyl)-3-(4-trifluoromethoxy-phenylamino)-1,5-dihydro-pyrrol-2-one | Yield 48%<br>LC-MS ESI m/z: 529 $(M - 1)^-$, $T_r = 3.52$ min., method 2.<br>Filter product from reaction mixture and wash with hexanes. |

TABLE 1-continued

| Prep. No | Compound and Name | Yield, Physical data, and Comments |
|---|---|---|
| 11 | 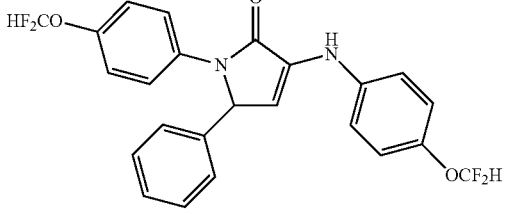<br>(±)-5-Phenyl-1-(4-difluoromethoxy-phenyl)-3-(4-difluoromethoxy-phenylamino)-1,5-dihydro-pyrrol-2-one | Yield 28%<br>LC-MS ESI m/z: 459 $(M + 1)^+$, $T_r$ = 3.16 min., method 2.<br>Chromatograph on silica gel by elution with 10-25% EtOAc/hexane. |
| 12 | 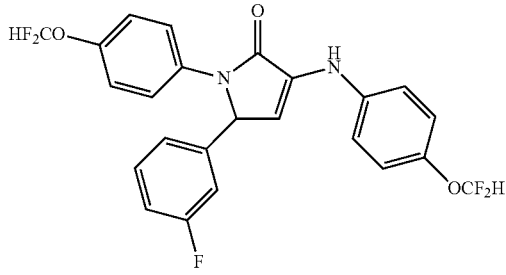<br>(±)-5-(3-Fluoro-phenyl)-1-(4-difluoromethoxy-phenyl)-3-(4-difluoromethoxy-phenylamino)-1,5-dihydro-pyrrol-2-one | Yield 37%<br>LC-MS ESI m/z: 499 $(M + Na)^+$, $T_r$ = 3.17 min., method 2.<br>Concentrate crude reaction and crystallize from cold ether then filter. |
| 13 | 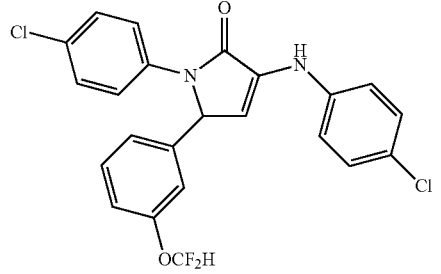<br>(±)-5-(3-Difluoromethoxy-phenyl)-1-(4-chloro-phenyl)-3-(4-chloro-phenylamino)-1,5-dihydro-pyrrol-2-one | Yield 64%<br>LC-MS ESI m/z: 461 $(M + H)^+$, $T_r$ = 3.29 min., method 2.<br>Concentrate crude reaction and crystallize from 3:1 hexane/ether then filter. |
| 14 | 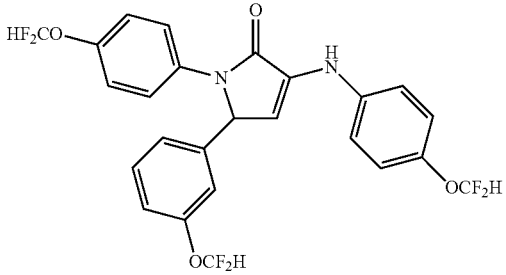<br>(±)-5-(3-Difluoromethoxy-phenyl)-1-(4-difluoromethoxy-phenyl)-3-(4-difluoromethoxy-phenylamino)-1,5-dihydro-pyrrol-2-one | Yield 51%<br>LC-MS ESI m/z: 547 $(M + Na)^+$, $T_r$ = 3.11 min., method 2.<br>Chromatograph on silica gel by elution with 10-20% EtOAc/hexane. |

TABLE 1-continued

| Prep. No | Compound and Name | Yield, Physical data, and Comments |
|---|---|---|
| 15 | 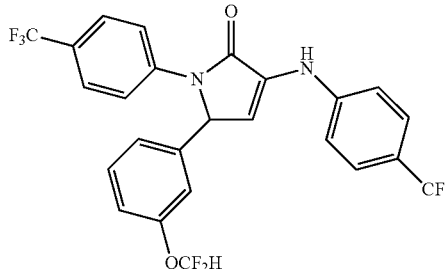<br>(±)-5-(3-Difluoromethoxy-phenyl)-1-(4-trifluoromethyl-phenyl)-3-(4-trifluoromethyl-phenylamino)-1,5-dihydro-pyrrol-2-one | Yield 76%<br>LC-MS ESI m/z: 551 $(M + Na)^+$, $T_r = 3.39$ min., method 2. Concentrate crude reaction and crystallize from 3:1 hexane/ether then filter. |
| 16 | 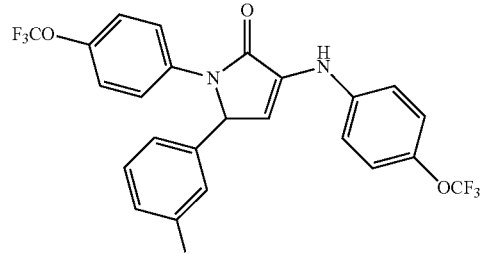<br>(±)-5-(3-Difluoromethoxy-phenyl)-1-(4-trifluoromethoxy-phenyl)-3-(4-trifluoromethoxy-phenylamino)-1,5-dihydro-pyrrol-2-one | Yield 41%<br>LC-MS ESI m/z: 583 $(M + Na)^+$, $T_r = 3.41$ min., method 2. Concentrate crude reaction and crystallize from 3:1 hexane/ether then filter. |
| 17 | 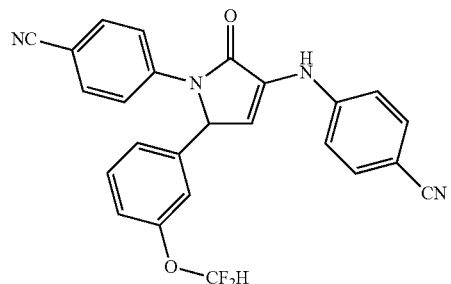<br>(±)-4-[5-(3-Difluoromethoxy-phenyl)-2-oxo-3-(4-cyano-phenylamino)-2,5-dihydro-pyrrol-1-yl]-benzonitrile | Yield 52%<br>LC-MS ESI m/z: 465 $(M + Na)^+$, $T_r = 2.85$ min., method 2. Concentrate crude reaction and crystallize from 3:3:1 dichloromethane/hexane/ether then filter. |
| 18 | 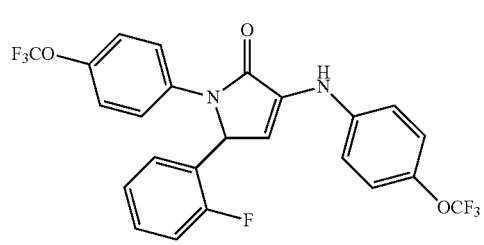<br>(±)-5-(2-Fluoro-phenyl)-1-(4-trifluoromethoxy-phenyl)-3-(4-trifluoromethoxy-phenylamino)-1,5-dihydro-pyrrol-2-one | Yield 82%<br>LC-MS ESI m/z 511 $(M - H)^-$ $T_r = 3.50$ min., method 2. Filtered product from reaction mixture and washed with hexanes |

TABLE 1-continued

| Prep. No | Compound and Name | Yield, Physical data, and Comments |
|---|---|---|
| 19 | 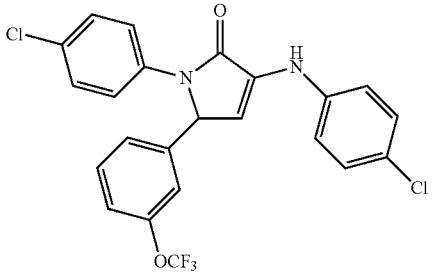<br>(±)-5-(3-Trifluoromethoxy-phenyl)-1-(4-chloro-phenyl)-3-(4-chloro-phenylamino)-1,5-dihydro-pyrrol-2-one | Yield 50%<br>LC-MS ESI m/z: 479 $(M + H)^+$, $T_r$ = 5.76 min., method 1.<br>Filter product from reaction mixture and wash with HOAc and heptane. |
| 20 | 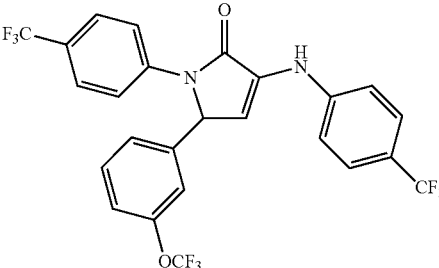<br>(±)-5-(3-Trifluoromethoxy-phenyl)-1-(4-trifluoromethyl-phenyl)-3-(4-trifluoromethyl-phenylamino)-1,5-dihydro-pyrrol-2-one | Yield 75%<br>LC-MS ESI m/z: 545 $(M - H)^-$, $T_r$ = 5.60 min., method 1.<br>Stir reaction at 50° C. for 1 hour then at ambient temperature for 18 hours.<br>Filter product from reaction mixture and wash with 4:1 heptane:MTBE. |
| 21 | 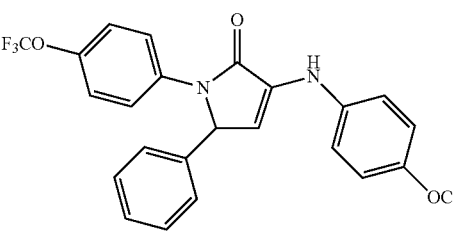<br>(±)-5-Phenyl-1-(4-trifluoromethoxy-phenyl)-3-(4-trifluoromethoxy-phenylamino)-1,5-dihydro-pyrrol-2-one | Yield 71%<br>LC-MS ESI m/z: 493 $(M - 1)$, $T_r$ = 3.23 min., method 2.<br>Concentrate reaction and triturate residue with $Et_2O$/hexanes (1:1) to isolate product. |
| 22 | 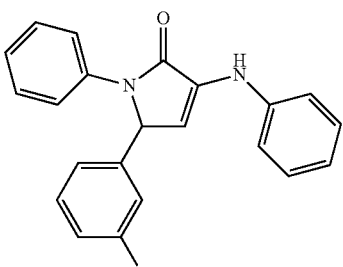<br>(±)-5-(3-Trifluoromethoxy-phenyl)-1-phenyl-3-phenylamino-1,5-dihydro-pyrrol-2-one | Yield 32%<br>LC-MS ESI m/z: 411 $(M + H)^+$, $T_r$ = 4.99 min., method 1. |

TABLE 1-continued

| Prep. No | Compound and Name | Yield, Physical data, and Comments |
|---|---|---|
| 23 | 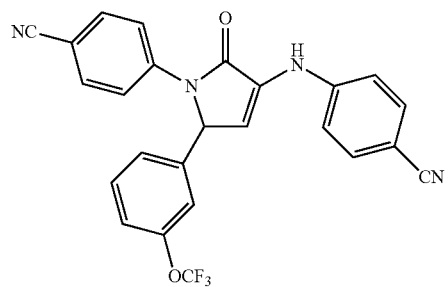 [SMILES: N#Cc1ccc(NC2=CC(c3cccc(OC(F)(F)F)c3)N(c3ccc(C#N)cc3)C2=O)cc1]<br>(±)-5-(3-Methoxy-phenyl)-1-(4-trifluoromethyl-phenyl)-3-(4-trifluoromethyl-phenylamino)-1,5-dihydro-pyrrol-2-one | Yield 85%<br>LC-MS ESI m/z: 491 (M − H)⁻, $T_r$ = 5.44 min., method 1.<br>Filter product from reaction mixture and wash with 4:1 heptane:MTBE. |

Preparation 24: (±)-4-[5-(3-Trifluoromethoxy-phenyl)-2-oxo-3-(4-cyano-phenylamino)-2,5-dihydro-pyrrol-1-yl]-benzonitrile

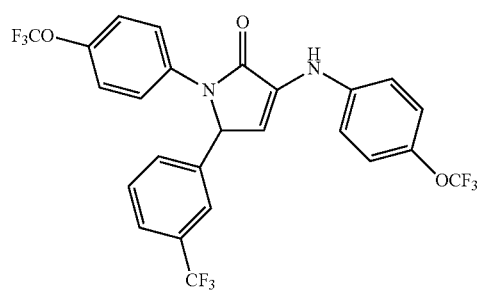 [SMILES: O=C1C(Nc2ccc(OC(F)(F)F)cc2)=CC(c2cccc(C(F)(F)F)c2)N1c1ccc(OC(F)(F)F)cc1]

Add 3-(trifluoromethoxy)benzaldehyde (10.0 g, 52.6 mmol) to a solution of 4-aminobenzonitrile (18.6 g, 157.8 mmol) in glacial acetic acid (53 mL). Stir at ambient temperature for 20 min. and a precipitate forms. Add ethyl pyruvate (5.8 mL, 52.6 mmol). Stir at ambient temperature for 18 hours. Filter the precipitate and wash with glacial acetic acid and then with 1:1 hexanes-diethyl ether to afford the titled compound (12.8 g, 53%). LC-MS ESI m/z: 461 (M+H)⁺, 459 (M−1)⁻, $T_r$=3.05 min., method 2.

Preparation 25: (±) 5-(3-Trifluoromethyl-phenyl)-1-(4-trifluoromethoxy-phenyl)-3-(4-trifluoromethoxy-phenylamino)-1,5-dihydro-pyrrol-2-one Add of 4-trifluoromethoxyaniline (6.76 mL, 50.0 mmol) to a solution of 3-(trifluoromethyl)benzaldehyde (2.7 mL, 20.0 mmol) in glacial acetic acid (53 mL). Add ethyl pyruvate (2.2 mL, 20.0 mmol). Stir at ambient temperature for 6 hours. Filter the precipitate and wash with hexanes to afford the titled compound (8.22 g, 73%). LC-MS ESI m/z 561(M–H)⁻, $T_r$=3.56 min., method 2.

Preparation 26: 1-(4-Trifluoromethoxy-phenyl)-3-(R)-1-phenyl-ethylamino)-5(S)-(3-trifluoromethoxy-phenyl)-1,5-dihydro-pyrrol-2-one

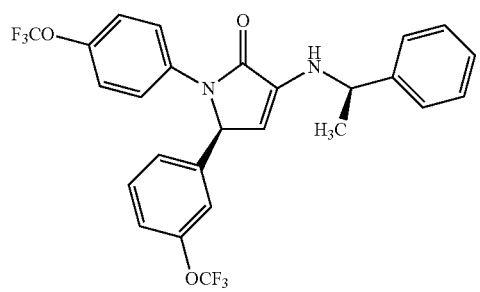

and 1-(4-Trifluoromethoxy-phenyl)-3-((R)-1-phenyl-ethylamino)-5(R)-(3-trifluoromethoxy-phenyl)-1,5-dihydro-pyrrol-2-one

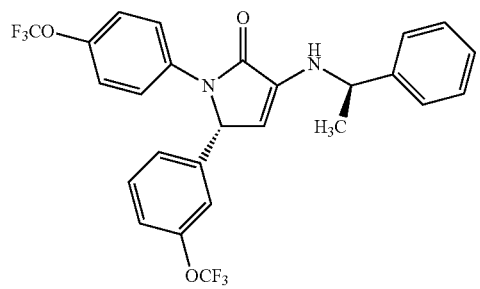 [SMILES: C[C@@H](NC1=C[C@H](c2cccc(OC(F)(F)F)c2)N(c2ccc(OC(F)(F)F)cc2)C1=O)c1ccccc1]

Add HOAc (11.5 mL, 201 mmol), 2,5-dimethoxytetrahydrofuran (9.8 mL, 75.5 mmol), water (56 mL), and trifluoroacetic acid (7.6 mL, 100.6 mmol) sequentially to a solution of (±)-5-(3-trifluoromethoxy-phenyl)-1-(4-trifluoromethoxyphenyl)-3-(4-trifluoromethoxy-phenylamino)-1,5-dihydro-pyrrol-2-one (29.1 g, 50.3 mmol) in THF (180 mL). Heat the reaction mixture to 35° C. for 22 hours. Observe significant formation of (±)-1-(4-trifluoromethoxy-phenyl)-5-(3-trifluoromethoxy-phenyl)-pyrrolidine-2,3-dione (LC-MS ESI m/z: 420 (M+H)$^+$, T$_r$=4.23 min., method 1). Cool the reaction mixture to room temperature and add toluene (200 mL) in a single portion. Wash the mixture with water and then pH 9 buffer. Separate layers and observe that the aqueous layer is pH=7. Filter through sodium sulfate and add (R)-(+)-α-methyl benzylamine (12.9 mL, 100.6 mmol). Stir the solution at ambient temperature for 18 hours. Concentrate the reaction mixture and purify by silica gel chromatography (5-15% EtOAc-hexane) to yield 1-(4-trifluoromethoxy-phenyl)-3-(R)-1-phenyl-ethylamino)-5(S)-(3-trifluoromethoxy-phenyl)-1,5-dihydro-pyrrol-2-one (9.01 g, 34%) as a yellow oil, LC-MS ESI m/z: 523 (M+H)$^+$, T$_r$=5.57 min., method 1 and 1-(4-trifluoromethoxy-phenyl)-3-(R)-1-phenyl-ethylamino)-5(R)-(3-trifluoromethoxy-phenyl)-1,5-dihydro-pyrrol-2-one (11.1 g, 42%) as an orange solid, LC-MS ESI m/z: 523 (M+H)$^+$, T$_r$=5.49 min., method 1.

Prepare the following compounds essentially by the method of Preparation 26.

TABLE 2

| Prep. No. | Compound, Name, Physical Data, Yield and Comment |
|---|---|
| 27 | 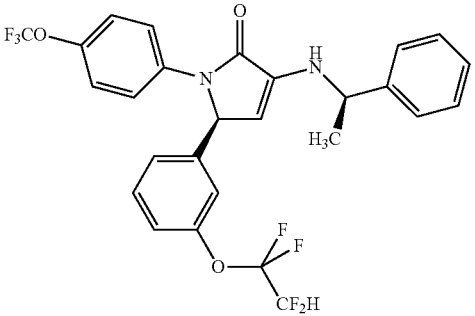 [SMILES: C[C@@H](NC1=C[C@@H](c2cccc(OC(F)(F)C(F)F)c2)N(c2ccc(OC(F)(F)F)cc2)C1=O)c1ccccc1]<br>1-(4-Trifluoromethoxy-phenyl)-3-((R)-1-phenyl-ethylamino)-5(S)-[3-(1,1,2,2-tetrafluoro-ethoxy)-phenyl]-1,5-dihydro-pyrrol-2-one<br>LC-MS ESI m/z: 555 (M + H)$^+$, T$_r$ = 5.43 min., method 1. Yield 34%.<br>and |
| 28 | 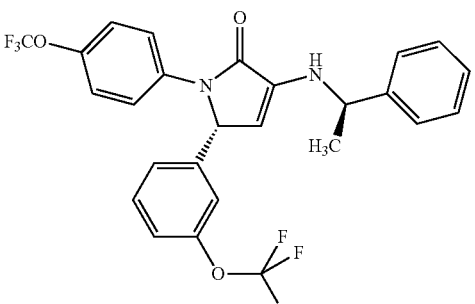<br>1-(4-Trifluoromethoxy-phenyl)-3-((R)-1-phenyl-ethylamino)-5 (R)-[3-(1,1,2,2-tetrafluoro-ethoxy)-phenyl]-1,5-dihydro-pyrrol-2-one<br>LC-MS ESI m/z: 555 (M + H)$^+$, T$_r$ = 5.35 min., method 1. Yield 42%.<br>Comment: Purify by silica gel chromatography (5-20% EtOAc-hexane) to yield both diastereomers. |
| 29 | 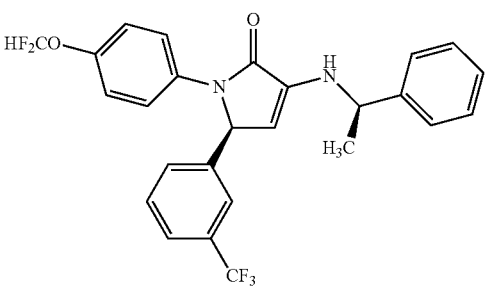<br>1-(4-Difluoromethoxy-phenyl)-3-((R)-1-phenyl-ethylamino)-5(S)-(3-trifluoromethyl-phenyl)-1,5-dihydro-pyrrol-2-one<br>LC-MS ESI m/z: 488.8 (M + H)$^+$, T$_r$ = 5.18 min., method 1. Yield 33%.<br>and |

TABLE 2-continued

| Prep. No. | Compound, Name, Physical Data, Yield and Comment |
|---|---|
| 30 | 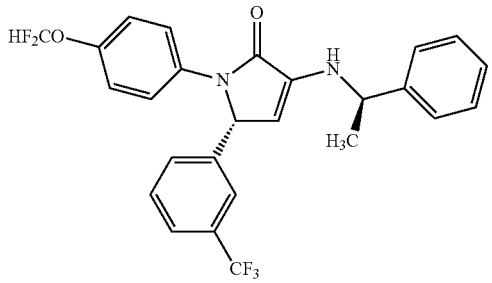<br>1-(4-Difluoromethoxy-phenyl)-3-((R)-1-phenyl-ethylamino)-5(R)-(3-trifluoromethyl-phenyl)-1,5-dihydro-pyrrol-2-one<br>LC-MS ESI m/z: 488.8 (M + H)$^+$, T$_r$ = 5.10 min., method 1. Yield 35%.<br>Comment: Purify by silica gel chromatography (10-25% EtOAc-hexane) to yield both diastereomers. |
| 31 | 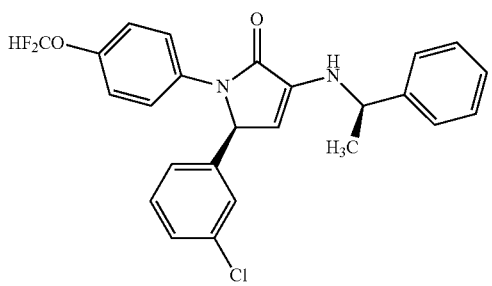<br>1-(4-Difluoromethoxy-phenyl)-3-((R)-1-phenyl-ethylamino)-5(S)-(3-chloro-phenyl)-1,5-dihydro-pyrrol-2-one<br>LC-MS ESI m/z: ($^{35}$Cl/$^{37}$Cl) 455.0/457.0 (M + H)$^+$, T$_r$ = 5.17 min., method 1.<br>Yield 36%.<br>and |
| 32 | 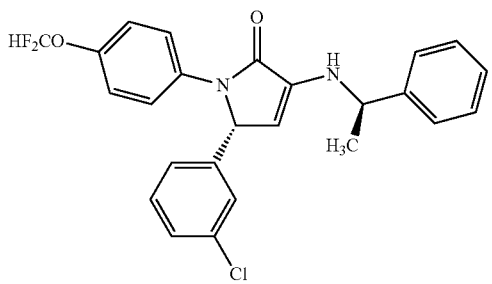<br>1-(4-Difluoromethoxy-phenyl)-3-((R)-1-phenyl-ethylamino)-5(R)-(3-chloro-phenyl)-1,5-dihydro-pyrrol-2-one<br>LC-MS ESI m/z: ($^{35}$Cl/$^{37}$Cl) 454.7/456.7 (M + H)$^+$, T$_r$ = 5.06 min., method 1.<br>Yield 33%.<br>Comment: Purify by silica gel chromatography (10-20% EtOAc-hexane) to yield both diastereomers. |

TABLE 2-continued

| Prep. No. | Compound, Name, Physical Data, Yield and Comment |
|---|---|
| 33 | 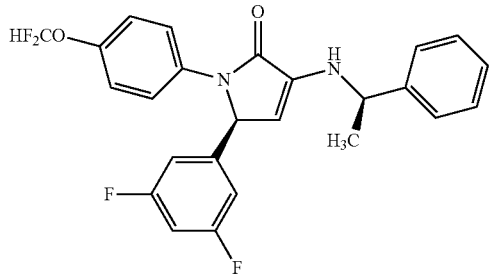<br>1-(4-Difluoromethoxy-phenyl)-3-((R)-1-phenyl-ethylamino)-5(S)-(3,5-difluoro-phenyl)-1,5-dihydro-pyrrol-2-one<br>LC-MS ESI m/z: 456.8 (M + H)⁺, $T_r$ = 5.04 min., method 1. Yield 36%.<br>and |
| 34 | 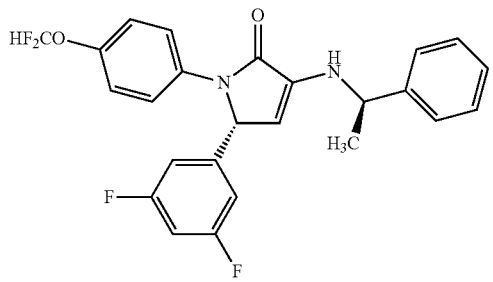<br>1-(4-Difluoromethoxy-phenyl)-3-((R)-1-phenyl-ethylamino)-5(R)-(3,5-difluoro-phenyl)-1,5-dihydro-pyrrol-2-one<br>LC-MS ESI m/z: 457.0 (M + H)⁺, $T_r$ = 4.94 min., method 1. Yield 39%.<br>Comment: Purify by silica gel chromatography (10-20% EtOAc-hexane) to yield both diastereomers. |
| 35 | 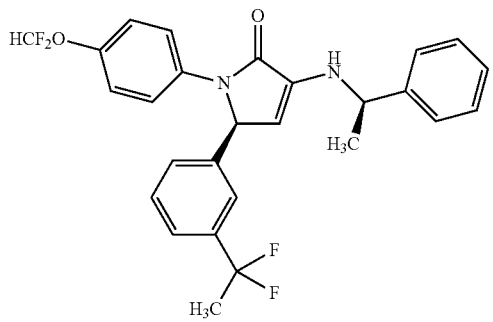<br>1-(4-Difluoromethoxy-phenyl)-3-((R)-1-phenyl-ethylamino)-5(S)-[3-(1,1-difluoro-ethyl)-phenyl]-1,5-dihydro-pyrrol-2-one<br>LC-MS ESI m/z: 485 (M + H)⁺, $T_r$ = 3.026 min., method 2. Yield 24%.<br>and |

TABLE 2-continued

| Prep. No. | Compound, Name, Physical Data, Yield and Comment |
|---|---|
| 36 | 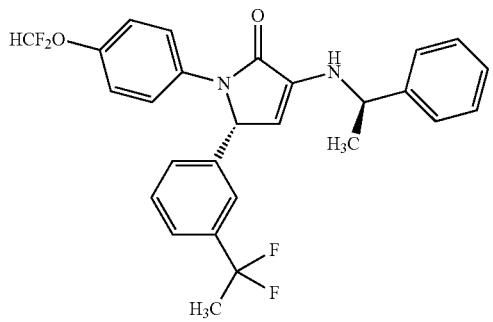

1-(4-Difluoromethoxy-phenyl)-3-((R)-1-phenyl-ethylamino)-5(R)-[3-(1,1-difluoro-ethyl)-phenyl]-1,5-dihydro-pyrrol-2-one
LC-MS ESI m/z: 458 (M + H)$^+$, T$_r$ = 2.989 min., method 2. Yield 27%.
Comment: Purify by silica gel chromatography (15% EtOAc-hexane) to yield both diastereomers. |
| 37 | 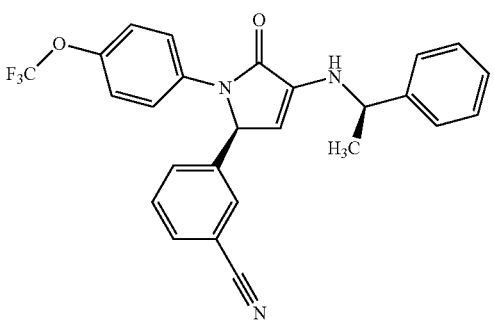 [SMILES: C[C@@H](NC1=C[C@@H](c2cccc(C#N)c2)N(c2ccc(OC(F)(F)F)cc2)C1=O)c1ccccc1]

3-[(S)-5-Oxo-4-((R)-1-phenyl-ethylamino)-1-(4-trifluoromethoxy-phenyl)-2,5-dihydro-1H-pyrrol-2-yl]-benzonitrile
LC-MS ESI m/z: 464 (M + H)$^+$, T$_r$ = 4.953 min., method 1. Yield 16%
and |
| 38 | 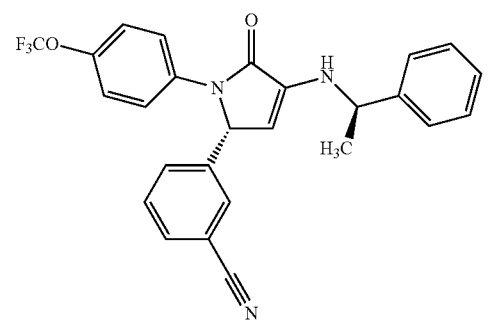 [SMILES: C[C@@H](NC1=C[C@H](c2cccc(C#N)c2)N(c2ccc(OC(F)(F)F)cc2)C1=O)c1ccccc1]

3-[(R)-5-Oxo-4-((R)-1-phenyl-ethylamino)-1-(4-trifluoromethoxy-phenyl)-2,5-dihydro-1H-pyrrol-2-yl]-benzonitrile
LC-MS ESI m/z: 464 (M + H)$^+$, T$_r$ = 4.874 min., method 1. Yield 16%.
Comment: Purify by silica gel chromatography (20% EtOAc-hexane) to yield both diastereomers. |

TABLE 2-continued

| Prep. No. | Compound, Name, Physical Data, Yield and Comment |
|---|---|
| 39 | 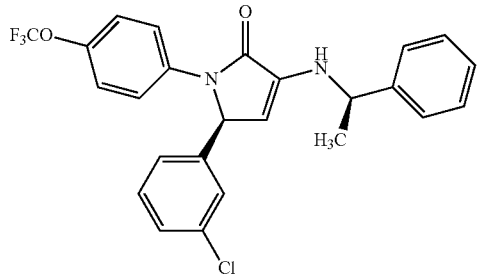 [SMILES: C[C@@H](NC1=C[C@@H](c2cccc(Cl)c2)N(c2ccc(OC(F)(F)F)cc2)C1=O)c1ccccc1]<br>1-(4-Trifluoromethoxy-phenyl)-3-((R)-1-phenyl-ethylamino)-5(S)-(3-chloro-phenyl)-1,5-dihydro-pyrrol-2-one<br>LC-MS ESI m/z: 473 (M + H)$^+$, 471 (M − H)$^-$, T$_r$ = 5.60 min., method 1. Yield 34%.<br>and |
| 40 | 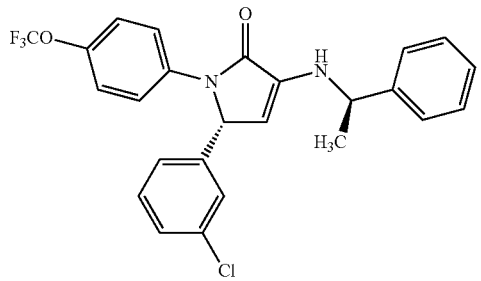 [SMILES: C[C@@H](NC1=C[C@H](c2cccc(Cl)c2)N(c2ccc(OC(F)(F)F)cc2)C1=O)c1ccccc1]<br>1-(4-Trifluoromethoxy-phenyl)-3-((R)-1-phenyl-ethylamino)-5(R)-(3-chloro-phenyl)-1,5-dihydro-pyrrol-2-one<br>LC-MS ESI m/z: 473 (M + H)$^+$, 471 (M − H)$^-$, T$_r$ = 5.48 min., method 1. Yield 32%.<br>Comment: Purify by silica gel chromatography (0-15% EtOAc-hexane) to yield both diastereomers. |
| 41 | 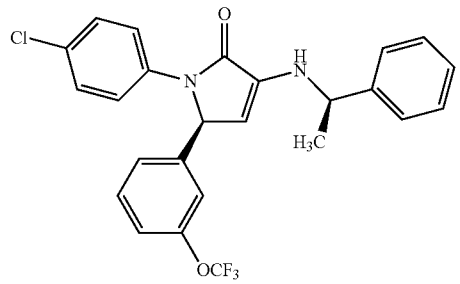 [SMILES: C[C@@H](NC1=C[C@@H](c2cccc(OC(F)(F)F)c2)N(c2ccc(Cl)cc2)C1=O)c1ccccc1]<br>1-(4-Chloro-phenyl)-3-((R)-1-phenyl-ethylamino)-5(S)-(3-trifluoromethoxy-phenyl)-1,5-dihydro-pyrrol-2-one<br>LC-MS ESI m/z: 473 (M + H)$^+$, T$_r$ = 5.54 min., method 1. Yield 38%.<br>and |

TABLE 2-continued

| Prep. No. | Compound, Name, Physical Data, Yield and Comment |
|---|---|
| 42 | 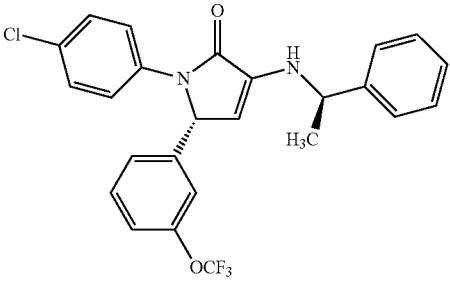 [SMILES: C[C@@H](NC1=C[C@H](c2cccc(OC(F)(F)F)c2)N(c2ccc(Cl)cc2)C1=O)c1ccccc1]<br>1-(4-Chloro-phenyl)-3-((R)-1-phenyl-ethylamino)-5(R)-(3-trifluoromethoxy-phenyl)-1,5-dihydro-pyrrol-2-one<br>LC-MS ESI m/z: 473 (M + H)$^+$, T$_r$ = 5.46 min., method 1. Yield 43%.<br>Comment: Purify by silica gel chromatography (0-10% EtOAc-hexane) to yield both diastereomers. |
| 43 | 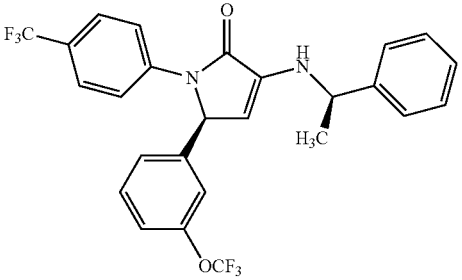 [SMILES: C[C@@H](NC1=C[C@@H](c2cccc(OC(F)(F)F)c2)N(c2ccc(C(F)(F)F)cc2)C1=O)c1ccccc1]<br>1-(4-Trifluoromethyl-phenyl)-3-((R)-1-phenyl-ethylamino)-5(S)-(3-trifluoromethoxy-phenyl)-1,5-dihydro-pyrrol-2-one<br>LC-MS ESI m/z: 507 (M + H)$^+$, 505 (M − H)$^-$, T$_r$ = 2.83 min., method 1. Yield 37%.<br>and |
| 44 | 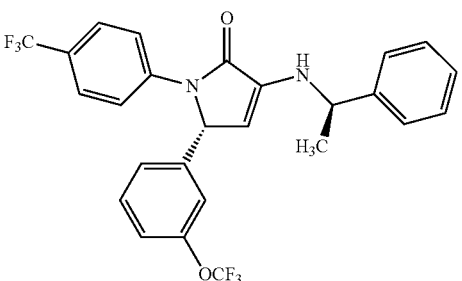<br>1-(4-Trifluoromethyl-phenyl)-3-((R)-1-phenyl-ethylamino)-5(R)-(3-trifluoromethoxy-phenyl)-1,5-dihydro-pyrrol-2-one<br>LC-MS ESI m/z: 507 (M + H)$^+$, 505 (M − H)$^-$, T$_r$ = 2.66 min., method 1. Yield 38%. |
| 45 | 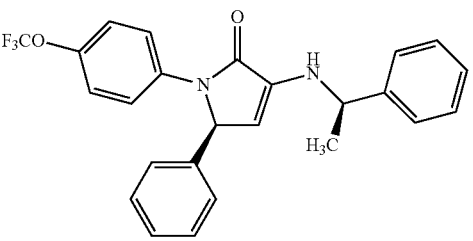 [SMILES: C[C@@H](NC1=C[C@@H](c2ccccc2)N(c2ccc(OC(F)(F)F)cc2)C1=O)c1ccccc1]<br>1-(4-Trifluoromethoxy-phenyl)-3-((R)-1-phenyl-ethylamino)-5(S)-phenyl-1,5-dihydro-pyrrol-2-one<br>LC-MS ESI m/z: 439 (M + H)$^+$, T$_r$ = 5.30 min., method 1. Yield 32%.<br>and |

TABLE 2-continued

| Prep. No. | Compound, Name, Physical Data, Yield and Comment |
|---|---|
| 46 | 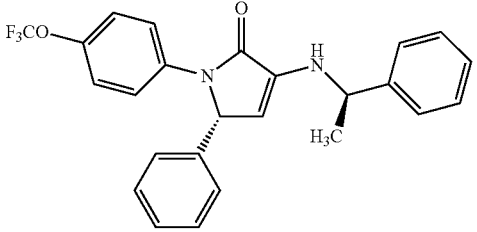 [SMILES: C[C@@H](NC1=C[C@H](c2ccccc2)N(c2ccc(OC(F)(F)F)cc2)C1=O)c1ccccc1]<br>1-(4-Trifluoromethoxy-phenyl)-3-((R)-1-phenyl-ethylamino)-5(R)-phenyl-1,5-dihydro-pyrrol-2-one<br>LC-MS ESI m/z: 439 (M + H)⁺, $T_r$ = 5.21 min., method 1. Yield 27%.<br>Comment: Purify by silica gel chromatography (5-25% EtOAc-hexane) to yield both diastereomers. |
| 47 | 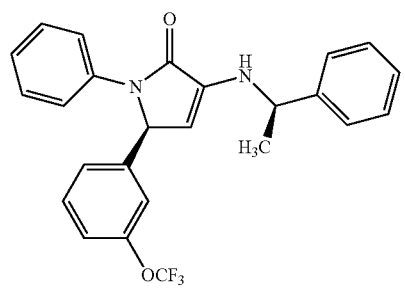 [SMILES: C[C@@H](NC1=C[C@@H](c2cccc(OC(F)(F)F)c2)N(c2ccccc2)C1=O)c1ccccc1]<br>1-Phenyl-3-((R)-1-phenyl-ethylamino)-5(S)-(3-trifluoromethoxy-phenyl)-1,5-dihydro-pyrrol-2-one<br>¹H NMR (400 MHz, DMSO-$d_6$) δ 7.47 (d, J = 7.9 Hz, 2H), 7.38-7.31 (m, 3H), 7.31-7.16 (m, 5H), 7.15-7.10 (m, 3H), 7.01 (dd, J = 7.5, 7.5 Hz, 1H), 5.91 (d, J = 7.0 Hz, 1H), 5.81 (d, J = 1.8 Hz, 1H), 5.14 (d, J = 1.8 Hz, 1H), 4.30-4.21 (m, 1H), 1.41 (d, J = 7.0 Hz, 3H).<br>LC-MS ESI m/z: 439 (M + H)⁺, $T_r$ = 5.15 min., method 1. Yield 32%.<br>and |
| 48 | 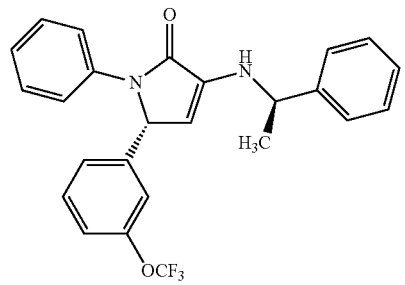 [SMILES: C[C@@H](NC1=C[C@H](c2cccc(OC(F)(F)F)c2)N(c2ccccc2)C1=O)c1ccccc1]<br>1-Phenyl-3-((R)-1-phenyl-ethylamino)-5(R)-(3-trifluoromethoxy-phenyl)-1,5-dihydro-pyrrol-2-one<br>¹H NMR (400 MHz, DMSO-$d_6$) δ 7.47 (dd, J = 8.8, 0.9 Hz, 2H), 7.33 (dd, J = 8.0, 1.0 Hz, 2H), 7.27-7.20 (m, 5H), 7.14-7.09 (m, 1H), 7.07-6.96 (m, 3H), 6.89 (s, 1H), 5.86-5.81 (m, 2H), 5.11 (d, J = 2.2 Hz, 1H), 4.30 (ddd, J = 13.8, 6.9, 6.9 Hz, 1H), 1.43 (d, J = 6.6 Hz, 3H).<br>LC-MS ESI m/z: 439 (M + H)⁺, $T_r$ = 5.05 min., method 1. Crude MS from reaction. Yield 33%.<br>Comment: Purify by silica gel chromatography (5-25% EtOAc-hexane) to yield both diastereomers. |

TABLE 2-continued

| Prep. No. | Compound, Name, Physical Data, Yield and Comment |
|---|---|
| 49 | 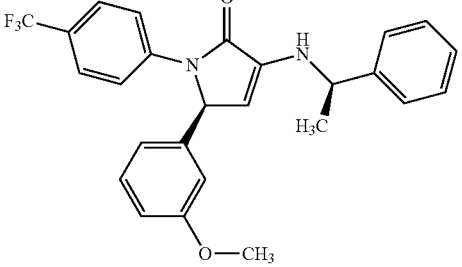<br>1-(4-Trifluoromethyl-phenyl)-3-((R)-1-phenyl-ethylamino)-5(S)-(3-methoxy-phenyl)-1,5-dihydro-pyrrol-2-one<br>LC-MS ESI m/z: 453 (M + H)⁺, T$_r$ = 5.26 min., method 1 Yield 34%.<br>and |
| 50 | 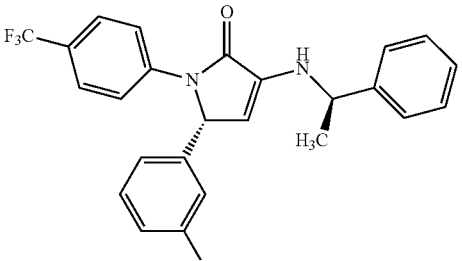<br>1-(4-Trifluoromethyl-phenyl)-3-((R)-1-phenyl-ethylamino)-5(R)-(3-methoxy-phenyl)-1,5-dihydro-pyrrol-2-one<br>LC-MS ESI m/z: 453 (M + H)⁺, T$_r$ = 5.17 min., method 1. Yield 34%. |

Preparation 51: 4-[(S)-2-oxo-3-((R)-1-phenyl-ethylamino)-5-(3-trifluoromethoxy-phenyl)-2,5-dihydro-pyrrol-1-yl]-benzonitrile

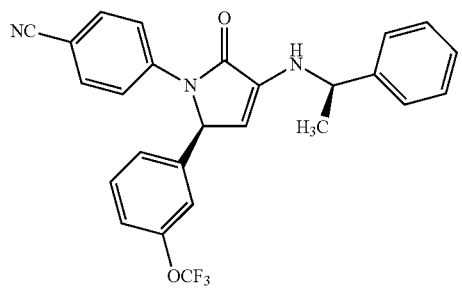

and

Preparation 52: 4-[(R)-2-oxo-3-((R)-1-phenyl-ethylamino)-5-(3-trifluoromethoxy-phenyl)-2,5-dihydro-pyrrol-1-yl]-benzonitrile

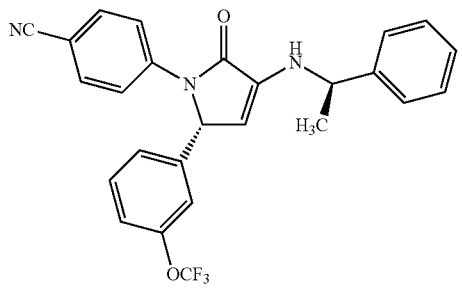 [SMILES: C[C@@H](NC1=C[C@H](c2cccc(OC(F)(F)F)c2)N(c2ccc(C#N)cc2)C1=O)c1ccccc1]

Add acetic acid (6.32 mL, 110 mmol), 2,5-dimethoxytetrahydrofuran (10.7 mL, 82.8 mmol), water (25 mL), and trifluoroacetic acid (4.2 mL, 55.2 mmol) sequentially to a mixture of (±)-4-[5-(3-trifluoromethoxy-phenyl)-2-oxo-3-(4-cyano-phenylamino)-2,5-dihydro-pyrrol-1-yl]-benzonitrile (12.7 g, 27.6 mmol) and THF (83 mL). Heat the reaction mixture to 40° C. for 18 hours. Observe significant formation of (±)-4-[2,3-dioxo-5-(3-trifluoromethoxy-phenyl)-pyrrolidin-1-yl]-benzonitrile (LC-MS ESI m/z: 361 (M+H)+, T$_r$=2.34 min., method 2). Cool the reaction mixture to room temperature and add toluene (150 mL) in a single portion. Wash the mixture with water and then with brine. Dry over sodium sulfate, filter and add (R)-(+)-α-methyl benzylamine (7.1 mL, 55.2 mmol). Stir the solution at 45° C. for 1.75 hours. Concentrate the reaction mixture and purify by silica gel chromatography (15% EtOAc-hexane) to yield 4-[(S)-2-oxo-3-((R)-1-phenyl-ethylamino)-5-(3-trifluoromethoxy-phenyl)-2,5-dihydro-pyrrol-1-yl]-benzonitrile (3.34 g, 26%) as a red oil, LC-MS ESI m/z: 464 (M+H)+, T$_r$=3.09 min., method 2 and 4-[(R)-2-oxo-3-((R)-1-phenyl-ethylamino)-5-(3-trifluoromethoxy-phenyl)-2,5-dihydro-pyrrol-1-yl]-benzonitrile (4.05 g, 32%) as a foam, LC-MS ESI m/z: 464 (M+H)+, T$_r$=3.04 min., method 2.

Preparation 53: (±)-3-[1-Methyl-1-(6-trifluoromethyl-pyridin-2-yl)-ethylamino]-1-(4-difluoromethoxy-phenyl)-5-(2-fluoro-phenyl)-1,5-dihydro-pyrrol-2-one

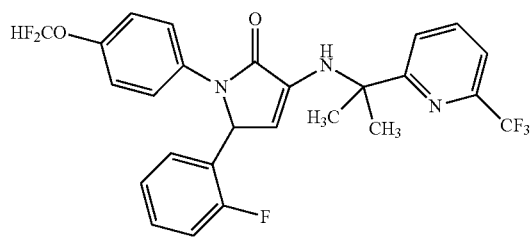

Add HOAc (2.1 mL, 36.5 mmol), 2,5-dimethoxytetrahydrofuran (1.8 mL, 13.7 mmol), water (10 mL), and trifluoroacetic acid (1.4 mL, 18.3 mmol) sequentially to a solution of (±)-5-(2-fluoro-phenyl)-1-(4-difluoromethoxy-phenyl)-3-(4-difluoromethoxy-phenylamino)-1,5-dihydro-pyrrol-2-one (4.35 g, 9.13 mmol) in THF (38 mL). Heat the reaction mixture to 35° C. for 22 hours. Observe significant formation of (±)-1-(4-difluoromethoxy-phenyl)-5-(2-fluoro-phenyl)-pyrrolidine-2,3-dione (LC-MS ESI m/z: 336 (M+H)+, T$_r$=3.38 min., method 1). Cool the reaction mixture to room temperature and add toluene (100 mL) in a single portion. Wash the mixture with water and then pH 7 buffer. Separate layers and observe that the aqueous layer is pH=7. Filter through sodium sulfate and add HOAc (1.05 mL, 18.3 mmol) and 1-methyl-1-(6-trifluoromethyl-pyridin-2-yl)-ethylamine (2.24 g, 11.0 mmol) to the toluene solution containing 1-(4-difluoromethoxy-phenyl)-5-(2-fluoro-phenyl)-pyrrolidine-2,3-dione. Heat to 55° C. for 18 hours. Concentrate the reaction mixture and purify by silica gel chromatography (5-25% EtOAc-hexane) to yield the title compound (2.36 g, 50%) as an oil, LC-MS ESI m/z: 522 (M+H)+, T$_r$=5.15 min., method 1.

Prepare the following compounds essentially by the method of Preparation 53.

TABLE 3

| Prep No | Compound and Name | Yield, Comments, and Physical Data |
|---|---|---|
| 54 | ![structure] (±)-3-[1-Methyl-1-(6-trifluoromethyl-pyridin-2-yl)-ethylamino]-1-(4-trifluoromethoxy-phenyl)-5-(3,4-difluoro-phenyl)-1,5-dihydro-pyrrol-2-one | Yield 42% LC-MS ESI m/z: 558 (M + H)+, T$_r$ = 3.30 min., method 2. |
| 55 | ![structure] (±)-3-[1-Methyl-1-(6-trifluoromethyl-pyridin-2-yl)-ethylamino]-1-(4-difluoromethoxy-phenyl)-5-phenyl-1,5-dihydro-pyrrol-2-one | Yield 60% LC-MS ESI m/z: 504 (M + H)+, T$_r$ = 3.29 min., method 2. |

TABLE 3-continued

| Prep No | Compound and Name | Yield, Comments, and Physical Data |
|---|---|---|
| 56 | 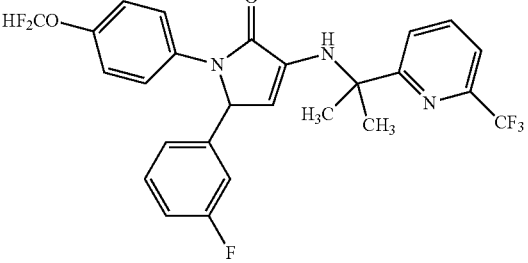<br>(±)-3-[1-Methyl-1-(6-trifluoromethyl-pyridin-2-yl)-ethylamino]-1-(4-difluoromethoxy-phenyl)-5-(3-fluoro-phenyl)-1,5-dihydro-pyrrol-2-one | Yield 56%<br>LC-MS ESI m/z: 522 (M + H)$^+$, T$_r$ = 3.31 min., method 2. |
| 57 | 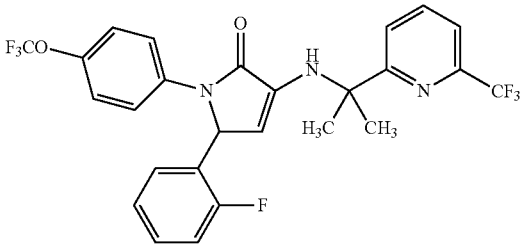 [SMILES: CC(C)(NC1=CC(c2ccccc2F)N(c2ccc(OC(F)(F)F)cc2)C1=O)c1cccc(C(F)(F)F)n1]<br>(±)-3-[1-Methyl-1-(6-trifluoromethyl-pyridin-2-yl)-ethylamino]-1-(4-trifluoromethoxy-phenyl)-5-(2-fluoro-phenyl)-1,5-dihydro-pyrrol-2-one | Yield 25%<br>LC-MS ESI m/z: 538 (M − H)$^-$, T$_r$ = 3.47. min., method 2.<br>Purify by silica gel chromatography (10%-50% EtOAc-hexanes) |
| 58 | 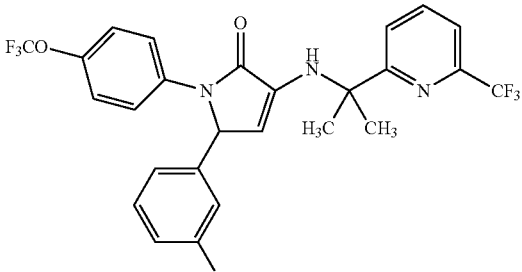<br>(±)-3-[1-Methyl-1-(6-trifluoromethyl-pyridin-2-yl)-ethylamino]-1-(4-trifluoromethoxy-phenyl)-5-(3-difluoromethoxy-phenyl)-1,5-dihydro-pyrrol-2-one | Yield 43%<br>LC-MS ESI m/z: 587.8 (M + H)$^+$, T$_r$ = 3.39. min., method 2.<br>Purify by silica gel chromatography (2%-45% EtOAc-hexanes) |
| 59 | 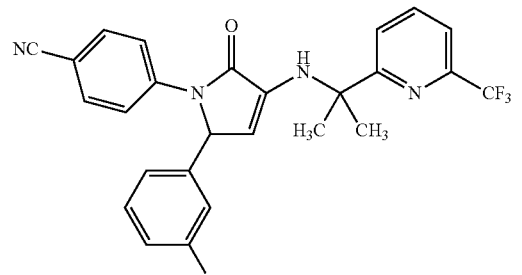<br>(±)-4-[3-[1-methyl-1-(6-trifluoromethyl-pyridin-2-yl)-ethylamino]-2-oxo-5-(3-difluoromethoxy-phenyl)-2,5-dihydro-pyrrol-1-yl]-benzonitrile | Yield 38%<br>LC-MS ESI m/z: 550.8 (M + Na)$^+$, T$_r$ = 3.19 min., method 2.<br>Purify by silica gel chromatography (2%-80% EtOAc-hexanes) |

TABLE 3-continued

| Prep No | Compound and Name | Yield, Comments, and Physical Data |
|---|---|---|
| 60 | 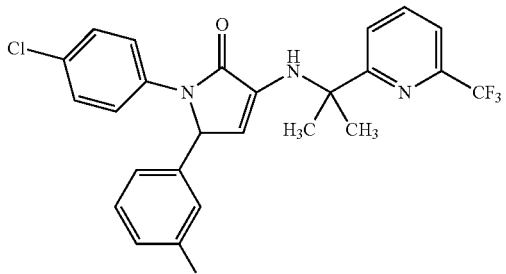<br>(±)-3-[1-Methyl-1-(6-trifluoromethyl-pyridin-2-yl)-ethylamino]-1-(4-chloro-phenyl)-5-(3-difluoromethoxy-phenyl)-1,5-dihydro-pyrrol-2-one | Yield 58%<br>LC-MS ESI m/z: 538.0 (M + H)$^+$, T$_r$ = 3.14 min., method 2. Purify by silica gel chromatography (2%-80% EtOAc-hexanes) |
| 61 | 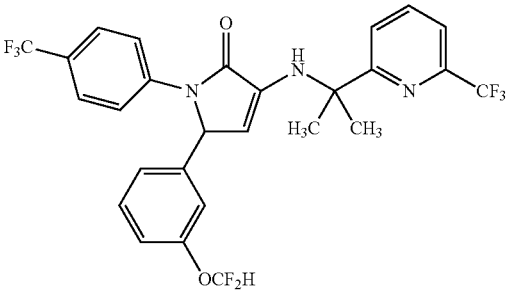<br>(±)-3-[1-Methyl-1-(6-trifluoromethyl-pyridin-2-yl)-ethylamino]-1-(4-trifluoromethyl-phenyl)-5-(3-difluoromethoxy-phenyl)-1,5-dihydro-pyrrol-2-one | Yield 42%<br>LC-MS ESI m/z: 572.0 (M + H)$^+$, T$_r$ = 3.19 min., method 2. Purify by silica gel chromatography (2%-80% EtOAc-hexanes) |
| 62 | 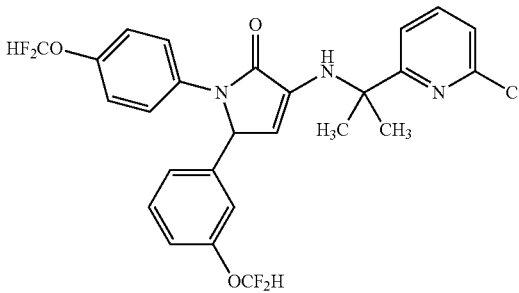<br>(±)-3-[1-Methyl-1-(6-trifluoromethyl-pyridin-2-yl)-ethylamino]-1-(4-difluoromethoxy-phenyl)-5-(3-difluoromethoxy-phenyl)-1,5-dihydro-pyrrol-2-one | Yield 48%<br>LC-MS ESI m/z: 569.8 (M + H)$^+$, T$_r$ = 3.25 min., method 2. Purify by silica gel chromatography (5%-45% EtOAc-hexanes) |

Preparation 63: (±)-3-[1-Methyl-1-(6-trifluoromethyl-pyridin-2-yl)-ethylamino]-1-(4-trifluoromethoxy-phenyl)-5-(3-trifluoromethyl-phenyl)-1,5-dihydro-pyrrol-2-one

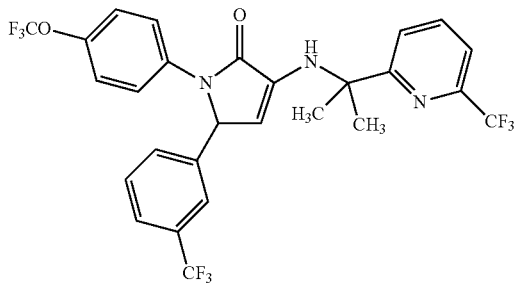 [SMILES: CC(C)(NC1=CC(c2cccc(C(F)(F)F)c2)N(c2ccc(OC(F)(F)F)cc2)C1=O)c1cccc(C(F)(F)F)n1]

Add acetic acid (3.6 mL, 63.2 mmol), 2,5-dimethoxytetrahydrofuran (3.1 mL, 23.7 mmol), and trifluoroacetic acid (2.4 mL, 31.6 mmol) sequentially to a solution of (±) 5-(3-trifluoromethyl-phenyl)-1-(4-trifluoromethoxy-phenyl)-3-(4-trifluoromethoxy-phenylamino)-1,5-dihydro-pyrrol-2-one (8.89 g, 15.8 mmol) in THF (12 mL) and water (3 mL). Heat the reaction mixture to 35° C. for 72 hours. Observe significant formation of (±)-1-(4-trifluoromethoxy-phenyl)-5-(3-trifluoromethyl-phenyl)-pyrrolidine-2,3-dione (LC-MS ESI m/z: 404 (M+H)$^+$, T$_r$=2.61 min., method 2). Cool the reaction mixture to room temperature and add toluene (20 mL) and isopropyl acetate (10 mL). Wash the mixture with saturated sodium bicarbonate solution and then brine. Filter through sodium sulfate. Add acetic acid (7.6 mL, 126 mmol) and 1-methyl-1-(6-trifluoromethyl-pyridin-2-yl)-ethylamine (4.89 g, 24.0 mmol) to the solution containing (±)-1-(4-trifluoromethoxy-phenyl)-5-(3-trifluoromethyl-phenyl)-pyrrolidine-2,3-dione. Heat to 55° C. for 1.5 hours. Pour reaction mixture into saturated sodium bicarbonate solution and separate phases. Dry over sodium sulfate, filter and concentrated under reduced pressure. Purify by silica gel chromatography (10-50% EtOAc-hexane) to yield the title compound (5.89 g, 63%) as an oil, LC-MS ESI m/z: 588 (M−H)$^-$, T$_r$=3.55. min., method 2.

Preparation 64: (3R,5R)-3-[1-Methyl-1-(6-trifluoromethyl-pyridin-2-yl)-ethylamino]-5-(3-methoxy-phenyl)-1-(4-trifluoromethyl-phenyl)-pyrrolidin-2-one

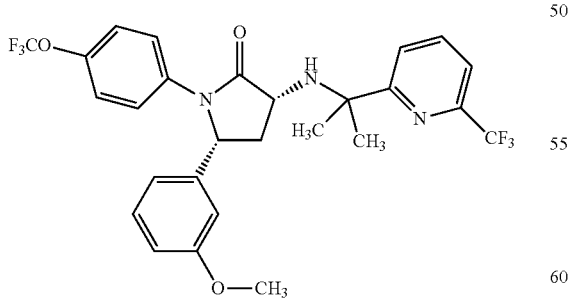

Add trifluoroacetic acid (5.5 mL, 72.9 mmol) to a mixture of 1-(4-trifluoromethyl-phenyl)-3-((R)-1-phenyl-ethylamino)-5(R)-(3-methoxy-phenyl)-1,5-dihydro-pyrrol-2-one (6.6 g, 14.6 mmol) in HOAc (81 mL) and water (3.7 mL). Stir at ambient temperature for 3 hours. Observe significant formation of (R)-5-(3-methoxy-phenyl)-1-(4-trifluoromethyl-phenyl)-pyrrolidine-2,3-dione (LC-MS ESI m/z: 350.2 (M+H)$^+$, T$_r$=3.71 min., method 1). Dilute the reaction mixture with toluene (100 mL) and wash the organic with water and pH 7 buffer. Filter through sodium sulfate and add HOAc (6.7 mL, 116.8 mmol) and 1-methyl-1-(6-trifluoromethyl-pyridin-2-yl)-ethylamine (3.6 g, 17.5 mmol) to this toluene solution containing (R)-5-(3-methoxy-phenyl)-1-(4-trifluoromethyl-phenyl)-pyrrolidine-2,3-dione. Heat to 50° C. for 18 hours. Concentrate reaction mixture to give a purple oil. Observe significant formation of 3-[1-methyl-1-(6-trifluoromethyl-pyridin-2-yl)-ethylamino]-1-(4-trifluoromethyl-phenyl)-5(R)-(3-methoxy-phenyl)-1,5-dihydro-pyrrol-2-one (LC-MS ESI m/z: 536.2 (M+H)$^+$, T$_r$=5.31 min., method 1). Dissolve the crude 3-[1-methyl-1-(6-trifluoromethyl-pyridin-2-yl)-ethylamino]-1-(4-trifluoromethyl-phenyl)-5(R)-(3-methoxy-phenyl)-1,5-dihydro-pyrrol-2-one in HOAc (73 mL) and add sodium cyanoborohydride (2.8 g. 43.8 mmol). Stir 3 hours at ambient temperature. Concentrate under reduced pressure. Partition the residue between dichloromethane and 1N sodium hydroxide solution. Extract the aqueous with dichloromethane. Dry the organic over sodium sulfate, filter and concentrate under reduced pressure. Purify the residue by silica gel chromatography (25% EtOAc-hexane) to obtain (3R,5R)-3-[1-methyl-1-(6-trifluoromethyl-pyridin-2-yl)-ethylamino]-5-(3-methoxy-phenyl)-1-(4-trifluoromethyl-phenyl)-pyrrolidin-2-one (3.55 g, 45%) as a brown oil. LC-MS ESI m/z: 538.2 (M+H)$^+$, T$_r$=3.35 min., method 1.

Preparation 65: (3R,5R)-3-[1-Methyl-1-(6-trifluoromethyl-pyridin-2-yl)-ethylamino]-5-(3-hydroxy-phenyl)-1-(4-trifluoromethyl-phenyl)-pyrrolidin-2-one

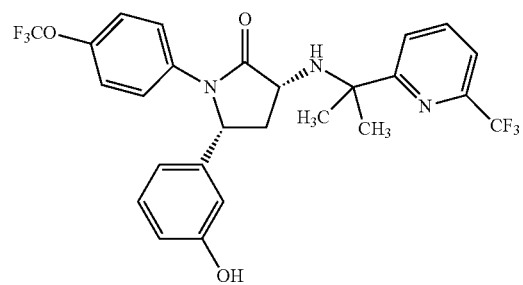 [SMILES: CC(C)(N[C@@H]1C[C@H](c2cccc(O)c2)N(c2ccc(OC(F)(F)F)cc2)C1=O)c1cccc(C(F)(F)F)n1]

Add (3R,5R)-3-[1-methyl-1-(6-trifluoromethyl-pyridin-2-yl)-ethylamino]-5-(3-methoxy-phenyl)-1-(4-trifluoromethyl-phenyl)-pyrrolidin-2-one (1.9 g, 3.4 mmol) to pyridine hydrochloride (28.6 g, 247.8 mmol). Plunge the mixture into a 185° C. oil bath and heat for 2 hours. Cool to ambient temperature and dilute with water (175 mL). Make the pH basic by ammonium hydroxide addition and extract with EtOAc. Wash with brine, dry over sodium sulfate, filter and concentrate the organic to residue. Purify the residue by silica gel chromatography (20%-30% EtOAc-hexane) to obtain (3R,5R)-3-[1-methyl-1-(6-trifluoromethyl-pyridin-2-yl)-ethylamino]-5-(3-hydroxy-phenyl)-1-(4-trifluoromethyl-phenyl)-pyrrolidin-2-one (0.58 g, 32%) as a white foam. LC-MS ESI m/z: 524.2 (M+H)$^+$, T$_r$=2.91 min., method 1.

Preparation 66: 3-(1,1-Difluoro-ethyl)-benzonitrile

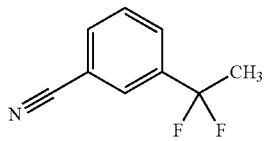

Place 3-acetylbenzonitrile (5.0 g, 34.4 mmol) into a 50 mL polypropylene screw cap tube. Add dichloromethane (17 mL), (bis(2-methoxyethyl)amino)sulfur trifluoride (15.2 g, 69 mmol), and ethanol (200 µL). Purge with nitrogen and heat at 55° C. with stirring overnight. Cool the reaction to room temperature, add the reaction carefully into saturated NaHCO$_3$ with rapid stirring, extract with dichloromethane, dry over magnesium sulfate and evaporate to an oil. Purify the product over silica with 10% Et$_2$O:hexanes. Evaporate to afford 3-(1,1-difluoro-ethyl)-benzonitrile as a colorless liquid. (4.4 g, 76%), $^1$H NMR (400 MHz, CDCl$_3$): δ 7.77 (s, 1H), 7.70 (t, J=7.3 Hz, 2H), 7.53 (t, J=7.9 Hz, 1H), 1.94-1.85 (m, 3H).

Preparation 67: 3-(1,1-Difluoro-ethyl)-benzaldehyde

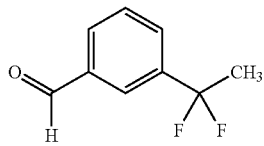

Dissolve 3-(1,1-difluoro-ethyl)-benzonitrile (4.39 g, 26.26 mmol) in toluene (44 mL). Place the reaction under nitrogen, cool to −78° C. in a dry-ice bath, then add diisobutylaluminum hydride (52.5 mmol, 1 M solution in toluene) dropwise over 30 minutes with stirring. Stir the reaction in the dry-ice bath for 30 minutes, then add glacial HOAc (14 mL) dropwise to control foaming, followed by water (100 mL). Stir the reaction mixture overnight at room temperature. Separate the layers; extract the cloudy aqueous with toluene. Wash the toluene extracts with brine, dry the organics over magnesium sulfate, filter, and evaporate to afford 3-(1,1-difluoro-ethyl)-benzaldehyde as a pale yellow oil. (4.0 g, 90%). $^1$H NMR (400 MHz, CDCl$_3$): δ 10.03 (s, 1H), 8.00 (s, 1H), 7.92 (d, J=7.5 Hz, 1H), 7.75 (d, J=7.5 Hz, 1H), 7.58 (t, J=7.7 Hz, 1H), 1.98-1.89 (m, 3H).

Preparation 68: 2-(6-Bromo-pyridin-2-yl)-propan-2-ol

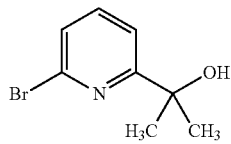

Place a 1.6 M solution of n-butyl lithium in hexane (31.2 mL, 50 mmol) in a dry 250 mL round bottomed flask fitted with a stir bar, septum and temperature probe. Cool in a dry-ice acetone bath to −76° C. Add THF (30 mL) to the solution, then add a solution of 2,6-dibromopyridine (11.5 g, 50 mmol) in THF (60 mL) slowly via syringe maintaining the temperature under −60° C. Stir the dark yellow-brown solution for 30 minutes in the dry-ice bath, then add acetone (6 mL, 80 mmol). Stir the deep green solution in the dry-ice bath for 15 minutes then allow the reaction to warm to room temperature. After an hour add a 5% aqueous solution of ammonium chloride (50 mL) carefully. Extract with dichloromethane, evaporate to give 2-(6-bromo-pyridin-2-yl)-propan-2-ol (10.6 g, 98%) as an orange oil. MS (m/z): 216 and 218 (M+H)$^+$.

Preparation 69: N-[1-(6-Bromo-pyridin-2-yl)-1-methyl-ethyl]-acetamide

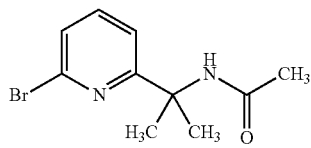

Dissolve 2-(6-bromo-pyridin-2-yl)-propan-2-ol (10.6 g, 50 mmol) in acetonitrile (40 mL). Add BF$_3$-Et$_2$O (20 mL, 125 mmol) and reflux for 3 days. Cool to room temperature, add ice and neutralize the reaction with 5N NaOH and extract with dichloromethane. Purify over silica (120 g) eluting with 0 to 100% EtOAc:hexanes to give N-[1-(6-bromo-pyridin-2-yl)-1-methyl-ethyl]-acetamide (3.3 g, 26%), MS (m/z): 257 and 259 (M+H)$^+$ and recovered 2-(6-bromo-pyridin-2-yl)-propan-2-ol (3.7 g, 34%).

Preparation 70: 1-(6-Bromo-pyridin-2-yl)-1-methyl-ethylamine

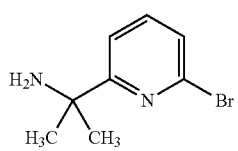

Combine N-[1-(6-bromo-pyridin-2-yl)-1-methyl-ethyl]-acetamide (3.3 g, 12.8 mmol) with 5N HCl (200 mL) and reflux overnight. Cool, add ice and neutralize with 1:1 ice: 50% NaOH until the mixture turns cloudy. Extract with dichloromethane, dry (Na₂SO₄), and evaporate to give 1-(6-bromo-pyridin-2-yl)-1-methyl-ethylamine (2.24 g, 81%). MS (m/z) 215 and 217 (M+H)⁺.

Preparation 71: [1-(6-Bromo-pyridin-2-yl)-1-methyl-ethyl]-carbamic acid tert-butyl ester

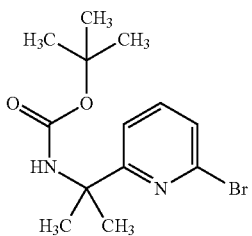

Dissolve 1-(6-bromo-pyridin-2-yl)-1-methyl-ethylamine (2.24 g, 10.4 mmol) in water (45 mL) and tert-butanol (45 mL). Add 1 N NaOH (10.4 mL, 10.4 mmol); then add di-tert-butyldicarbonate (2.5 g, 11.4 mmol) in portions. Stir the reaction at ambient temperature for 3 days. Extract with dichloromethane (3×30 mL). Wash the organics with brine (25 mL); dry over Na₂SO₄, filter, and evaporate. Purify the crude product over silica (220 g column) eluting with 25% EtOAc:hexanes to give [1-(6-bromo-pyridin-2-yl)-1-methyl-ethyl]-carbamic acid tert-butyl ester as a white solid (2.5 g, 76%). MS (m/z): 315, 317 (M+H)⁺.

Preparation 72: [1-(6-Cyclopropyl-pyridin-2-yl)-1-methyl-ethyl]-carbamic acid tert-butyl ester

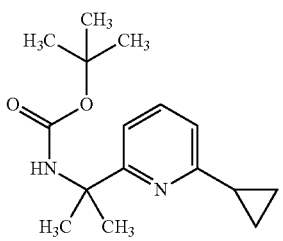 [SMILES: CC(C)(C)OC(=O)NC(C)(C)c1cccc(C2CC2)n1]

Combine [1-(6-bromo-pyridin-2-yl)-1-methyl-ethyl]-carbamic acid tert-butyl ester (250 mg, 1.16 mmol), cyclopropyl boronic acid (129 mg, 1.5 mmol), potassium phosphate (920 mg, 4.0 mmol), toluene (4.8 mL) and water (0.24 mL). Mix vigorously. Add 1M tricyclohexyl phosphine in toluene (120 μA, 0.12 mmol); degas the mixture, purge with nitrogen, and add palladium acetate 13 mg, (0.06 mmol) and heat at 100° C. for 6 hours, then stir at room temperature overnight. Filter the reaction and purify the filtrate over silica (80 g) eluting with 0% to 25% EtOAc:hexanes to give [1-(6-cyclopropyl-pyridin-2-yl)-1-methyl-ethyl]-carbamic acid tert-butyl ester (157 mg, 49%). MS (m/z): 277.3 (M+H)⁺.
Scale Up with Modification
Combine [1-(6-bromo-pyridin-2-yl)-1-methyl-ethyl]-carbamic acid tert-butyl ester (1.64 g, 7.6 mmol), cyclopropyl boronic acid (850 mg, 9.9 mmol), potassium phosphate (6.1 g, 26.6 mmol), and palladium acetate (85 mg, 0.38 mmol). Add toluene (31 mL) and water (1.4 mL) followed by 1M tricyclohexyl phosphine in toluene (760 μl, 0.76 mmol); degas the mixture, purge with nitrogen, and heat at 100° C. for 6 hours, then stir at room temperature overnight. Add tri tert-butylphosphine (153 mg, 0.76 mmol) and palladium acetate (85 mg, 0.38 mmol), degas and heat at 85° C. overnight. Filter the reaction and purify the filtrate over silica (120 g) eluting with 0% to 25% EtOAc:hexanes to give [1-(6-cyclopropyl-pyridin-2-yl)-1-methyl-ethyl]-carbamic acid tert-butyl ester as an oily yellow solid (1.3 g, 62%). MS (m/z): 277.4 (M+H)⁺.

Preparation 73: 1-(6-Cyclopropyl-pyridin-2-yl)-1-methyl-ethylamine

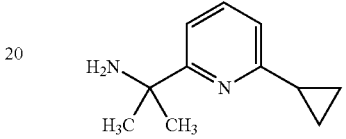

Dissolve [1-(6-cyclopropyl-pyridin-2-yl)-1-methyl-ethyl]-carbamic acid tert-butyl ester (1.3 g, 4.7 mmol) in 2 N HCl/Et₂O (excess) with a small amount of methanol to effect solution. Stir until the starting material is consumed, monitoring by LC-MS. Evaporate and partition the residue between dichloromethane and aqueous sodium bicarbonate. Extract with dichloromethane, filter and evaporate to give 1-(6-cyclopropyl-pyridin-2-yl)-1-methyl-ethylamine as an orange oil (610 mg, 75%). LC-MS ESI m/z: 177.2 (M+H)⁺, $T_r$=1.80 min, method 1.

Preparation 74: 1-Methyl-1-pyridin-2-yl-ethylamine

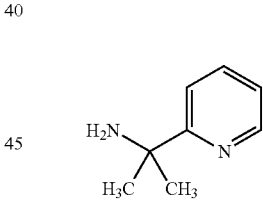

Add THF (240 mL) to anhydrous cerium (III) chloride (35 g, 144 mmol) and stir the slurry under nitrogen for 30 minutes. Cool the mixture to −76° C. in a dry-ice acetone bath. Add a 1.6 M solution of methyl lithium in Et₂O (90 mL, 144 mmol) dropwise maintaining the internal reaction temperature below −60° C. Stir for 30 minutes after the addition is complete, cool the reaction to −76° C., then add 2-cyanopyridine (5 g, 48 mmol) as a solution in THF (20 mL) controlling the addition to keep the reaction below −60° C. Stir the mixture in the dry-ice bath for 15 minutes, then remove the bath and allow the reaction to warm to 15° C. Cool the reaction in the dry-ice bath then add ammonium hydroxide (90 mL) with stirring. Allow the reaction to warm to room temperature with stirring overnight. Decant the solution from the mixture and wash the solids well with THF. Combine the filtrate and washes, then evaporate to give 1-methyl-1-pyridin-2-yl-ethylamine in quantitative mass balance. $^1$H NMR (400 MHz, CDCl$_3$): δ 8.52 (d, J=4.0 Hz, 1H), 7.60 (td, J=7.7, 1.6 Hz, 1H), 7.42 (d, J=7.9 Hz, 1H), 7.15-7.08 (m, 1H), 1.47 (s, 6H).

Preparation 75: (1-Methyl-1-pyridin-2-yl-ethyl)-carbamic acid tert-butyl ester

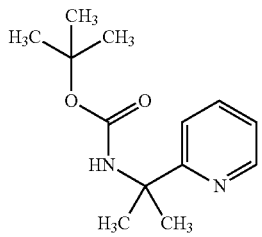 [SMILES: CC(C)(C)OC(=O)NC(C)(C)c1ccccn1]

Add di-tert-butyldicarbonate (10.4 g, 48 mmol) to a solution of 1-methyl-1-pyridin-2-yl-ethylamine (6.5 g, 48 mmol) in dichloromethane (65 mL). Add N,N-dimethyl-4-pyridinamine (120 mg, 1.0 mmol) and stir the reaction at room temperature overnight. Remove the solvents by evaporation, then purify the residue over silica eluting with 25% EtOAc:hexanes to give (1-methyl-1-pyridin-2-yl-ethyl)-carbamic acid tert-butyl ester as a yellow oil. (2.3 g, 20%). LC-MS ESI m/z: 237.2 (M+H)$^+$, T$_r$=1.08 min., method 2.

Preparation 76: [1-Methyl-1-(1-oxy-pyridin-2-yl)-ethyl]-carbamic acid tert-butyl ester

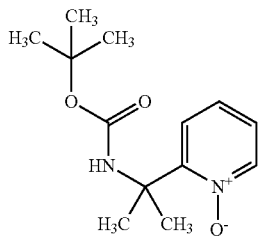 [SMILES: CC(C)(C)OC(=O)NC(C)(C)c1cccc[n+]1[O-]]

Add m-chloroperoxybenzoic acid (4.2 g, 24 mmol) to a solution of (1-methyl-1-pyridin-2-yl-ethyl)-carbamic acid tert-butyl ester (2.3 g, 10 mmol) in dichloromethane (70 mL). Stir the reaction at room temperature overnight. Add 2 N NaOH (12 mL). Extract with dichloromethane, dry the organic extracts (MgSO$_4$) and evaporate to give [1-methyl-141-oxy-pyridin-2-yl)-ethyl]-carbamic acid tert-butyl ester (2.17 g, 88% yield). LC-MS ESI m/z: 253.2 (M+H)$^+$, T$_r$=1.6 min., method 2.

Preparation 77: [1-(6-Cyano-pyridin-2-yl)-1-methyl-ethyl]-carbamic acid tert-butyl ester

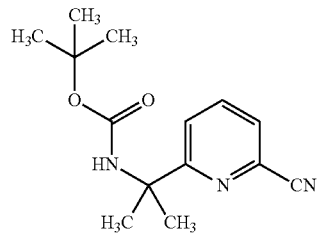 [SMILES: CC(C)(C)OC(=O)NC(C)(C)c1cccc(C#N)n1]

Add trimethylsilyl cyanide (2.1 g, 21 mmol) to a solution of [1-methyl-1-(1-oxy-pyridin-2-yl)-ethyl]-carbamic acid tert-butyl ester (2.4 g, 10 mmol) in dichloromethane (34 mL). Stir the reaction at room temperature for 10 minutes. Add benzoyl chloride (2.7 g, 20 mmol) and stir the reaction at room temperature overnight. Add the reaction carefully to 10% aqueous sodium bicarbonate solution (50 mL) with rapid stirring. Separate the layers and extract with dichloromethane. Evaporate the extracts and purify the yellow liquid over silica eluting with 25% EtOAc:hexanes to give [1-(6-cyano-pyridin-2-yl)-1-methyl-ethyl]-carbamic acid tert-butyl ester as a clear colorless oil that crystallized with standing. (1.83 g, 72%). LC-MS ESI m/z: 284.2 (M+Na)$^+$, T$_r$=2.24 min., method 2.

Preparation 78: 6-(1-Amino-1-methyl-ethyl)-pyridine-2-carbonitrile hydrochloride salt

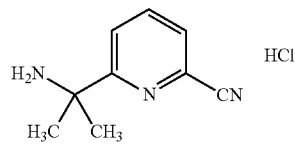

Add 4N HCl in dioxane (17 mL, 68 mmol) to [1-(6-cyano-pyridin-2-yl)-1-methyl-ethyl]-carbamic acid tert-butyl ester (1.2 g, 5 mmol). Stir the solution at room temperature for 10 minutes and observe the formation of a white solid. Stir the reaction at room temperature for 4 hours. Evaporate the solvent to give 6-(1-amino-1-methyl-ethyl)-pyridine-2-carbonitrile hydrochloride salt as a white solid (880 mg, 97% yield). MS ESI m/z: 162.3 (M+H)$^+$.

Preparation 79: 6-(1-Amino-1-methyl-ethyl)-pyridine-2-carbonitrile

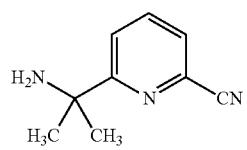

Partitioned 6-(1-amino-1-methyl-ethyl)-pyridine-2-carbonitrile hydrochloride salt (880 mg, 3.8 mmol) between dichloromethane and 10% aqueous sodium bicarbonate (10 mL). Separate the layers and extract with dichloromethane (3×10 mL). Dry the organic extracts (Na$_2$SO$_4$) and evaporate to give 6-(1-amino-1-methyl-ethyl)-pyridine-2-carbonitrile in quantitative yield. $^1$H NMR (400 MHz, CDCl$_3$) δ 7.76-7.68 (m, 2H), 7.50 (d, J=7.5 Hz, 1H), 1.87-1.80 (m, 2H), 1.47 (s, 6H).

Preparation 80:
6-Trifluoromethyl-pyridine-2-carboxylic acid methyl ester

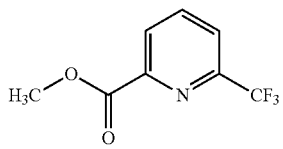

Add palladium(II) acetate (200 mg, 2 w/w %) and 1,1'-bis(diphenylphosphino)ferrocene (dppf) (400 mg, 4 w/w %) to a solution of 2-chloro-6-trifluoromethyl-pyridine (10.0 g, 55.1 mmol) in methanol (30 mL). To the orange solution add triethylamine (8.45 mL, 60.6 mmol). Purge the mixture with nitrogen and then maintain under an atmosphere of carbon monoxide (40 psig) at 60° C. for 17 h. Cool to ambient temperature and concentrate under a reduced pressure. Dissolve the solid in tert-butylmethyl ether (70 mL). Filter the resulting slurry over silica gel (10 g) and diatomaceous earth (10 g). Concentrate the filtrate to afford the title compound as a light orange solid (10.8 g, 96%). $^1$H NMR (399.84 MHz, DMSO d$_6$): 8.31-8.27 (m, 1H), 8.14 (dd, J=2.4, 6.4 Hz, 2H), 3.91 (s, 3H). HRMS (ESI) m/z (M+H)$^+$ calcd for C$_8$H$_7$F$_3$NO$_2$: 206.0423, found 206.0422.

Preparation 81:
2-(6-Trifluoromethyl-pyridin-2-yl)-propan-2-ol

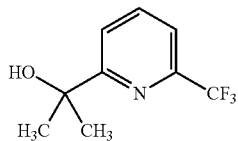

Add 6-trifluoromethyl-pyridine-2-carboxylic acid methyl ester (80.0 g, 390 mmol) to a mixture of THF (240 mL) and tert-butylmethyl ether (400 mL). Add the solution slowly to a 3 M methylmagnesium chloride in THF (390 mL, 1.17 moles) and maintain 8° C. to 16° C. Cool the mixture to 0° C. and add a mixture of 5 M hydrochloric acid (257 mL, 1.29 moles) and water (200 mL). Separate the phases and concentrate the organic phase under reduced pressure. Add heptane (160 mL) and cool the mixture to 5° C. Collect the precipitate by vacuum filtration and rinse the solid with heptane (20 mL) followed by pentane (30 mL). Vacuum dry the solid to afford the title compound as a tan solid (72.3 g, 352 mmol, 90%). $^1$H NMR (400 MHz, DMSO d$_6$) δ 8.04 (t, J=7.7 Hz, 1H), 7.94 (d, J=7.9 Hz, 1H), 7.69 (d, J=7.0 Hz, 1H), 5.40 (s, 1H), 1.43 (s, 6H). HRMS (ESI) m/z (M+H)$^+$ calcd for C$_9$H$_{10}$F$_3$NO: 206.0787, found 206.0787.

Preparation 82: N-[1-Methyl-1-(6-trifluoromethyl-pyridin-2-yl)-ethyl]-acetamide

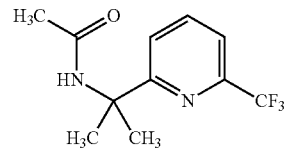 [SMILES: CC(=O)NC(C)(C)c1cccc(C(F)(F)F)n1]

Add 2-(6-trifluoromethyl-pyridin-2-yl)-propan-2-ol (44.4 g, 216 mmol) to acetonitrile (450 mL) and cool the mixture to 0° C. Add concentrated sulfuric acid (35 mL, 657 mmol) and maintain 10° C. or lower during the addition. Warm the mixture to 45° C. for 16.5 hours, then cool the mixture to 4° C. Add 1 N NaOH (1.3 L). Add t-butylmethyl ether (900 mL) and separate the layers. Extract the aqueous layer with t-butylmethyl ether (450 mL) and separate the layers. Combine the organic layers and extract with brine (450 mL), then separate the phases and add anhydrous sodium sulfate. Filter the suspension and concentrate the filtrate to dryness under reduced pressure to afford N-[1-methyl-1-(6-trifluoromethyl-pyridin-2-yl)-ethyl]-acetamide (43.9 g, 219 mmol, 82%). $^1$H NMR (400 MHz, DMSO d$_6$) δ 8.26 (s, 1H), 7.95 (t, J=7.9 Hz, 1H), 7.63 (dd, J=7.7, 17.4 Hz, 2H), 1.82 (s, 3H), 1.51 (s, 6H). HRMS (ESI) m/z (M+H)$^1$ calcd for C$_{11}$H$_{14}$F$_3$N$_2$O (M+H)$^+$: 247.1053, found 247.1051.

Preparation 83: 1-Methyl-1-(6-trifluoromethyl-pyridin-2-yl)-ethylamine

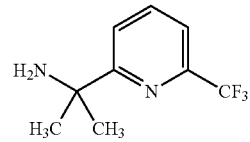

Add N-[1-methyl-1-(6-trifluoromethyl-pyridin-2-yl)-ethyl]-acetamide (20 g; 81.2 mmol) to a mixture of water (30 mL) and concentrated hydrochloric acid (30 mL; 365 mmol). Heat the mixture to 90° C. for 16 hours. Cool the mixture to 15° C. and add 100 mL 5 N sodium hydroxide to pH 13. Extract the mixture three times with t-butylmethyl ether (100 mL). Combine the t-butylmethyl ether layers and extract with 1 N HCl (100 mL), then twice with 0.5 N HCl (100 mL). Combine the acidic aqueous layers and stir with t-butylmethyl ether (50 mL). Clarify the mixture by filtration and separate the layers. Add brine (100 mL) and 5 N NaOH (70 mL) to pH 13. Extract the aqueous layer 3 times with t-butylmethyl ether (100 mL). Combine the t-butylmethyl ether layers and wash with a mixture of brine (95 mL) and 5 N NaOH (5 mL). Separate the layers and add sodium sulfate to the t-butylmethyl ether layer. Filter and concentrate the filtrate under reduced pressure to afford the title compound as a brown oil (14.2 g, 69.54 mmol; 86%) $^1$H NMR 500.174 MHz (CDCl$_3$) δ 7.79 (t, J=7.96 Hz, 1H), 7.64 (d, J=7.69 Hz, 1H), 7.49 (d, J=7.69 Hz, 1H), 2.0 (s, 2H), 1.50 (s, 6H). HRMS (ESI) m/z (M+H)$^1$ calcd for C$_9$H$_{12}$F$_3$N$_2$: 205.0947, found 205.0946.

Preparation 84: 1-Methyl-1-(6-trifluoromethyl-pyridin-2-yl)-ethylamine 4-methylbenzenesulfonate (1:1)

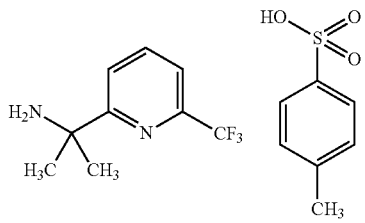

Add a solution of p-toluenesulfonic acid monohydrate (3.07 g, 16.1 mmol) in t-butylmethyl ether (25 mL) at 40° C. to a solution of 1-methyl-1-(6-trifluoromethyl-pyridin-2-yl)-ethylamine (3.20 g, 15.7 mmol) in t-butylmethyl ether (15 mL) at 35° C. Allow to cool to ambient temperature, and then add t-butylmethyl ether (10 mL). Stir at ambient temperature for approximately 1 hr. Filter and dry the resulting solid under vacuum at 40° C. to afford the title compound as an off white solid (5.17 g, 88%). $^1$H NMR (500 MHz, DMSO-d6) δ 8.42 (s, 3H), 8.22 (t, J=8.0 Hz, 1H), 7.98 (d, J=8.0 Hz, 1H), 7.93 (d, J=8.0 Hz, 1H), 7.46 (d, J=8.3 Hz, 2H), 7.10 (d, J=8.3 Hz, 2H), 2.27 (s, 3H), 1.63 (s, 6H).

Preparation 85: 1-Methyl-1-(6-trifluoromethyl-pyridin-2-yl)-ethylamine hydrochloride

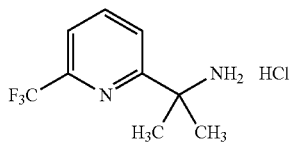

Prepare a solution of 1-methyl-1-(6-trifluoromethyl-pyridin-2-yl)-ethylamine (25.5 g, 124.88 mmol) in Et$_2$O (100 mL) and add 1M hydrogen chloride solution in Et$_2$O (137.37 mL, 137.37 mmol) at room temperature. Filter the precipitate and dry under vacuum to afford the title compound (30 g, 99%) as a tan solid. $^1$H NMR (DMSO-d$_6$) δ 8.80 (br s, 3H); 8.20 (t, J=8.0 Hz, 1H); 8.05 (d, J=8.0 Hz, 1H); 7.93 (d, J=8.0 Hz, 1H); 1.67 (s, 6H). $^{19}$F NMR (DMSO-d$_6$)-66.27.

Preparation 86: (±)-5-Phenyl-1-(4-trifluoromethoxy-phenyl)-3-(4-trifluoromethoxy-phenylamino)-1,5-dihydro-pyrrol-2-one

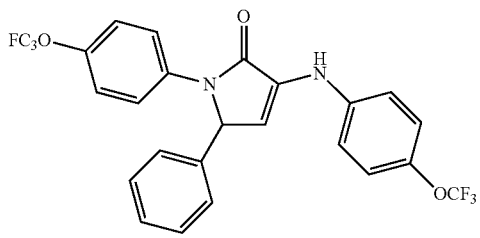

Add 4-(trifluoromethoxy)aniline (1.86 L, 13.75 mol) in portions to a solution of benzaldehyde (559 mL, 5.50 mol), and ethyl pyruvate (605 mL, 5.50 mol) in glacial acetic acid (5.0 L). Observe exotherm to 43° C. Stir at ambient temperature for 18 hours. Filter the precipitate, and wash the wet cake with glacial acetic acid (500 mL). Dry under vacuum for 3 hours to afford the title compound (1999 g, 74%) as a white crystalline solid. $^1$H NMR (400 MHz, DMSO-d$_6$) δ 8.43 (s, 1H), 7.74 (d, J=12 Hz, 2H), 7.19-7.38 (m, 11H), 6.42 (s, 1H), 6.08 (s, 1H). LC-MS ESI m/z: 495.0 (M+1)$^+$, 493.0 (M−1)$^-$, T$_r$=6.60 min., method 1.

Preparation 87: 1-(4-Trifluoromethoxy-phenyl)-3-((R)-1-phenyl-ethylamino)-5(R)-phenyl-1,5-dihydro-pyrrol-2-one

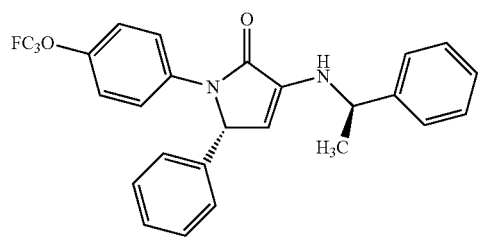

Add HOAc (464 mL, 8.09 mol), 2,5-dimethoxytetrahydrofuran (393 mL, 3.03 mol), water (2.27 L), and trifluoroacetic acid (153 mL, 2.02 mol) sequentially to a solution of (±)-5-phenyl-1-(4-trifluoromethoxy-phenyl)-3-(4-trifluoromethoxy-phenylamino)-1,5-dihydro-pyrrol-2-one (1000 g, 2.02 mol) in THF (8.43 L). Stir the reaction mixture at ambient temperature for 18 hours. Add toluene (4.0 L) and isopropyl acetate (2.0 L). Wash the mixture with water (8.0 L) and saturated sodium hydrogencarbonate solution (6.0 L). Discard the aqueous layer. To the organic layer, add (R)-(+)-α-methyl benzylamine (390 mL, 3.03 mol). Stir the solution at ambient temperature for 3 hours. Concentrate the reaction mixture to obtain a mixture of 1-(4-trifluoromethoxy-phenyl)-3-(R)-1-phenyl-ethylamino)-5(S)-phenyl-1,5-dihydro-pyrrol-2-one and 1-(4-trifluoromethoxy-phenyl)-3-((R)-1-phenyl-ethylamino)-5(R)-phenyl-1,5-dihydro-pyrrol-2-one as a black oil. Dissolve the mixture (888 g, 2.02 mol) in isopropanol (2.0 L) and cool to −7° C. Filter the precipitate and wash with cold isopropanol. Dry under vacuum for 12 hours to give 1-(4-trifluoromethoxy-phenyl)-3-(R)-1-phenyl-ethylamino)-5(R)-phenyl-1,5-dihydro-pyrrol-2-one (130 g, 29%) as an off-white solid. $^1$H NMR (400 MHz, DMSO-d$_6$) δ 7.64 (d, J=8 Hz, 2H), 7.34 (d, J=8 Hz, 2H), 7.24 (m, 4H), 7.11 (m, 4H), 6.98 (d, J=4 Hz, 2H), 5.78 (m, 2H), 5.13 (s, 1H), 4.30 (m, 1H), 1.44 (d, J=4 Hz 3H). LC-MS ESI m/z: 439 (M+H)$^+$, T$_r$=6.30 min., method 1.

Preparation 88: (R)-3-[1-Methyl-1-(6-trifluoromethyl-pyridin-2-yl)-ethylamino]-1-(4-trifluoromethoxy-phenyl)-5-phenyl-1,5-dihydro-pyrrol-2-one

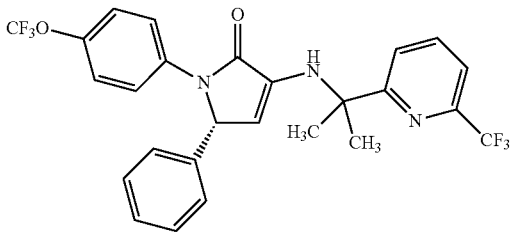

Add water (490 mL) and trifluoroacetic acid (126 mL, 1.67 mol) sequentially to a solution of 1-(4-trifluoromethoxy-phenyl)-3-(R)-1-phenyl-ethylamino)-5(R)-phenyl-1,5-dihydro-pyrrol-2-one (245 g, 558 mmol) in toluene (1.22 L). Stir at ambient temperature for 2 hours. Add water (1.0 L) and discard the aqueous layer. Wash the organic layer with 1N HCl (500 mL×2). To the organic layer add HOAc (10 mL, 174 mmol) and 1-methyl-1-(6-trifluoromethyl-pyridin-2-yl)-ethylamine (170 g, 836 mmol). Heat to 40° C. for 18 hours. Add water (400 mL), separate and discard the aqueous layer. Wash the organic layer with water (500 mL) and concentrate the organic layer to a dark oil. Dissolve the residue in toluene (400 mL) and concentrate to a brown paste. Triturate the solid with 20% MTBE/hexanes (1.0 L). Filter the mixture and collect the title compound as white solid (190 g, 65%). $^1$H NMR (400 MHz, DMSO-$d_6$) δ 8.01 (m, 1H), 7.83 (d, J=8 Hz, 1H), 7.69 (d, J=8 Hz, 1H), 7.64 (d, 12 Hz, 2H), 7.26 (d, J=8 Hz, 2H), 7.17 (m, 3H), 7.03 (d, J=8 Hz, 2H), 5.78 (s, 1H), 5.73 (s, 1H), 4.70 (s, 1H), 1.62 (s, 3H), 1.59 (s, 3H) LC-MS ESI m/z: 522 (M+H)$^+$, $T_r$=6.53 min., method 1.

Example 1

(3R,5R)-3-[1-Methyl-1-(6-trifluoromethyl-pyridin-2-yl)-ethylamino]-5-phenyl-1-(4-trifluoromethoxy-phenyl)-pyrrolidin-2-one

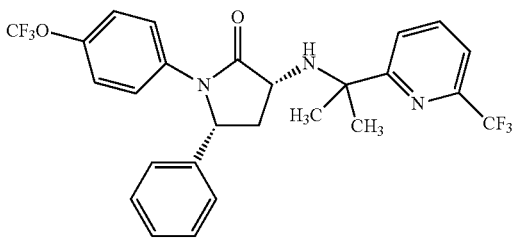

Add sodium triacetoxyborohydride (98 g, 465 mmol) in two portions to a solution of (R)-3-[1-methyl-1-(6-trifluoromethyl-pyridin-2-yl)-ethylamino]-1-(4-trifluoromethoxy-phenyl)-5-phenyl-1,5-dihydro-pyrrol-2-one (173 g, 332 mmol) and trifluoroacetic acid (50 mL, 664 mmol) in toluene (1.7 L). Stir for 3 hours and cannulate the mixture into water (2.5 L) over a period of 20 minutes. Extract the water with MTBE (2 L) and wash with water and sodium bicarbonate and concentrate to obtain the title compound as a tan oil (172 g, 98%). $^1$H NMR (400 MHz, DMSO-$d_6$) δ 8.07 (m, 2H), 7.71 (d, J=8 Hz, 1H), 7.39 (d, J=12 Hz, 2H), 7.21 (m, 8H), 5.16 (m, 1H), 3.42 (m, 1H), 2.68 (m, 1H), 1.63 (m, 1H), 1.38 (s, 3H), 1.43 (s, 3H).

Salt formation: hydrochloride. Prepare a solution of HCl by adding acetyl chloride (28.2 mL, 396.6 mmol) to a solution of toluene (1.75 L) and methanol (130 mL) at 2° C. and stir for 10 min. Add (3R,5R)-3-[1-methyl-1-(6-trifluoromethyl-pyridin-2-yl)-ethylamino]-5-phenyl-1-(4-trifluoromethoxy-phenyl)-pyrrolidin-2-one (173 g, 330.5 mmol) as a solution in toluene. Stir the mixture at ambient temperature for 18 hours. Concentrate the mixture to one-fourth the volume and filter the white solid that forms. Concentrate the filtrate to a purple foam. Slurry the foam in MTBE (500 mL) and collect the light purple solid that forms. Combine the white solid and light purple solid and slurry in isopropyl alcohol (40 mL) and MTBE (1.5 L). Stir for 2 hours, filter, and wash with MTBE (300 mL) and dry under vacuum at 40° 18 hours to give the title compound as a colorless solid (150 g, 81%). $^1$H NMR (400 MHz, CD3OD) δ 8.23 (t, J=8 Hz, 1H), 7.99 (d, J=8 Hz, 2H), 7.89 (d, J=8 Hz, 1H), 7.44 (d, J=8 Hz, 2H), 7.28 (m, 5H), 7.15 (d, J=8 Hz, 2H), 5.29 (m, 1H), 4.52 (m, 1H), 2.85 (m, 1H), 2.26 (m, 1H), 1.98 (s, 3H), 1.90 (s, 3H). LC-MS ESI m/z: 524 (M+H)$^+$, $T_r$=6.02 min., method 1.

Example 2

(3R,5R)-3-[1-Methyl-1-(6-trifluoromethyl-pyridin-2-yl)-ethylamino]-5-(3-trifluoromethoxy-phenyl)-1-(4-trifluoromethoxy-phenyl)-pyrrolidin-2-one

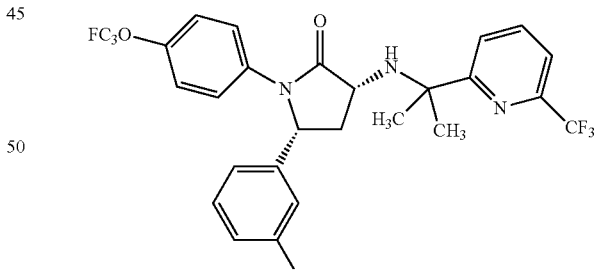

Add trifluoroacetic acid (1.88 mL, 24.9 mmol) to a biphasic mixture of 1-(4-trifluoromethoxy-phenyl)-3-(R)-1-phenyl-ethylamino)-5(R)-(3-trifluoromethoxy-phenyl)-1,5-dihydro-pyrrol-2-one (2.60 g, 4.98 mmol) in toluene (13 mL) and water (5 mL). Stir at ambient temperature for 60 min. Observe significant formation of 5-(R)-1-(4-trifluoromethoxy-phenyl)-5-(3-trifluoromethoxy-phenyl)-pyrrolidine-2,3-dione (LC-MS ESI m/z: 420 (M+H)$^+$, T$_r$=4.19 min., method 1). Wash the reaction mixture with water and pH 7 buffer. Filter through sodium sulfate and add HOAc (2.28 mL, 39.8 mmol) and 1-methyl-1-(6-trifluoromethyl-pyridin-2-yl)-ethylamine (1.02 g, 4.98 mmol) to this toluene solution containing 5-(R)-1-(4-trifluoromethoxy-phenyl)-5-(3-trifluoromethoxy-phenyl)-pyrrolidine-2,3-dione. Heat to 55° C. for 18 hours. Concentrate reaction mixture to give a red oil. Observe significant formation of (R)-3-[1-methyl-1-(6-trifluoromethyl-pyridin-2-yl)-ethylamino]-1-(4-trifluoromethoxy-phenyl)-5-(3-trifluoromethoxy-phenyl)-1,5-dihydro-pyrrol-2-one (LC-MS ESI m/z: 606 (M+H)$^+$, 604 (M−H)$^−$, T$_r$=5.70 min., method 1). Dissolve the crude (R)-3-[1-methyl-1-(6-trifluoromethyl-pyridin-2-yl)-ethylamino]-1-(4-trifluoromethoxy-phenyl)-5-(3-trifluoromethoxy-phenyl)-1,5-dihydro-pyrrol-2-one in HOAc (107 mL) and add sodium cyanoborohydride (2.68 g. 42.6 mmol). Stir 30 min. at ambient temperature. Concentrate under reduced pressure. Dissolve the residue in EtOAc and wash with 1N sodium hydroxide solution, water and saturated sodium chloride solution, dry over sodium sulfate, filter and concentrate under reduced pressure. Purify the residue by silica gel chromatography (5-40% EtOAc-hexane) to obtain (3R,5R)-3-[1-methyl-1-(6-trifluoromethyl-pyridin-2-yl)-ethylamino]-5-(3-trifluoromethoxy-phenyl)-1-(4-trifluoromethoxy-phenyl)-pyrrolidin-2-one (796 mg, 26%) as an oil. $^1$H NMR (400 MHz, DMSO-d$_6$) δ 8.09 (d, J=7.9 Hz, 1H), 8.01 (dd, J=7.8 Hz, 1H), 7.70 (d, J=7.5 Hz, 1H), 7.39-7.34 (m, 3H), 7.28 (d, J=7.9 Hz, 1H), 7.24-7.17 (m, 3H), 7.14 (d, J=7.9 Hz, 1H), 5.24 (dd, J=9.4, 6.4 Hz, 1H), 3.43 (dd, J=10.1, 8.4 Hz, 1H), 2.98 (br s, 1H), 2.77-2.69 (m, 1H), 1.64 (dd, J=21.8, 10.3 Hz, 1H), 1.47 (s, 3H), 1.42 (s, 3H). LC-MS ESI m/z: 608 (M+H)$^+$, T$_r$=3.88 min., method 1.

Salt formation: hydrochloride: Add hydrogen chloride (5 mL, 2.6 mmol, 0.52 N in ethanol) to (3R,5R)-3-[1-methyl-1-(6-trifluoromethyl-pyridin-2-yl)-ethylamino]-5-(3-trifluoromethoxy-phenyl)-1-(4-trifluoromethoxy-phenyl)-pyrrolidin-2-one (790 mg, 1.3 mmol) in ethanol to give a homogeneous solution. Concentrate to give the titled compound (844 mg, 100%) as a yellow foam. LC-MS ESI m/z: 608 (M+H)$^+$, T$_r$=4.06 min., method 1.

Prepare the following compounds essentially by the method of Example 2.

TABLE 4

| Ex No. | Compound, Name, Physical Data, Yield and Comment |
|---|---|
| 3 | 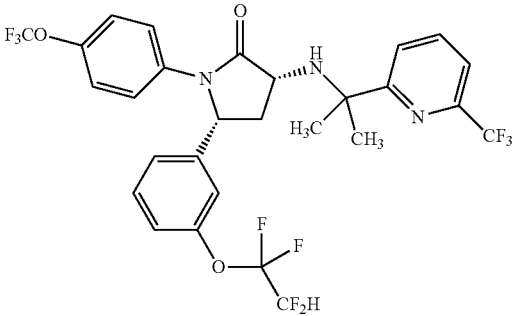 [SMILES: CC(C)(N[C@@H]1C[C@H](c2cccc(OC(F)(F)C(F)F)c2)N(c2ccc(OC(F)(F)F)cc2)C1=O)c1cccc(C(F)(F)F)n1] (3R,5R)-3-[1-Methyl-1-(6-trifluoromethyl-pyridin-2-yl)-ethylamino]-5-[3-(1,1,2,2-tetrafluoro-ethoxy)-phenyl]-1-(4-trifluoromethoxy-phenyl)-pyrrolidin-2-one<br>$^1$H NMR (400 MHz, DMSO-d$_6$) δ 8.09 (d, J = 7.9 Hz, 1H), 8.01 (dd, J = 7.8, 7.8 Hz, 1H), 7.70 (dd, J = 7.9, 0.8 Hz, 1H), 7.39-7.35 (m, 2H), 7.33 (d, J = 7.8 Hz, 1H), 7.25-7.19 (m, 3H), 7.11 (s, 1H), 7.04-7.07 (m, 1H), 6.70 (tt, J = 3.1, 51.6 Hz, 1H), 5.23 (dd, J = 9.7, 6.6 Hz, 1H), 3.46-3.38 (m, 1H), 2.97 (d, J = 4.0 Hz, 1H), 2.73 (ddd, J = 13.4, 6.8, 5.5 Hz, 1H), 1.63 (dd, J = 22.0, 10.5 Hz, 1H), 1.47 (s, 3H), 1.42 (s, 3H).<br>LC-MS ESI m/z: 640 (M + H)$^+$, T$_r$ = 3.93 min., method 1.<br>Yield 24%<br>Comment: Use 2 equivalents sodium cyanoborohydride for the reduction.<br>Salt formation: hydrochloride—Add hydrogen chloride (2.0 mL, 2.0 mmol, 1 M in ether) to (3R,5R)-3-[1-methyl-1-(6-trifluoromethyl-pyridin-2-yl)-ethylamino]-5-[3-(1,1,2,2-tetrafluoro-ethoxy)-phenyl]-1-(4-trifluoromethoxy-phenyl)-pyrrolidin-2-one (1.16 g, 1.81 mmol) in IPA and concentrate to give the hydrochloride salt (1.23 g, 94%) as a yellow foam.<br>LC-MS ESI m/z: 640 (M + H)$^+$, T$_r$ = 3.92 min., method 1. |

TABLE 4-continued

| Ex No. | Compound, Name, Physical Data, Yield and Comment |
|---|---|

4

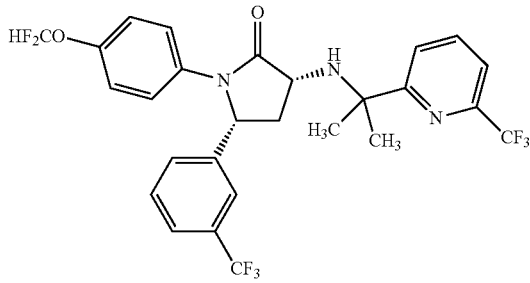

(3R,5R)-3-[1-Methyl-1-(6-trifluoromethyl-pyridin-2-yl)-ethylamino]-1-(4-difluoromethoxy-phenyl)-5-(3-trifluoromethyl-phenyl)-pyrrolidin-2-one
$^1$H NMR (400 MHz, DMSO-d$_6$) δ 8.09 (d, J = 7.9 Hz, 1H), 8.01 (dd, J = 7.8, 7.8 Hz, 1H), 7.70 (d, J = 7.5 Hz, 1H), 7.61 (s, 1H), 7.54-7.43 (m, 3H), 7.33-7.28 (m, 2H), 7.02 (d, J = 9.0 Hz, 2H), 7.10 (t, J = 73.7 Hz, 1H), 5.28 (dd, J = 9.7, 6.6 Hz, 1H), 3.46-3.38 (m, 1H), 2.96 (d, J = 3.1 Hz, 1H), 2.78-2.69 (m, 1H), 1.63 (dd, J = 22.0, 10.1 Hz, 1H), 1.47 (s, 3H), 1.42 (s, 3H).
LC-MS ESI m/z: 574.0 (M + H)$^+$, T$_r$ = 3.57 min., method 1.
Yield 49%.
Comment: Use HOAc instead of toluene for enamine hydrolysis. Use 1.2 equivalents of the amine to form the enamine. Use 3 equivalents of sodium cyanoborohydride for the reduction.

5

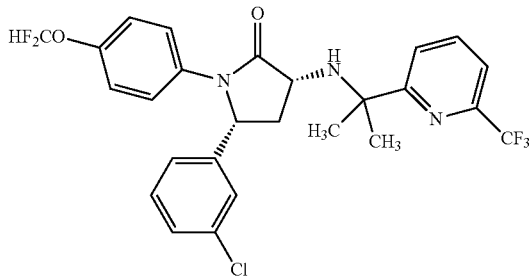

(3R,5R)-3-[1-Methyl-1-(6-trifluoromethyl-pyridin-2-yl)-ethylamino]-5-(3-chloro-phenyl)-1-(4-difluoromethoxy-phenyl)-pyrrolidin-2-one
$^1$H NMR (400 MHz, DMSO-d$_6$) δ 8.08 (d, J = 7.9 Hz, 1H), 8.01 (dd, J = 7.8, 7.8 Hz, 1H), 7.70 (d, J = 7.5 Hz, 1H), 7.33-7.29 (m, 3H), 7.28-7.15 (m, 3H), 7.03 (d, J = 9.0 Hz, 2H), 7.11 (t, J = 73.9 Hz, 1H), 5.16 (dd, J = 9.4, 6.4 Hz, 1H), 3.43-3.36 (m, 1H), 2.94 (d, J = 3.5 Hz, 1H), 2.73-2.65 (m, 1H), 1.60 (dd, J = 22.2, 10.3 Hz, 1H), 1.47 (s, 3H), 1.41 (s, 3H).
LC-MS ESI m/z: ($^{35}$Cl/$^{37}$Cl) 540.0/542.0 (M + H)$^+$, T$_r$ = 3.44 min., method 1.
Yield 51%.
Comment: Use HOAc instead of toluene for enamine hydrolysis. Use 1.2 equivalents of the amine to form the enamine. Use 3 equivalents of sodium cyanoborohydride for the reduction.

TABLE 4-continued

| Ex No. | Compound, Name, Physical Data, Yield and Comment |
| --- | --- |

6 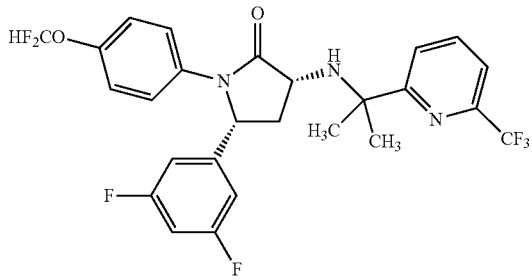

(3R,5R)-3-[1-Methyl-1-(6-trifluoromethyl-pyridin-2-yl)-ethylamino]-5-(3,5-difluoro-phenyl)-1-(4-difluoromethoxy-phenyl)-pyrrolidin-2-one $^1$H NMR (400 MHz, DMSO-$d_6$) δ 8.09 (d, J = 7.9 Hz, 1H), 8.01 (dd, J = 7.8, 7.8 Hz, 1H), 7.70 (d, J = 7.5 Hz, 1H), 7.35-7.30 (m, 2H), 7.07-6.97 (m, 5H), 7.12 (t, J = 73.7 Hz, 1H), 5.18 (dd, J = 9.4, 6.4 Hz, 1H), 3.44-3.37 (m, 1H), 2.92 (d, J = 3.5 Hz, 1H), 2.74-2.65 (m, 1H), 1.62 (dd, J = 22.0, 10.5 Hz, 1H), 1.47 (s, 3H), 1.42 (s, 3H)

LC-MS ESI m/z: 542.2 (M + H)$^+$, T$_r$ = 3.42 min., method 1.

Yield 44%.

Comment: Use HOAc instead of toluene for enamine hydrolysis. Use 1.2 equivalents of the amine to form the enamine. Use 3 equivalents of sodium cyanoborohydride for the reduction.

7 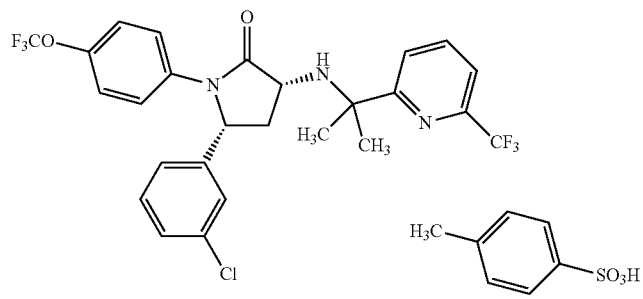 [SMILES: CC(C)(N[C@@H]1C[C@H](c2cccc(Cl)c2)N(c2ccc(OC(F)(F)F)cc2)C1=O)c1cccc(C(F)(F)F)n1 ; Cc1ccc(S(=O)(=O)O)cc1]

(3R,5R)-3-[1-Methyl-1-(6-trifluoromethyl-pyridin-2-yl)-ethylamino]-5-(3-chloro-phenyl)-1-(4-trifluoromethoxy-phenyl)-pyrrolidin-2-one tosylate Comment: Use 5 equivalents NaBH$_3$CN for the reduction.

Salt formation: tosylate—with 1 equivalent 4-toluene sulfonic acid in EtOAc. Crystallize from Et$_2$O. Yield 11% of the tosylate salt.

$^1$H NMR (400 MHz, CD$_3$OD) δ 8.18 (t, J = 7.9 Hz, 1H), 7.94-7.85 (m, 2H), 7.68-7.65 (m, 2H), 7.42-7.39 (m, 2H), 7.29-7.18 (m, 8H), 5.24 (dd, J = 6.2, 9.2 Hz, 1H), 4.49-4.39 (m, 1H), 2.85-2.78 (m, 1H), 2.33 (s, 3H), 2.17-2.07 (m, 1H), 1.88 (d, J = 30.8 Hz, 6H).

LC-MS ESI m/z: 558.0 (M + H)$^+$, T$_r$ = 2.364 min., method 2.

TABLE 4-continued

| Ex No. | Compound, Name, Physical Data, Yield and Comment |
|---|---|
| 8 | 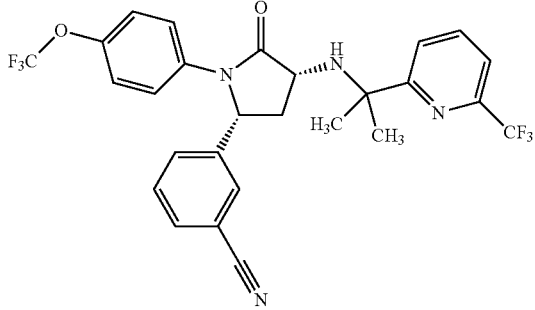 [SMILES: CC(C)(N[C@@H]1C[C@H](c2cccc(C#N)c2)N(c2ccc(OC(F)(F)F)cc2)C1=O)c1cccc(C(F)(F)F)n1]

3-[(2R,4R)-4-[1-Methyl-1-(6-trifluoromethyl-pyridin-2-yl)-ethylamino]-5-oxo-1-(4-trifluoromethoxy-phenyl)-pyrrolidin-2-yl]-benzonitrile
$^1$H NMR (400 MHz, CDCl$_3$) δ 7.80-7.78 (m, 2H), 7.50-7.46 (m, 3H), 7.38-7.32 (m, 2H), 7.25-7.23 (m, 3H), 7.05 (d, J = 8.4 Hz, 2H), 4.97 (dd, J = 6.2, 9.7 Hz, 1H), 3.46 (dd, J = 7.9, 10.5 Hz, 1H), 2.81-2.72 (m, 1H), 1.81-1.68 (m, 1H), 1.54 (d, J = 10.5 Hz, 6H).
LC-MS ESI m/z: 549.0 (M + H)$^+$, T$_r$ = 2.139 min., method 2.
Yield 3%.
Salt formation: Dihydrochloride—Add excess 2 N HCl in ether and evaporate to a white foam, giving quantitative mass balance. |
| 9 | 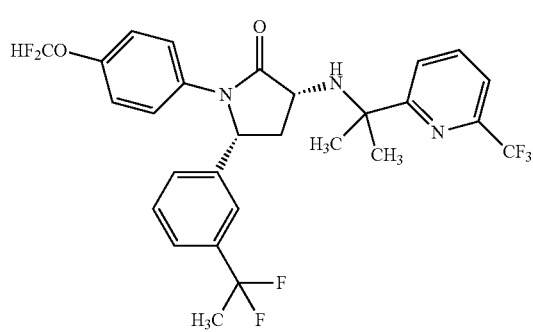

(3R,5R)-3-[1-Methyl-1-(6-trifluoromethyl-pyridin-2-yl)-ethylamino]-5-[3-(1,1-difluoro-ethyl)-phenyl]-1-(4-difluoromethoxy-phenyl)-pyrrolidin-2-one
$^1$H NMR (400 MHz, CDCl$_3$) δ 7.84-7.76 (m, 2H), 7.48 (d, J = 7.5 Hz, 1H), 7.28-7.16 (m, 7H), 6.92 (d, J = 8.8 Hz, 2H), 6.52-6.15 (m, 1H), 4.95 (dd, J = 5.9, 9.9 Hz, 1H), 3.44 (dd, J = 7.9, 11.0 Hz, 1H), 2.90-2.71 (m, 2H), 1.81-1.72 (m, 3H), 1.54 (d, J = 14.5 Hz, 6H).
LC-MS ESI m/z: 570.2 (M + H)$^+$, T$_r$ = 2.17 min., method 2.
Yield 8%
Salt formation: tosylate—with 1 equivalent p-toluene sulfonic acid in EtOAc. Evaporate to a foam, giving quantitative mass balance.
LC-MS ESI m/z: 570.2 (M + H)$^+$, T$_r$ = 2.16 min., method 2. |
| 10 | 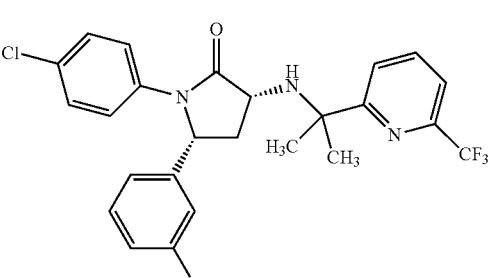

(3R,5R)-3-[1-Methyl-1-(6-trifluoromethyl-pyridin-2-yl)-ethylamino]-5-(3-trifluoromethoxy-phenyl)-1-(4-chloro-phenyl)-pyrrolidin-2-one.
$^1$H NMR (400 MHz, DMSO-d$_6$) δ 8.09 (d, J = 7.9 Hz, 1H), 8.02 (t, J = 7.9 Hz, 1H), 7.71 (dd, J = 7.4, 0.9 Hz, 1H), 7.37 (t, J = 7.9 Hz, 1H), 7.28-7.27 (m, 5H), 7.25-7.21 (m, 1H), 7.17-7.13 (m, 1H), 5.23 (dd, J = 9.7, 6.2 Hz, 1H), 3.46-3.39 (m, 1H), 2.96 (d, J = 4.0 Hz, 1H), 2.76-2.68 (m, 1H), 1.68-1.58 (m, 1H), 1.48 (s, 3H), 1.42 (s, 3H).
LC-MS ESI m/z: 558.0 (M + H)$^+$, T$_r$ = 3.72 min., method 1.
Yield 38% |

| Ex No. | Compound, Name, Physical Data, Yield and Comment |
|---|---|
| | Comment: Use 1.2 equivalents of the amine to form the enamine. Use 2 equivalents of sodium cyanoborohydride for the reduction.<br>Salt formation: tosylate—with 1 equivalent 4-toluene sulfonic acid in EtOAc. Crystallize from methanol-water to give a crystalline white solid (69%).<br>LC-MS ESI m/z: 558.0 (M + H)+, $T_r$ = 3.73 min., method 1. |
| 11 | 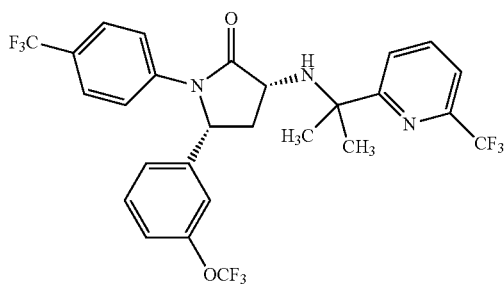 [SMILES: CC(C)(N[C@@H]1C[C@H](c2cccc(OC(F)(F)F)c2)N(c2ccc(C(F)(F)F)cc2)C1=O)c1cccc(C(F)(F)F)n1]<br>(3R,5R)-3-[1-Methyl-1-(6-trifluoromethyl-pyridin-2-yl)-ethylamino]-5-(3-trifluoromethoxy-phenyl)-1-(4-trifluoromethyl-phenyl)-pyrrolidin-2-one<br>1H NMR (400 MHz, DMSO-d6) δ 8.09 (d, J = 7.9 Hz, 1H), 8.02 (dd, J = 7.8 Hz, 7.8 Hz, 1H), 7.70 (d, J = 7.5 Hz, 1H), 7.58 (d, J = 8.4 Hz, 2H), 7.49 (d, J = 8.8 Hz, 2H), 7.40-7.34 (m, 1H), 7.28 (d, J = 7.5 Hz, 1H), 7.22 (s, 1H), 7.14 (d, J = 7.9 Hz, 1H), 5.30 (dd, J = 9.1, 6.6 Hz, 1H), 3.50-3.42 (m, 1H), 2.98 (d, J = 3.2 Hz, 1H), 2.79-2.70 (m, 1H), 1.65 (dd, J = 21.5, 11.0 Hz, 1H), 1.47 (s, 3H), 1.43 (s, 3H).<br>LC-MS ESI m/z: 592 (M + H)+, $T_r$ = 3.96 min., method 1. Yield 48%<br>Salt formation: hydrochloride: Dissolve free base in ethyl ether and cool to 0° C. Pass anhydrous HCl gas over the surface of the solution until solids precipitate. Warm to room temperature and stir vigorously overnight. Filter and wash with ether to give a white solid (90%).<br>LC-MS ESI m/z: 592 (M + H)+, $T_r$ = 4.07 min., method 1.<br>Salt formation: tosylate: In EtOAc, add one equivalent p-toluenesulfonic acid monohydrate and concentrate to give a pink foam (100%).<br>LC-MS ESI m/z: 592 (M + H)+, $T_r$ = 3.96 min., method 1. |
| 12 | 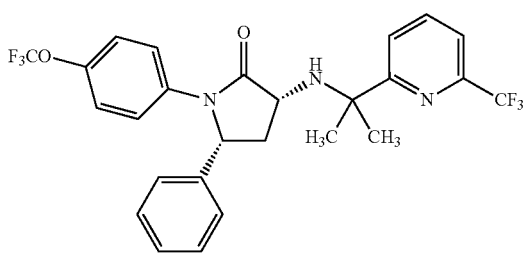 [SMILES: CC(C)(N[C@@H]1C[C@H](c2ccccc2)N(c2ccc(OC(F)(F)F)cc2)C1=O)c1cccc(C(F)(F)F)n1]<br>(3R,5R)-3-[1-Methyl-1-(6-trifluoromethyl-pyridin-2-yl)-ethylamino]-5-phenyl-1-(4-trifluoromethoxy-phenyl)-pyrrolidin-2-one<br>1H NMR (400 MHz, DMSO-d6) δ 8.07 (d, J = 7.9 Hz, 1H), 8.01 (dd, J = 7.9 Hz, 7.7 Hz, 1H), 7.70 (d, J = 7.5 Hz, 1H), 7.37 (d, J = 9.2 Hz, 2H), 7.23-7.19 (m, 6H), 7.17-7.12 (m, 1H), 5.15 (dd, J = 9.7, 6.6 Hz, 1H), 3.41 (ddd, J = 10.6, 8.1, 2.5 Hz, 1H), 2.96 (d, J = 3.5 Hz, 1H), 2.68 (ddd, J = 13.2, 6.8, 5.3 Hz, 1H), 1.61 (ddd, J = 19.2, 9.0, 2.9 Hz, 1H), 1.47 (s, 3H), 1.42 (s, 3H).<br>LC-MS ESI m/z: 524 (M + H)+, $T_r$ = 3.43 min., method 1. Yield 15%.<br>Comment: Use 1:1 acetic acid/dichloromethane as solvent in NaCNBH3 reduction and stir for 4 hr. Wash product with NaHCO3. Use 0%-50% EtOAc/hexanes as chromatography eluent.<br>Salt formation: hydrochloride: Dissolve free base in ethyl ether and cool to 0° C. Pass anhydrous HCl gas over the surface of the solution until solids precipitate. Warm to room temperature and stir vigorously overnight. Filter and wash with ether to give a white solid (93%).<br>LC-MS ESI m/z: 524 (M + H)+, $T_r$ = 3.39 min., method 1<br>1H NMR (400 MHz, DMSO-d6) δ 10.29 (br s, 1H), 9.39 (br s, 1H), 8.27-8.19 (m, 1H), 8.05 (d, J = 7.9 Hz, 1H), 7.93 (d, J = 8.4 Hz, 1H), 7.39 (d, J = 9.2 Hz, 2H), 7.32-7.22 (m, 6H), 7.22-7.17 (m, 1H), 5.22 (dd, J = 9.2, 6.2 Hz, 1H), 4.41 (br s, 1H), 2.64-2.55 (m, 1H), 2.20 (s, 1H), 1.79 (s, 6 H).<br>Salt formation: adipic acid co-crystal: Dissolve (3R,5R)-3-[1-methyl-1-(6-trifluoromethyl-pyridin-2-yl)-ethylamino]-5-phenyl-1-(4-trifluoromethoxy-phenyl)-pyrrolidin-2-one (1.76 g, 3.36 mmol) in methanol and add adipic acid (605 mg, 4.10 mmol). Sonicate for 5 min. to give a homogeneous solution. |

| Ex No. | Compound, Name, Physical Data, Yield and Comment |
|---|---|
| | Evaporate to give a thick clear solution. Seed with crystals. (Seeds of the adipic acid co-crystal were obtained from the free base and 1.2 eq. adipic acid in methanol. The methanol was allowed to evaporate and the resulting crystals were suspended in water, sonicated, filtered, washed with water and dried.) Stir until a white solid forms and dry under a stream of nitrogen. Add water (20 mL) and sonicate for 30 seconds. Filter and wash with water. Dry under nitrogen for 72 hr. to give a crystalline solid (1.70 g, 75%). |
| 13 | 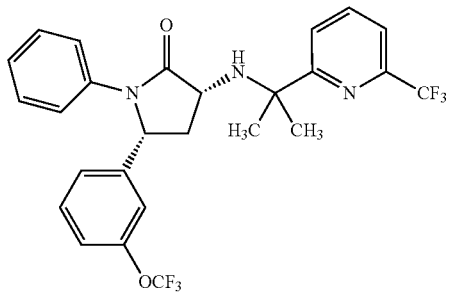 [SMILES: CC(C)(N[C@@H]1C[C@H](c2cccc(OC(F)(F)F)c2)N(c2ccccc2)C1=O)c1cccc(C(F)(F)F)n1]<br>(3R,5R)-3-[1-Methyl-1-(6-trifluoromethyl-pyridin-2-yl)-ethylamino]-5-(3-trifluoromethoxy-phenyl)-1-phenyl pyrrolidin-2-one<br>$^1$H NMR (400 MHz, DMSO-d$_6$) δ 8.09 (d, J = 7.9 Hz, 1H), 8.01 (dd, J = 7.9 Hz, 7.7 Hz, 1H), 7.70 (d, J = 7.7 Hz, 1H), 7.34 (dd, J = 7.9, 7.9 Hz, 1H), 7.27-7.17 (m, 6H), 7.14-7.09 (m, 1H), 7.04-6.98 (m, 1H), 5.24 (dd, J = 9.7, 6.2 Hz, 1H), 3.45-3.37 (m, 1H), 2.95 (d, J = 3.1 Hz, 1H), 2.72 (ddd, J = 13.2, 6.8, 5.3 Hz, 1H), 1.67-1.57 (m, 1H), 1.47 (s, 3H), 1.42 (s, 3H).<br>LC-MS ESI m/z: 524 (M + H)$^+$, T$_r$ = 3.36 min., method 1. Yield 57%.<br>Salt formation: dihydrochloride: Dissolve free base in ethyl ether and cool to 0° C. Pass anhydrous HCl gas over the surface of the solution until solids precipitate. Warm to room temperature and stir vigorously overnight. Filter and wash with ether to give a white solid (96%).<br>LC-MS ESI m/z: 524 (M + H)$^+$, T$_r$ = 3.37 min., method 1 |
| 14 | 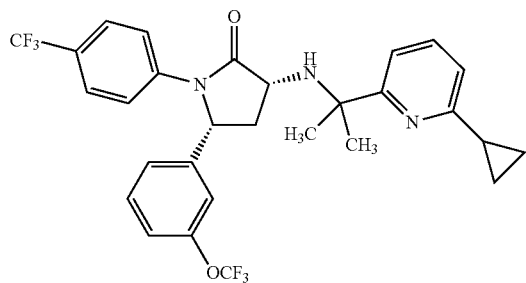 [SMILES: CC(C)(N[C@@H]1C[C@H](c2cccc(OC(F)(F)F)c2)N(c2ccc(C(F)(F)F)cc2)C1=O)c1cccc(C2CC2)n1]<br>(3R,5R)-3-[1-methyl-1-(6-cyclopropyl-pyridin-2-yl)-ethylamino]-5-(3-trifluoromethoxy-phenyl)-1-(4-trifluoromethyl-phenyl)-pyrrolidin-2-one<br>LC-MS ESI m/z: 563.6 (M + H)$^+$, T$_r$ = 3.39 min., method 1. Yield 22%.<br>Salt formation: dihydrochloride: Dissolve free base in dichloromethane and add 4 N HCl (2 equivalents) in dioxane. Mix well and evaporate to give a sticky yellow (100%).<br>$^1$H NMR (400 MHz, CD$_3$OD) δ 7.77 (t, J = 7.7 Hz, 1H), 7.57-7.52 (m, 4H), 7.38 (dd, J = 7.9, 9.7 Hz, 2H), 7.30-7.25 (m, 2H), 7.17-7.13 (m, 2H), 5.38 (dd, J = 6.4, 9.5 Hz, 1H), 4.31 (dd, J = 8.8, 11.4 Hz, 1H), 2.92-2.86 (m, 1H), 2.17-2.09 (m, 2H), 1.80 (d, J = 6.6 Hz, 6H), 1.14-1.09 (m, 2H), 1.02-0.95 (m, 2H).<br>LC-MS ESI m/z: 563.8 (M + H)$^+$, T$_r$ = 2.24 min., method 2. |

TABLE 4-continued

| Ex No. | Compound, Name, Physical Data, Yield and Comment |
|---|---|
| 15 | 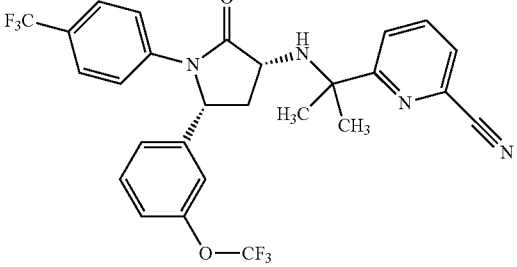

(3R,5R)-6-[1-Methyl-1-(2-oxo-5-(3-trifluoromethoxy-phenyl)-1-(4-trifluoromethyl-phenyl)-pyrrolidin-3-yl-amino)-ethyl]-pyridine-2-carbonitrile
LC-MS ESI m/z: 548.6 (M + H)$^+$, T$_r$ = 2.51 min., method 2. Yield 35%.
Salt formation: dihydrochloride: Dissolve free base in dichloromethane and add 4 N HCl (2 equivalents) in dioxane. Mix well and evaporate to give a sticky yellow (81%).
H1 NMR (400.43 MHz, CD$_3$OD): δ 8.16 (t, J = 7.9 Hz, 1H), 7.98-7.93 (m, 2H), 7.55 (s, 4H), 7.40 (t, J = 7.9 Hz, 1H), 7.32 (d, J = 7.9 Hz, 1H), 7.21 (s, 1H), 7.15 (d, J = 7.9 Hz, 1H), 5.46-5.41 (m, 1H), 4.56 (dd, J = 8.6, 11.7 Hz, 1H), 3.08-3.01 (m, 1H), 2.25-2.17 (m, 1H), 1.87 (d, J = 13.2 Hz, 6H).
LC-MS ESI m/z: 548.6 (M + H)$^+$, T$_r$ = 2.52 min., method 2. |

Example 16

(3R,5R)-3-[1-Methyl-1-(6-trifluoromethyl-pyridin-2-yl)-ethylamino]-5-(2-fluoro-phenyl)-1-(4-difluoromethoxy-phenyl)-pyrrolidin-2-one

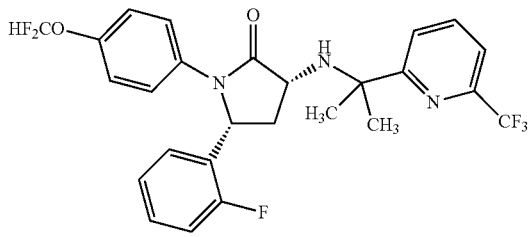

Dissolve (±)-3-[1-methyl-1-(6-trifluoromethyl-pyridin-2-yl)-ethylamino]-1-(4-difluoromethoxy-phenyl)-5-(2-fluoro-phenyl)-1,5-dihydro-pyrrol-2-one (2.06 g; 3.95 mmol) in HOAc (20 mL) and add sodium cyanoborohydride (0.50 g, 7.90 mmol). Stir for 2 hours at ambient temperature. Concentrate under reduced pressure and dissolve the residue in EtOAc. Wash the organic phase with 1N NaOH, water, saturated sodium chloride solution, dry over sodium sulfate, filter and concentrate under reduced pressure. Purify by silica gel chromatography (5-25% EtOAc-hexane) to yield (±)-3-[1-methyl-1-(6-trifluoromethyl-pyridin-2-yl)-ethylamino]-5-(2-fluoro-phenyl)-1-(4-difluoromethoxy-phenyl)-pyrrolidin-2-one (1.5 g, 73%), a racemic mixture, as a clear colorless oil. LC-MS ESI m/z: 524 (M+H)$^+$, T$_r$=3.18 min., method 1.

Separate the racemic mixture by Supercritical Fluid Chromatography (SFC) on a Chiralcel® OD-H column (21×250 mm, 5 µm) eluting with 15% methanol—0.2% isopropylamine in carbon dioxide (70 mL/min) to give (3S,5S)-3-[1-methyl-1-(6-trifluoromethyl-pyridin-2-yl)-ethylamino]-5-(2-fluoro-phenyl)-1-(4-difluoromethoxy-phenyl)-pyrrolidin-2-one (617 mg, 30%), analytical LCC SFC (Chiralcel® OD-H column, 10% MeOH (0.2% IPAm)/CO$_2$, 5 mL/min, 225 nM) T$_r$=1.28 min. $^1$H NMR (400 MHz, DMSO-d$_6$): δ 8.07 (d, J=7.9 Hz, 1H), 8.02 (dd, J=7.8, 7.8 Hz, 1H), 7.70 (d, J=7.5 Hz, 1H), 7.30-7.18 (m, 4H), 7.11-7.01 (m, 4H), 7.10 (t, J=73.9 Hz, 1H), 5.41 (dd, J=9.4, 6.4 Hz, 1H), 3.48-3.41 (m, 1H), 2.94 (d, J=3.1 Hz, 1H), 2.73-2.64 (m, 1H), 1.71 (dd, J=22.0, 10.1 Hz, 1H), 1.47 (s, 3H), 1.42 (s, 3H).

LC-MS ESI m/z: 524 (M+H)$^+$, T$_r$=3.21 min., method 1.

Salt formation: Add p-toluene sulfonic acid hydrate (204 mg, 1.06 mmol) to (3S,5S)-3-[1-methyl-1-(6-trifluoromethyl-pyridin-2-yl)-ethylamino]-5-(2-fluoro-phenyl)-1-(4-difluoromethoxy-phenyl)-pyrrolidin-2-one (554 mg, 1.06 mmol) in methanol to give a homogeneous solution. Concentrate under reduced pressure to give a white foam (693 mg, 94%). LC-MS ESI m/z: 524 (M+H)$^+$, T$_r$=3.25 min. method 1. And (3R,5R)-3-[1-methyl-1-(6-trifluoromethyl-pyridin-2-yl)-ethylamino]-5-(2-fluoro-phenyl)-1-(4-difluoromethoxy-phenyl)-pyrrolidin-2-one (562 mg, 27%), analytical LCC SFC (Chiralcel® OD-H column, 10% MeOH (0.2% IPAm)/CO$_2$, 5 mL/min, 225 nM) T$_r$=1.69 min. $^1$H NMR (400 MHz, DMSO-d$_6$): δ 8.07 (d, J=7.9 Hz, 1H), 8.02 (dd, J=7.8, 7.8 Hz, 1H), 7.70 (d, J=7.5 Hz, 1H), 7.30-7.18 (m, 4H), 7.11-7.01 (m, 4H), 7.01 (t, J=73.9 Hz, 1H), 5.41 (dd, J=9.4, 6.4 Hz, 1H), 3.48-3.41 (m, 1H), 2.94 (d, J=3.5 Hz, 1H), 2.73-2.64 (m, 1H), 1.71 (dd, J=22.0, 10.1 Hz, 1H), 1.47 (s, 3H), 1.42 (s, 3H).

LC-MS ESI m/z: 524 (M+H)$^+$, T$_r$=3.21 min., method 1.

Salt formation: Add p-toluene sulfonic acid hydrate (199 mg, 1.03 mmol) to (3R,5R)-3-[1-methyl-1-(6-trifluoromethyl-pyridin-2-yl)-ethylamino]-5-(2-fluoro-phenyl)-1-(4-difluoromethoxy-phenyl)-pyrrolidin-2-one (540 mg, 1.03 mmol) in methanol to give a homogeneous solution. Concentrate under reduced pressure to give an off white foam (730 mg, 100%). LC-MS ESI m/z: 524 (M+H)$^+$, T$_r$=3.26 min. method 1.

The following compounds are prepared essentially by the method of Example 16.

TABLE 5

| Ex. No. | Compound, Name, Physical Data, Yield and Comment |
|---|---|
| 17 | 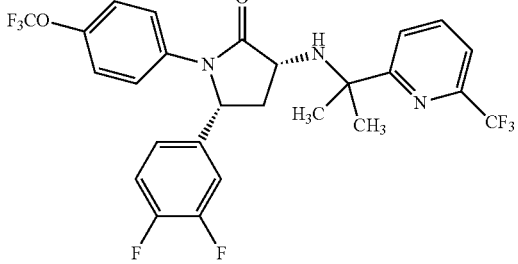<br>(3R,5R)-3-[1-Methyl-1-(6-trifluoromethyl-pyridin-2-yl)-ethylamino]-5-(3,4-difluoro-phenyl)-1-(4-trifluoromethoxy-phenyl)-pyrrolidin-2-one<br>$^1$H NMR (400 MHz, CDCl$_3$) δ 7.82-7.76 (m, 2H), 7.48 (dd, J = 1.8, 6.6 Hz, 1H), 7.25-7.24 (m, 1H), 7.23-7.23 (m, 2H), 7.06-7.00 (m, 2H), 6.97-6.92 (m, 1H), 6.89-6.86 (m, 1H), 4.89 (dd, J = 6.2, 9.7 Hz, 1H), 3.42 (dd, J = 7.9, 10.5 Hz, 1H), 2.75-2.69 (m, 1H), 1.81-1.73 (m, 1H), 1.55 (s, 3H), 1.52 (s, 3H).<br>LC-MS ESI m/z: 560 (M + H)$^+$, T$_r$ = 2.51 min., method 2.<br>Yield 40%.<br>LCC (Chiralpak AD-H column, 60:40 isopropyl alcohol:heptane with 0.2% DMEA, 0.6 mL/min, 250 nM) T$_r$ = 9.5 min. |
| 18 | 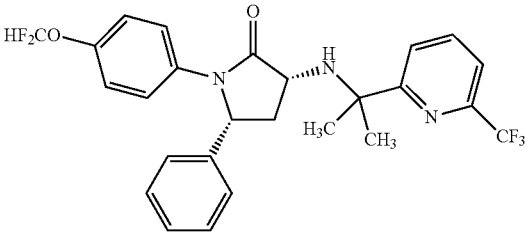<br>(3R,5R)-3-[1-Methyl-1-(6-trifluoromethyl-pyridin-2-yl)-ethylamino]-5-phenyl-1-(4-difluoromethoxy-phenyl)-pyrrolidin-2-one<br>$^1$H NMR (400 MHz, CDCl$_3$) δ 7.85 (d, J = 7.9 Hz, 1H), 7.77 (t, J = 7.9 Hz, 1H), 7.47 (d, J = 7.5 Hz, 1H), 7.24-7.16 (m, 5H), 7.13-7.11 (m, 2H), 6.91 (d, J = 9.2 Hz, 2H), 6.33 (t, J = 74 Hz, 1H), 4.91 (dd, J = 5.9, 9.9 Hz, 1H), 3.42 (dd, J = 7.9, 11.0 Hz, 1H), 2.75-2.68 (m, 1H), 1.87-1.78 (m, 1H), 1.56 (s, 3H), 1.52 (s, 3H).<br>LC-MS ESI m/z: 506 (M + H)$^+$, T$_r$ = 2.17 min., method 2. LCC SFC (Chiralcel ® OD-H column, 10% MeOH (0.2% IPAm)/CO$_2$, 5 mL/min, 230 nM) T$_r$ = 2.35 min.<br>Yield 18%<br>Comment: Separate the crude racemic mixture by SFC.<br>Salt formation: tosylate—with 1 equivalent p-toluene sulfonic acid in isopropanol. Concentrate to a light brown foam (283 mg, 93%).<br>LC-MS ESI m/z: 506 (M + H)$^+$, T$_r$ = 2.15 min., method 2. |
| 19 | 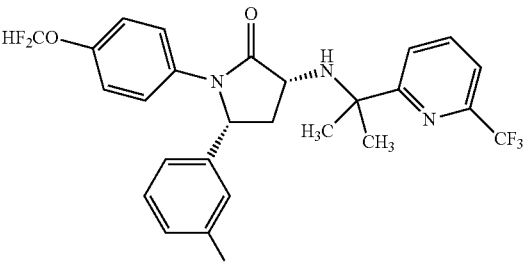<br>(3R,5R)-3-[1-Methyl-1-(6-trifluoromethyl-pyridin-2-yl)-ethylamino]-5-(3-fluoro-phenyl)-1-(4-difluoromethoxy-phenyl)-pyrrolidin-2-one<br>$^1$H NMR (400 MHz, CDCl$_3$) δ 7.83 (d, J = 7.9 Hz, 1H), 7.77 (t, J = 7.9 Hz, 1H), 7.48 (d, J = 7.5 Hz, 1H), 7.24-7.15 (m, 3H), 6.95-6.91 (m, 3H), 6.88-6.82 (m, 2H), 6.35 (t, J = 74 Hz, 1H), 4.91 (dd, J = 6.2, 9.7 Hz, 1H), 3.42 (dd, J = 7.9, 10.6 Hz, 1H), 2.75-2.69 (m, 1H), 1.83-1.75 (m, 1H), 1.55 (s, 3H), 1.51 (s, 3H).<br>LC-MS ESI m/z: 524 (M + H)$^+$, T$_r$ = 2.24 min., method 2.<br>Yield 25%<br>Comment: Separate the crude racemic mixture by SFC.<br>LCC SFC (Chiralcel ® OD-H column, 10% MeOH (0.2% IPAm)/CO$_2$, 5 mL/min, 230 nM) T$_r$ = 1.96 min. |

TABLE 5-continued

| Ex. No. | Compound, Name, Physical Data, Yield and Comment |
|---|---|
| | Salt formation: tosylate—with 1 equivalent p-toluene sulfonic acid in isopropanol. Concentrate to a colorless foam (425 mg, 98%).<br>LC-MS ESI m/z: 524 (M + H)$^+$, T$_r$ = 2.21 min., method 2. |
| 20 | 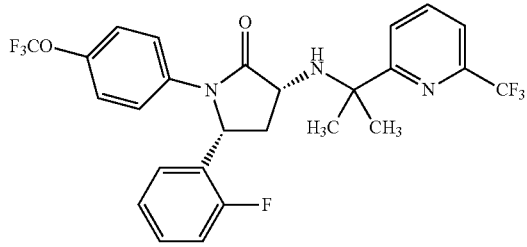 [SMILES: CC(C)(N[C@@H]1C[C@H](c2ccccc2F)N(c2ccc(OC(F)(F)F)cc2)C1=O)c1cccc(C(F)(F)F)n1]<br><br>(3R,5R)-3-[1-Methyl-1-(6-trifluoromethyl-pyridin-2-yl)-ethylamino]-5-(2-fluoro-phenyl)-1-(4-trifluoromethoxy-phenyl)-pyrrolidin-2-one<br>$^1$H NMR (400 MHz, CDCl$_3$) δ 7.84-7.76 (m, 3H), 7.48 (d, J = 7.5 Hz, 1H), 7.29 (d, J = 8.4 Hz, 2H), 7.15 (q, J = 6.9 Hz, 1H), 7.08-7.02 (m, 3H), 6.99-6.93 (m, 2H), 5.35-5.27 (m, 1H), 3.47-3.43 (m, 1H), 2.91-2.87 (m, 1H), 1.91-1.74 (m, 1H), 1.56 (3H), 1.52 (s, 3H).<br>Analytical chiral SFC (Chiralcel ® OD-H column, 10% MeOH (0.2% IPAm)/CO$_2$, 5 mL/min, 225 nM) T$_r$ = 1.04 min.<br>LC-MS ESI m/z: 542.0 (M + H)$^+$, T$_r$ = 2.50 min., method 2.<br>Yield 37%.<br>Salt formation: tosylate—with 1 equivalent p-toluene sulfonic acid in isopropanol. Crystallize from ether-methanol to give crystals (0.51 g, 76%)<br>LC-MS ESI m/z: 542.0 (M + H)$^+$, T$_r$ = 2.42 min., method 2 |
| 21 | 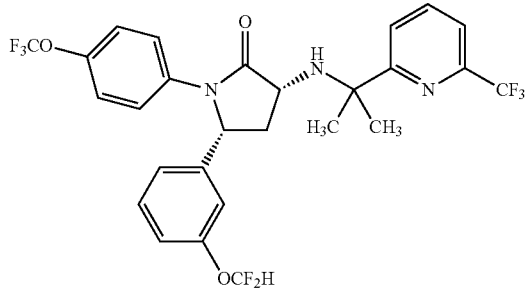<br><br>(3R,5R)-3-[1-Methyl-1-(6-trifluoromethyl-pyridin-2-yl)-ethylamino]-5-(3-difluoromethoxy-phenyl)-1-(4-trifluoromethoxy-phenyl)-pyrrolidin-2-one<br>$^1$H NMR (400 MHz, CDCl$_3$) δ 7.83-7.76 (m, 2H), 7.48 (d, J = 7.0 Hz, 1H), 7.26-7.19 (m, 4H), 7.03 (d, J = 8.8 Hz, 2H), 6.98 (d, J = 7.5 Hz, 1H), 6.91 (d, J = 8.4 Hz, 1H), 6.87 (s, 1H), 6.32 (t, J = 72 Hz, 1H), 4.92 (dd, J = 6.2, 9.7 Hz, 1H), 3.43 (dd, J = 7.9, 10.6 Hz, 1H), 2.93-2.83 (m, 1H), 2.77-2.70 (m, 1H), 1.84-1.76 (m, 1H), 1.55 (s, 3H), 1.52 (s, 3H).<br>LC-MS ESI m/z: 589.8. (M + H)$^+$, T$_r$ = 2.43 min., method 2<br>Analytical chiral SFC (Chiralcel ® OD-H column, 10% IPA (0.2% IPAm)/CO$_2$, 5 mL/min, 225 nM) T$_r$ = 1.27 min.<br>Yield 32% |

TABLE 5-continued

| Ex. No. | Compound, Name, Physical Data, Yield and Comment |
|---|---|
| 22 | 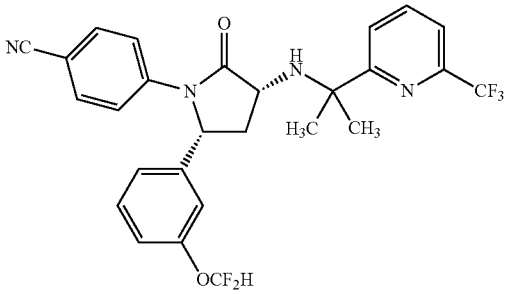

4-[(3R,5R)-3-[1-Methyl-1-(6-trifluoromethyl-pyridin-2-yl)-ethylamino]-2-oxo-5-(3-difluoromethoxy-phenyl)-pyrrolidin-1-yl]-benzonitrile
$^1$H NMR (400 MHz, CDCl$_3$): δ 7.79-7.77 (m, 2H), 7.49-7.37 (m, 4H), 7.47-7.37 (m, 1H), 7.24-7.20 (m, 2H), 6.97 (s, 1H), 6.94 (d, J = 4.4 Hz, 1H), 6.92 (s, 1H), 6.86 (s, 1H), 6.38 (t, J = 72 Hz, 1H), 4.95 (dd, J = 6.2, 10.1 Hz, 1H), 3.44 (dd, J = 7.9, 11.0 Hz, 1H), 2.87 (s, 1H), 2.78-2.72 (m, 1H), 1.80 (dt, J = 12.3, 10.6 Hz, 1H), 1.54 (s, 3H), 1.53 (s, 3H),
LC-MS ESI m/z: 531.0. (M + H)$^+$, T$_r$ = 2.11 min., method 2
Analytical chiral SFC (Chiralpak AD-H column, 25% IPA (0.2% IPAm)/CO$_2$, 5 mL/min, 230 nM) T$_r$ = 0.81 min.
Yield 44% |
| 23 | 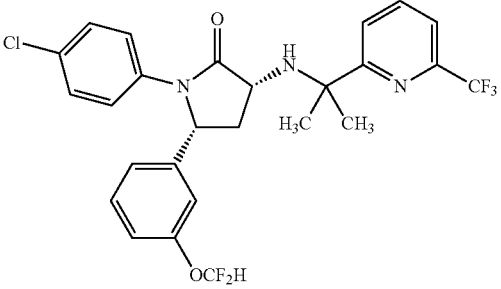

(3R,5R)-3-[1-Methyl-1-(6-trifluoromethyl-pyridin-2-yl)-ethylamino]-5-(3-difluoromethoxy-phenyl)-1-(4-chloro-phenyl)-pyrrolidin-2-one
$^1$H NMR (400 MHz, CDCl$_3$): δ 7.83-7.75 (m, 2H), 7.47 (d, J = 7.5 Hz, 1H), 7.22-7.15 (m, 5H), 6.96 (d, J = 7.9 Hz, 1H), 6.91 (d, J = 7.9 Hz, 1H), 6.87 (s, 1H), 6.36 (t, J = 72 Hz, 1H), 4.90 (dd, J = 6.2, 9.7 Hz, 1H), 3.42 (dd, J = 7.9, 10.6 Hz, 1H), 2.83-2.69 (m, 1H), 1.83-1.74 (m, 1H), 1.55 (s, 3H), 1.51 (s, 3H).
LC-MS ESI m/z: 539.8. (M + H)$^+$, T$_r$ = 2.3 min., method 2
Analytical chiral SFC (Chiralcel ® OD-H column, 20% IPA (0.2% IPAm)/CO$_2$, 5 mL/min, 230 nM) T$_r$ = 1.41 min.
Yield 31% |
| 24 | 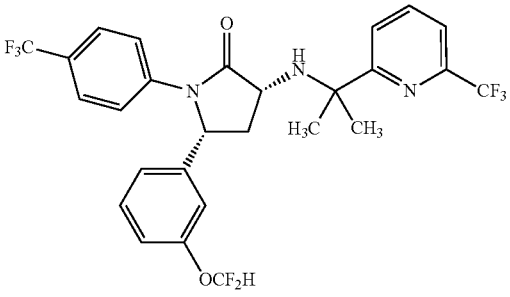

(3R,5R)-3-[1-Methyl-1-(6-trifluoromethyl-pyridin-2-yl)-ethylamino]-5-(3-difluoromethoxy-phenyl)-1-(4-trifluoromethyl-phenyl)-pyrrolidin-2-one
$^1$H NMR (400 MHz, CDCl$_3$): δ 7.82-7.76 (m, 2H), 7.49 (d, J = 6.6 Hz, 1H), 7.44 (d, J = 8.8 Hz, 1H), 7.37 (d, J = 8.4 Hz, 2H), 7.24-7.20 (m, 2H), 6.98 (d, J = 7.9 Hz, 1H), 6.92 (d, J = 7.9 Hz, 1H), 6.89 (s, 1H), 6.35 (t, J = 72 Hz 1H), 4.97 (dd, J = 6.4, 9.9 Hz, 1H), 3.45 (dd, J = 7.9, 10.6 Hz, 1H), 2.87-2.72 (m, 3H), 1.85-1.77 (m, 1H), 1.56 (s, 2H), 1.53 (s, 2H). |

LC-MS ESI m/z: 574.2. (M + H)+, T$_r$ = 2.36 min., method 2
Analytical chiral SFC (Chiralcel ® OD-H column, 10% IPA (0.2% IPAm)/CO$_2$,
5 mL/min, 230 nM) T$_r$ = 1.48 min.
Yield 32%

25

(3R,5R)-3-[1-Methyl-1-(6-trifluoromethyl-pyridin-2-yl)-ethylamino]-5-(3-
difluoromethoxy-phenyl)-1-(4-difluoromethoxy-phenyl)-pyrrolidin-2-one
$^1$H NMR (400 MHz, CDCl$_3$): δ 7.84-7.76 (m, 2H), 7.48 (d, J = 7.5 Hz, 1H),
7.23-7.19 (m, 2 H), 6.99-6.88 (m, 6H), 6.36 (t, J = 72 Hz, 1H), 6.35 (t, J = 72 Hz,
1H) 4.92 (dd, J = 6.2, 10.1 Hz, 1H), 3.43 (dd, J = 8.1, 10.8 Hz, 1H), 2.86-2.73
(m, 1H), 1.84-1.76 (m, 1H), 1.84-1.76 (m, 1H), 1.56 (s, 3H), 1.52 (s, 3H).
LC-MS ESI m/z: 572.2. (M + H)+, T$_r$ = 2.15 min., method 2
Analytical chiral SFC (Chiralcel ® OD-H column, 10% EtOH (0.2%
IPAm)/CO$_2$, 5 mL/min, 225 nM) T$_r$ = 1.83 min.
Yield 33%

Example 26

(3R,5R)-3-[1-Methyl-1-(6-trifluoromethyl-pyridin-2-yl)-ethylamino]-5-[3-[3-fluoro-propoxy)-phenyl]-1-(4-trifluoromethyl-phenyl)-pyrrolidin-2-one

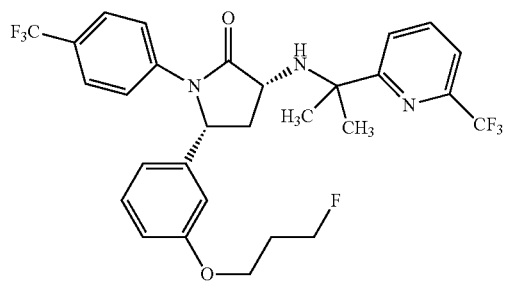 [SMILES: CC(C)(N[C@@H]1C[C@H](c2cccc(OCCCF)c2)N(c2ccc(C(F)(F)F)cc2)C1=O)c1cccc(C(F)(F)F)n1]

Dissolve (3R,5R)-3-[1-methyl-1-(6-trifluoromethyl-pyridin-2-yl)-ethylamino]-5-(3-hydroxy-phenyl)-1-(4-trifluoromethyl-phenyl)-pyrrolidin-2-one (520 mg, 0.99 mmol) in DMF (9 mL) and add cesium carbonate (1.9 g, 5.9 mmol) and 1-bromo-3-fluoro-propane (170 mg, 1.19 mmol). Stir the mixture at ambient temperature for 19.5 hours and dilute with EtOAc. Wash with brine, dry over sodium sulfate, filter, and concentrate the organic to residue. Purify the residue by silica gel chromatography (30% EtOAc-hexane) to obtain (3R,5R)-3-[1-methyl-1-(6-trifluoromethyl-pyridin-2-yl)-ethylamino]-5-[3-(3-fluoro-propoxy)-phenyl]-1-(4-trifluoromethyl-phenyl)-pyrrolidin-2-one (447 mg, 77%) as a colorless oil. $^1$H NMR (400 MHz, DMSO-d$_6$): δ 8.08 (d, J=7.9 Hz, 1H), 8.01 (dd, J=7.7, 7.7 Hz, 1H), 7.70 (d, J=7.5 Hz, 1H), 7.58 (d, J=8.8 Hz, 2H), 7.51 (d, J=8.8 Hz, 2H), 7.13 (dd, J=7.9, 7.9 Hz, 1H), 6.82-6.70 (m, 3H), 5.18 (dd, J=9.7, 6.6 Hz, 1H), 4.58 (t, J=5.9 Hz, 1H), 4.46 (t, J=5.9 Hz, 1H), 4.02-3.88 (m, 2H), 3.47-3.39 (m, 1H), 2.96 (d, J=3.5 Hz, 1H), 2.73-2.63 (m, 1H), 2.06-1.92 (m, 2H), 1.63 (dd, J=22.0, 10.5 Hz, 1H), 1.47 (s, 3H), 1.42 (s, 3H). LC-MS ESI m/z: 584.0 (M+H)+, T$_r$=3.61 min., method 1.

Example 27

4-[(3R,5R)-3-[1-Methyl-1-(6-trifluoromethyl-pyridin-2-yl)-ethylamino]-2-oxo-5-(3-trifluoromethoxy-phenyl)-pyrrolidin-1-yl]-benzonitrile

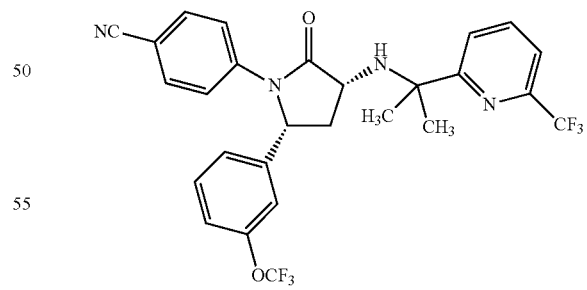

Add trifluoroacetic acid (2.00 mL, 26.43 mmol) to a biphasic mixture of 4-[(R)-2-oxo-3-((R)-1-phenyl-ethylamino)-5-(3-trifluoromethoxy-phenyl)-2,5-dihydro-pyrrol-1-yl]-benzonitrile in dichloromethane (12 mL) and water (4.9 mL). Stir at ambient temperature for 2 hours. Observe significant formation of 4-[(R)-2,3-dioxo-5-(3-trifluoromethoxy-phenyl)-pyrrolidin-1-yl]-benzonitrile (LC-MS ESI m/z: 361 (M+H)$^+$, T$_r$=2.34 min., method 2. Wash the reaction mixture with water. Filter the organic phase through sodium sulfate and add 1-methyl-1-(6-trifluoromethyl-pyridin-2-yl)-ethylamine (1.30 g, 6.35 mmol). Heat to reflux temperature for 18 hours. Partially concentrate reaction mixture and place on a silica gel chromatography column. Purify by silica gel chromatography (25% ethyl acetate-hexane) to obtain 4-[(R)-3-[1-methyl-1-(6-trifluoromethyl-pyridin-2-yl)-ethylamino]-2-oxo-5-(3-trifluoromethoxy-phenyl)-2,5-dihydro-pyrrol-1-yl]-benzonitrile (1.06 g, 37%). $^1$H NMR (400 MHz, CDCl$_3$) δ 7.71 (t, J=7.9 Hz, 1H), 7.64-7.61 (m, 2H), 7.59 (d, J=7.9 Hz, 1H), 7.53-7.44 (m, 4H), 7.26-7.24 (m, 1H), 7.04-6.96 (m, 2H), 6.80 (s, 1H), 5.38 (d, J=2.6 Hz, 1H), 4.99-4.97 (m, 1H), 4.69 (d, J=2.6 Hz, 1H), 1.65 (d, J=7.5 Hz, 6H).

Dissolve 4-[(R)-3-[1-methyl-1-(6-trifluoromethyl-pyridin-2-yl)-ethylamino]-2-oxo-5-(3-trifluoromethoxy-phenyl)-2,5-dihydro-pyrrol-1-yl]-benzonitrile (1.06 g, 1.94 mmol) in acetic acid (19.4 mL) and add sodium cyanoborohydride (609 mg. 9.70 mmol). Stir 1 hr. at ambient temperature. Concentrate under reduced pressure. Dissolve the residue in dichloromethane and concentrate. Partition the residue between dichloromethane and 5% NaHCO$_3$ solution and extract with dichloromethane. Combine dichloromethane extracts, dry over magnesium sulfate, filter and concentrate under reduced pressure. Purify the residue by silica gel chromatography (25% ethyl acetate-hexane) to obtain 4-[(3R,5R)-3-[1-Methyl-1-(6-trifluoromethyl-pyridin-2-yl)-ethylamino]-2-oxo-5-(3-trifluoromethoxy-phenyl)-pyrrolidin-1-yl]-benzonitrile (751 mg, 71%). $^1$H NMR (400 MHz, CDCl$_3$) δ 7.80-7.76 (m, 2H), 7.50-7.46 (m, 3H), 7.38 (d, J=8.8 Hz, 2H), 7.29-7.23 (m, 1H), 7.05 (t, J=7.3 Hz, 2H), 6.95 (s, 1H), 4.98 (dd, J=6.2, 9.7 Hz, 1H), 3.46 (dd, J=8.1, 10.8 Hz, 1H), 2.83-2.74 (m, 1H), 1.85-1.76 (m, 1H), 1.54 (d, J=7.0, 6H). LC-MS ESI m/z: 549.0 (M+H)$^+$, T$_r$=2.285 min., method 2.

Tosylate Salt formation: Add p-toluenesulonic acid monohydrate (28.2 mg, 0.146 mmol) to a solution of 4-[(3R,5R)-3-[1-methyl-1-(6-trifluoromethyl-pyridin-2-yl)-ethylamino]-2-oxo-5-(3-trifluoromethoxy-phenyl)-pyrrolidin-1-yl]-benzonitrile (80 mg, 0.146 mmol) in dichloromethane. Evaporate to give a quantitative mass balance of 4-[(3R,5R)-3-[1-methyl-1-(6-trifluoromethyl-pyridin-2-yl)-ethylamino]-2-oxo-5-(3-trifluoromethoxy-phenyl)-pyrrolidin-1-yl]-benzonitrile tosylate as a foam. LC-MS ESI m/z: 548.6 (M+H)$^+$, 571.6 (M+Na)$^+$, T$_r$=2.34 min., method 2.

Hydrochloride Salt formation: Add concentrated HCl (2.11 mL g, 25.5 mmol) solution to a yellow solution of 4-[(3R,5R)-3-[1-methyl-1-(6-trifluoromethyl-pyridin-2-yl)-ethylamino]-2-oxo-5-(3-trifluoromethoxy-phenyl)-pyrrolidin-1-yl]-benzonitrile (10.70 g, 19.5 mmol) in ethyl acetate at 70° C. Add slowly cyclohexane (360 mL) and heat to reflux for 30 min until precipitate forms. Cool to 50° C. and stir for 2 h., then allow to stir at room temperature. Sonicate the precipitate mixture, chill in ice-bath, and filter to give 11.7 g (102% yield, undried) of 4-[(3R,5R)-3-[1-methyl-1-(6-trifluoromethyl-pyridin-2-yl)-ethylamino]-2-oxo-5-(3-trifluoromethoxy-phenyl)-pyrrolidin-1-yl]-benzonitrile hydrochloride. LC-MS ESI m/z: 549.0 (M+H)$^+$, T$_r$=2.44 min., method 2.

Example 28

(3R,5R)-3-[1-Methyl-1-(6-trifluoromethyl-pyridin-2-yl)-ethylamino]-5-(3-trifluoromethyl-phenyl)-1-(4-trifluoromethoxy-phenyl)-pyrrolidin-2-one

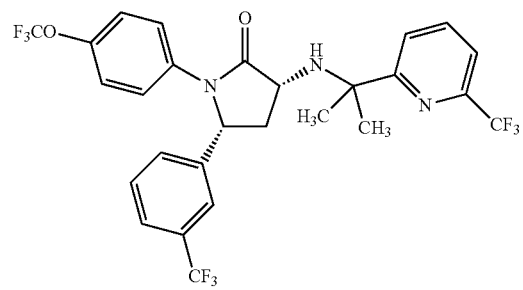 [SMILES: CC(C)(N[C@@H]1C[C@H](c2cccc(C(F)(F)F)c2)N(c2ccc(OC(F)(F)F)cc2)C1=O)c1cccc(C(F)(F)F)n1]

Dissolve (±)-3-[1-methyl-1-(6-trifluoromethyl-pyridin-2-yl)-ethylamino]-1-(4-trifluoromethoxy-phenyl)-5-(3-trifluoromethyl-phenyl)-1,5-dihydro-pyrrol-2-one (5.89 g, 10.0 mmol) in acetic acid (30 mL) and add sodium cyanoborohydride (1.26 g, 20.0 mmol). Stir for 30 min at ambient temperature. Pour reaction mixture into a mixture of saturated sodium bicarbonate solution and ethyl acetate. Extract the aqueous layer with additional ethyl acetate. Combine the organic extracts and wash with brine, dry over sodium sulfate, filter and concentrate under reduced pressure. Purify by silica gel chromatography (45% EtOAc-hexane) to yield (±)-3-[1-methyl-1-(6-trifluoromethyl-pyridin-2-yl)-ethylamino]-1-(4-trifluoromethoxy-phenyl)-5-(3-trifluoromethyl-phenyl)-pyrrolidin-2-one (2.55 g, 43%) as a racemic mixture. LC-MS ESI m/z: 592.0 (M+H)$^+$, T$_r$=2.63 min., method 2

Separate the racemic mixture by Supercritical Fluid Chromatography (SFC) on a Chiralcel® OD-H column (21×250 mm, 5 μm) eluting with 15% methanol—0.2% isopropylamine in carbon dioxide (70 mL/min) to give (3S,5S)-3-[1-Methyl-1-(6-trifluoromethyl-pyridin-2-yl)-ethylamino]-1-(4-trifluoromethoxy-phenyl)-5-(3-trifluoromethyl-phenyl)-pyrrolidin-2-one (640 mg, 25%) analytical chiral SFC (Chiralcel® OD-H column (4.6×150 mm), 15:85 3A EtOH/heptane (0.2% DMEA)/CO$_2$, 0.6 mL/min, 260 nM) T$_r$=4.4 min. $^1$H NMR (400 MHz, CDCl$_3$) δ 7.83-7.76 (m, 2H), 7.50-7.48 (m, 1H), 7.44 (d, J=7.5 Hz, 1H), 7.39-7.30 (m, 3H), 7.25-7.23 (m, 2H), 7.03 (d, J=8.8 Hz, 2H), 5.00 (dd, J=6.2, 9.7 Hz, 1H), 3.46 (dd, J=7.9, 11.0 Hz, 1H), 2.80-2.73 (m, 1H), 1.85-1.77 (m, 1H), 1.56 (s, 3H), 1.53 (s, 3H). LC-MS ESI m/z: 592.0 (M+H)$^+$, T$_r$=2.63 min., method 2 And (3R,5R)-3-[1-methyl-1-(6-trifluoromethyl-pyridin-2-yl)-ethylamino]-1-(4-trifluoromethoxy-phenyl)-5-(3-trifluoromethyl-phenyl)-pyrrolidin-2-one (640 mg, 25%), Analytical chiral SFC (Chiralcel® OD-H column (4.6×150 mm), 15:85 3A EtOH/heptane (0.2% DMEA)/CO$_2$, 0.6 mL/min, 260 nM) T$_r$=5.6 min.

$^1$H NMR (400 MHz, CDCl$_3$) δ 7.83-7.76 (m, 2H), 7.50-7.48 (m, 1H), 7.44 (d, J=7.5 Hz, 1H), 7.39-7.30 (m, 3H), 7.25-7.23 (m, 2H), 7.03 (d, J=8.8 Hz, 2H), 5.00 (dd, J=6.2, 9.7 Hz, 1H), 3.46 (dd, J=7.9, 11.0 Hz, 1H), 2.80-2.73 (m, 1H), 1.85-1.77 (m, 1H), 1.56 (s, 3H), 1.53 (s, 3H).

LC-MS ESI m/z: 592 (M+H)$^+$, T$_r$=2.65 min., method 2
Hydrochloride salt formation: Add HCl (1.3 mL, 1.3 mmol, 1M in ether) to (3R,5R)-3-[1-methyl-1-(6-trifluoromethyl-pyridin-2-yl)-ethylamino]-1-(4-trifluoromethoxy-phenyl)-5-(3-trifluoromethyl-phenyl)-pyrrolidin-2-one (569 mg, 0.96 mmol) in ether to give a heterogeneous solution. Concentrate under reduced pressure and crystallize the residue from acetone-ether. Filter the precipitate and dry under vacuum to give a white solid (478 mg, 79%). LC-MS ESI m/z: 591.8 (M+H)$^+$, T$_r$=2.63 min., method 2.

As mentioned, the compounds of the present invention are selective and highly potent inverse agonists or antagonists of the CB-1 receptor and are therefore useful in the treatment of various disorders by virtue of this pharmacology. The following assays may be used to demonstrate the claimed compounds' CB-1 receptor activity, their selectivity for the CB-1 receptor, and their activity in animal models of various disorders believed to be treatable by CB-1 receptor inverse agonism or antagonism.

It is noted that by definition, a pure antagonist inhibits the ligand mediated activation of a receptor (i.e. blocks agonist dependent receptor stimulation). Some receptors, including the CB-1 receptor, produce signal transduction even in the absence of agonists (endogenous/exogenous), which is referred to as the receptor's basal activity or constitutive activity. With such receptors, inverse agonists not only inhibit agonist dependent stimulation of the receptor, but also reduce/inhibit the basal activity of the receptor. In that CB-1 receptors have basal signaling activity, inverse agonists are preferred to pure antagonists as therapeutic agents for CB-1 mediated disorders. The compounds of the present invention are selective inverse agonists or antagonists of the CB-1 receptor.

CB$_1$ and CB$_2$ In Vitro Functional Assays

Compounds of the present invention may be tested for functional activity at the CB-1 and CB-2 receptors in both agonist and antagonist modes using SPA (Scintillation Proximity Assay) based GTP-γ-$^{35}$S binding assays. All assay components are prepared in assay buffer (20 mM HEPES, 100 mM NaCl, 5 mM MgCl$_2$, pH 7.4) at room temperature. Semi-log dilutions of test compound are prepared in assay buffer containing BSA (0.125% final conc.) for the agonist mode assays. For the antagonist mode assays, test compounds are prepared in the same manner but also include an 80% efficacious dose of a full agonist (methanandamide). GTP-γ$^{35}$S binding for the antagonist assay may be measured in a 96 well format using a modification of an antibody capture technique previously described. (DeLapp, N W, et al. (1999) *J Pharmacol Exp Ther* 289:946-955.) The CB-2 receptor agonist activity may be measured using a similar method using hCB2-Sf9 membranes. The CB-1 receptor agonist activity may be measured using a whole membrane capture technique using hCB1-CHO membranes. All incubations are done at room temperature.

Antagonist Mode Assays
hCB1-CHO and rCB1-CHO Antagonist Assays:

hCB1-CHO or rCB1-CHO membranes (Applied Cell Sciences, Rockville, Md.) and GDP (1 μM final) are added to ice cold assay buffer and homogenized. Diluted compounds, GTP-γ-$^{35}$S (500 nM final conc.) and membranes are added to wells of an assay plate and incubated for 30 min. at room temperature. Next, a mixture containing Nonidet P40 detergent (0.2% final conc.), rabbit polyclonal IgG Gα$_{i-3}$ antibody (provided by Covance, Princeton, N.J.), and 1.25 mg anti-rabbit antibody scintillation proximity assay beads (GE Healthcare, Piscataway, N.J.) is added. The plates are sealed, vortexed, and incubated for an additional 2 hr. Plates are then centrifuged at 700×g for 10 min. and the radioactivity counted.

hCB1-Sf9 and hCB2-Sf9 Antagonist Assays:

hCB1-Sf9 and hCB2-5f9 membranes (Perkin Elmer, Boston, Mass.) are prepared essentially as above with 1 μM (final conc.) GDP for hCB1-5f9 and 0.05 μM (final conc.) GDP for hCB2-5f9. The assay is run essentially as described for the CHO membranes above. Diluted membranes are pre-incubated with test compound for 15 min., which is followed by addition of GTP-γ-$^{35}$S and a further 35 min. incubation. Nonidet P40 and anti-G$_i$-antibody are added sequentially with a 15 min. incubation after each addition. The SPA beads are then added, the plates are sealed and vortexed, and then incubated at room temperature for 1 hr.

Agonist Mode Assays
hCB1-CHO Agonist Assay:

hCB1-CHO membrane, GDP (1 μM final conc.), and saponin (10 μg/mL final conc., Sigma, St Louis, Mo.) are combined and prepared on ice as for the antagonist assays, above. Diluted test compounds, GTP-γ-$^{35}$S (500 nM final conc.) and membranes are combined in the assay plate and incubated for 30 min. Then 1 mg/well Wheatgerm Agglutinin SPA beads (GE Healthcare, Piscataway, N.J.) are added, plates are sealed and vortexed and incubate for 1 hr. before spinning and counting in the same fashion as for the antagonist assays, above.

hCB2-Sf9 Agonist Assay:

The hCB2-Sf9 assay is run essentially as for the hCB1-sf9 and hCB2-sf9 antagonist assays above, with no challenging agonist added. 1 μM (final conc.) GDP is added to the membrane solution and nonidet P40, anti-G$_i$-antibody, and SPA bead are added together in a cocktail.

Data are analyzed as follows: Background is subtracted from all wells. Percent agonist efficacy is determine by normalizing agonist/inverse agonist dose response data to the response obtained for a full agonist (methanandamide). Percent antagonist inhibition is calculated by first normalizing the data to the signal generated by a saturating concentration of the full agonist (methanandamide). Then the data are analyzed using a 4-parameter logistic reduced fit (Activity Base™ and XLFit3™ from IDBS, Emeryville, Calif.). K$_b$ values are determined using a modification of the Cheng-Prusoff relationship: K$_b$=IC$_{50}$/(1+[agonist]/EC50), where "IC50" is determined from a four parameter fit of displacement curves, "[agonist]" is the agonist challenge concentration (nM), and "EC50" is determined from a four parameter fit of a full agonist concentration response curve (Cheng and Prusoff 1973). Mean K$_b$ values are calculated as a mean of at least three independent determinations±standard error of the mean (SEM). (Cheng Y C and Prusoff W H. (1973), *Biochem Pharmacol* 22:3099-3108.) Exemplified compounds are found to be potent CB-1 inverse agonists (K$_b$≦10 nM, typically<2 nM) and to be selective over the CB-2 receptor (K$_{b\ CB-2}$/K$_{b\ CB-1}$>500, typically>1000).

Tables 6 and 7 summarize antagonists/inverse agonist properties of certain compounds of the present invention. The data indicate that the test compounds are potent CB-1 inverse agonists at both rat and human receptors and are selective over human CB-2 receptors. The agonist efficacy being less than zero indicates that the compounds decreased basal (constitutive) activity of the CB-1 receptor in vitro, which characterizes the compounds as inverse agonists at the CB-1 receptor.

TABLE 6

| Example No. | rCB-1 SPA GTPγS CHO Membrane Antagonist | hCB-1 SPA GTPγS CHO Membrane Antagonist | hCB-1 SPA GTPγS Sf9 Membrane 22.7 μg Antagonist | hCB-2 SPA GTPγS Sf9 Membrane Antagonist |
|---|---|---|---|---|
| 27 Tosylate salt | 0.238 (0.0982, n = 3) | 0.179 (0.0914, n = 4) | 1.77 (0.692, n = 2) | >18400 (n = 1) |
| 28 Free base | 0.756 (n = 1) | 2.37 (0.387, n = 2) | 1.76 | >11900 (n = 1) |
| 28 HCl salt | 0.196 (0.00552, n = 3) | 0.464 (0.415, n = 4) | 0.59 | >9090 |

All values are: Kb nM (standard error of the mean)

TABLE 7

| Example No. | hCB-1 SPA GTPγS CHO Membrane Agonist | | hCB-2 SPA GTPγS Sf9 Membrane Agonist |
|---|---|---|---|
| | Relative $EC_{50}$ inverse (nM) | % Relative Efficacy | Relative $EC_{50}$ (nM) |
| 27 Tosylate salt | 0.943 | −97.3 | >100000 |
| 28 Free base | 3.02 | −92.8 | >100000 |
| 28 HCl salt | 1.27 | −100 | >100000 |

Force Swim Test (FST)

The forced swim test is a well established animal model for depression, anxiety and avolition (lack of motivation)(Porsolt, et al. *Nature* (1977) 266, 730) (J. M. Witkin et al., *Trends Pharmacol Sci.* 2005 26:609-17). It can also be used as a model for the treatment of negative symptoms of schizophrenia.

Male NIH Swiss mice (Harlan Sprague-Dawley) are housed 12 mice/cage for 7-10 days prior to testing. On the day of testing, mice weighing 25-30 g, are brought to the testing room at least 1 hr. prior to dosing. Mice are dosed (p.o.) at 6-8 min. intervals with either vehicle (1% CMC/0.5% SLS/0.08% povidone/0.05 antifoam for CB1 inverse agonists) or test compound and put it into a clean cage (4 mice/cage).

To test, mice are placed individually in clear plastic cylinders (about 10 cm diameter×25 cm height) filled to 6 cm with water at 22-25° C. for six min. The duration of immobility during the last 4 min. is recorded. A mouse is regarded as immobile when floating motionless or making only those movements necessary to keep its head above the water.

The immobility time (in seconds) is analyzed by ANOVA using Dunnett's test. The minimum effective dose (MED) is considered to be the lowest dose of test compound at which a statistically significant decrease in the immobility time is observed versus the vehicle control. The compound of example 27 is tested essentially as described and is found to significantly reduce the duration of mobility in a dose dependent manner.

| Sample | Seconds of immobility | Dunett's Test (0.05) * against vehicle, # against Imipramine |
|---|---|---|
| Vehicle | 201 | # |
| Ex. 27 @ 1 mg/Kg | 170 | # |
| Ex. 27 @ 3 mg/Kg | 128 | * |
| Ex. 27 @ 10 mg/Kg | 80 | * |
| Imipramine @ 15 mg/Kg | 80 | * | n = 8 mice per group

Likewise, the compounds of example 11 and 28 are tested essentially as described and found to have minimum effective doses of 3 and 10 mg/Kg respectively (Dunett's Test (0.05) statistically significant).

Bioavailability

Methods for accessing bioavailability are well appreciated in the art. One such reference is *Medicinal Research Reviews* Vol 21 No. 5 382-396 (2001). Bioavailability of compounds may be estimated essentially as follows.

Cohorts of three or four 250-450 gram male Sprague-Dawley rats or approximately 10 kg Beagle dogs (female or male) are used. Animals do not need to be fasted for the i.v. portion of the study. Dogs are administered i.v. by cannulated cephalic vein and blood collections are by jugular vein. Animals are first dosed at 0.25 mg/kg i.v. and blood samples (0.2 mL) are then collected using EDTA as an anticoagulant at 0.0830, 0.25, 0.50, 1, 2, 4, 8, 12, 24, 48, 72, 96, and 120 hours. Next after at least two days and after 18-24 hours fasting, the animals are dosed at 1.0 mg/kg by oral gavage. During the course of a study the total of blood (ml) collected is not to exceed 1% of total body weight in grams. Should larger blood volumes be required, the sampled blood volume is replace with heparinized whole blood from a donor animal. When using a cross-over study design, rats receive a volume of heparinized whole blood following the final sample of each study day approximately equal to that removed during study.

Compound plasma concentrations are measured by LC/MS/MS assays. Data are then analyzed using standard non-compartmental pharmacokinetic analysis. Oral bioavailability is calculated as:

$$(AUC_{0\text{-}infinity}, oral / AUC_{0\text{-}infinity}, i.v.) \times (Dose, i.v. / Dose, oral) \times 100\%$$

The compounds of Examples 27 and 28 are tested and found to have oral bioavailability as follows:
Rat Bioavailability for Example 27HCl Salt:
Fasted, male SD rats
IV dose: 0.25 mg/kg, formulation: 20% v/v MEOP/80% v/v purified water PO dose: 1 mg/kg, formulation: 1% NaCMC/0.5% SLS/0.05% antifoam in purified water The oral bioavailability on average was 58±8.6% and is based on $AUC_{0-\infty}$.

Dog Bioavailability for Example 27HCl Salt:

Fasted, male beagle Dog

IV: 0.25 mg/kg, formulation: 20% v/v MEOP/80% v/v purified water

PO: 1 mg/kg, formulation: 1% NaCMC/0.5% SLS/0.05% antifoam in purified water

The oral bioavailability on average was 33±13% (Mean±SD, n=3 dogs) and is based on $AUC_{0-24hr}$.

Rat Bioavailability Example 28HCl Salt:

Fasted, male SD rats

IV dose: 0.25 mg/kg, formulation: 20% Pharmasolve™, 10% HPBCD in 25 mM phosphate buffer pH 3

PO dose: 1 mg/kg, formulation: 1% CMC, 0.5% SLS, 0.5% AF (in purified water)

The oral bioavailability is 40±6% (mean±s.d, n=3 rats) and is based on $AUC_{0-\infty}$.

Dog Bioavailability of Example 28HCl Salt:

Fasted, female beagle Dog

IV dose: 0.25 mg/kg, formulation: 20% pharmasolve, 10% HPBCD in 25 mM phosphate buffer pH3

PO dose: 1 mg/kg, formulation: 1% CMC, 0.5% SLS, 0.5% AF (in purified water)

The oral bioavailability is 32±18% (mean±s.d, n=2 dogs) and is based on $AUC_{0-\infty}$.

Human CYP Fingerprinting

CYP fingerprinting is well established technique and is used as an indication of potential risk of drug-drug interactions in the pharmaceutical sciences. Compounds of the present invention may be assayed by well known methods, essentially as follows: Compounds are incubated at 37° C. at a final concentration of 4 μM with pooled, mixed gender, human liver microsomes and 1 mM NADPH (Nicotine Adenine Dinucleotide Phosphate) (final conc.) for 0 and 30 min. without any CYP inhibitor and with each CYP inhibitor in separate incubations for 30 min. Each inhibitor is specific for an individual cytochrome P450. The specific inhibitors used for CYPs 2C9, 2D6 and 3A were sulfaphenazole, quinidine and ketoconazole, respectively. Ketoconazole (CYP3A) is made up at 25 mM in DMSO and then diluted in buffer to a final concentration of 10 μM. Quinidine (CYP2D6) is made up at 5 mM in 50/50 acetonitrile/water and then diluted in buffer to a final concentration of 10 μM. Sulfaphenazole (CYP2C9) is made up at 100 mM in DMSO and then diluted in buffer to a final concentration of 5 μM. Samples are analyzed by LC-MS in positive or negative electrospray mode using a Waters Acquity Ultra Performance LC coupled to a MicroMass Q-T of-2 mass spectrometer.

Data are analyzed using MetaboLynx™ version 4.1. With inhibitor present, a reduction in metabolite peak area of less than 30% (relative to the uninhibited control incubation) receives a designation of low risk of Drug Drug Interaction (DDI), a reduction in peak area between 30% and 70% receives a moderate risk of DDI and a reduction of more than 70% receives a high risk of DDI.

The compounds of Examples 27 and 28 are tested and found to have CYP fingerprints as follows:

TABLE 8

Risk of Drug Drug Interaction (DDI)

| Example No | CYP3A | CYP2D6 | CYP2C9 |
|---|---|---|---|
| 27 Tosylate salt | Low | Low | low |
| 28 HCl salt | Low | Low | low |

In Vivo Efficacy in Feeding Models

The ability of compounds of the present invention to reduce body weight may be tested in a rat feeding model essentially as follow. Establish diet-induced obese (DIO) male Long-Evans rats by ad lib feeding from weanling on a diet consisting of about 40% fat, about 39% carbohydrate and about 21% protein caloric content for at least 12 weeks. Administer test compound or vehicle to cohorts of rats (p.o., once daily) for two weeks. Determine compound potency as the dose required to produce a difference of 17 grams compared to the vehicle group after treatment for two weeks (T17 potency). This represents a minimally biologically relevant reduction of 3-4% of body weight compared to vehicle treatment after 2 weeks.

Antipsychotic Weight Gain Model

The ability of compounds of the present invention to maintain/reduce body weight during treatment with antipsychotics may be tested in a rat feeding model essentially as follow. Maintain adult lean, female Sprague-Dawley rats ad libitum on normal rodent chow Purina LabDiet 5001 (12.3% fat) and water. Treat one group (n~7) with vehicle (1% lactic acid) on days 1-14 while treating the rest with olanzapine (2 mg/kg, po). Follow food intake, monitor body weight and change in fat mass over a two week treatment. After 14 days of drug delivery, divide the olanzapine treated animals (n~8 per group) and treat one group with 0.3 mg/kg test compound plus olanzapine, treat a second group with 1 mg/kg test compound plus olanzapine and treat the final group with vehicle plus olanzapine for days 15-28.

We claim:
1. A compound of the formula

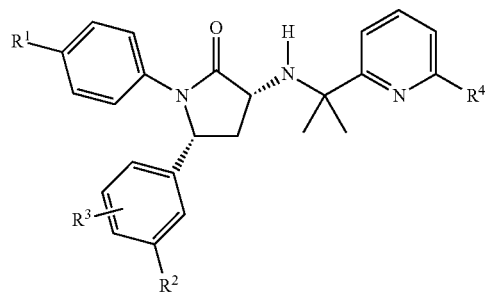

$R^1$ is selected from the group consisting of hydrogen, chloro, cyano, trifluoromethyl, difluoromethoxy, and trifluoromethoxy;

$R^2$ is selected from the group consisting of hydrogen, halo, cyano, $(C_1-C_3)$ alkyl substituted with from 1 to 5 fluoro groups, and $(C_1-C_3)$ alkoxy substituted with from 1 to 5 fluoro groups;

$R^3$ is selected from the group consisting of hydrogen, fluoro, and chloro;

R⁴ is selected from the group consisting of trifluoromethyl, cyano and cyclopropyl;

provided that, when R¹ is hydrogen, chloro, cyano, or trifluoromethyl, then R² is ($C_1$-$C_3$) alkoxy substituted with from 1 to 5 fluoro groups;

or a pharmaceutically acceptable salt thereof.

2. The compound according to claim 1 wherein R² is selected from the group consisting of hydrogen, fluoro, chloro, cyano, trifluoromethyl, 1,1-difluoroethyl, trifluoromethoxy, difluoromethoxy, and 1,1,2,2-tetrafluoroethoxy, or a pharmaceutically acceptable salt thereof.

3. The compound according to claim 2 wherein R² is selected from the group consisting of trifluoromethyl, 1,1-difluoroethyl, difluoromethoxy, trifluoromethoxy, and 1,1,2,2-tetrafluoroethoxy and R³ is hydrogen, or a pharmaceutically acceptable salt thereof.

4. The compound according to claim 1 wherein R¹ is difluoromethoxy or trifluoromethoxy, or a pharmaceutically acceptable salt thereof.

5. The compound according to claim 1 wherein R² is ($C_1$-$C_3$) alkoxy substituted with from 1 to 5 fluoro groups, or a pharmaceutically acceptable salt thereof.

6. The compound according to claim 5 wherein R³ is hydrogen, or a pharmaceutically acceptable salt thereof.

7. The compound according to claim 1 which is 4-[(3R,5R)-3-[1-Methyl-1-(6-trifluoromethyl-pyridin-2-yl)-ethylamino]-2-oxo-5-(3-trifluoromethoxy-phenyl)-pyrrolidin-1-yl]-benzonitrile, or a pharmaceutically acceptable salt thereof.

8. The compound according to claim 1 which is (3R,5R)-3-[1-Methyl-1-(6-trifluoromethyl-pyridin-2-yl)-ethylamino]-5-(3-trifluoromethyl-phenyl)-1-(4-trifluoromethoxy-phenyl)-pyrrolidin-2-one, or a pharmaceutically acceptable salt thereof.

9. A pharmaceutical composition comprising a compound according to claim 1, or a pharmaceutically acceptable salt thereof, and a pharmaceutically acceptable carrier, diluent, or excipient.

10. A method for the treatment of obesity in a human, comprising administering to a human in need of such treatment, an effective amount of a compound according to claim 1, or a pharmaceutically acceptable salt thereof.

11. A method for the treatment of cognitive impairment associated with schizophrenia in a human, comprising administering to a human in need of such treatment, an effective amount of a compound according to claim 1, or a pharmaceutically acceptable salt thereof.

12. A method for the treatment or prevention of weight gain associated with treatment with an antipsychotic in a human, comprising administering to a human in need of such treatment, an effective amount of a compound according to claim 1, or a pharmaceutically acceptable salt thereof.

13. A method for the treatment of negative symptoms associated with schizophrenia in a human, comprising administering to a human in need of such treatment, an effective amount of a compound according to claim 1, or a pharmaceutically acceptable salt thereof.

* * * * *